US012139533B2

(12) United States Patent
Miano et al.

(10) Patent No.: US 12,139,533 B2
(45) Date of Patent: Nov. 12, 2024

(54) LIQUID FORMULATIONS OF ANTI-CD200 ANTIBODIES

(71) Applicant: Alexion Pharmaceuticals, Inc., Boston, MA (US)

(72) Inventors: Dino Miano, Rocky Hill, CT (US); Bruce Mason, Madison, CT (US)

(73) Assignee: Alexion Pharmaceuticals, Inc., Boston, MA (US)

(*) Notice: Subject to any disclaimer, the term of this patent is extended or adjusted under 35 U.S.C. 154(b) by 613 days.

(21) Appl. No.: 16/954,868

(22) PCT Filed: Dec. 18, 2018

(86) PCT No.: PCT/US2018/066174
§ 371 (c)(1),
(2) Date: Jun. 17, 2020

(87) PCT Pub. No.: WO2019/126133
PCT Pub. Date: Jun. 27, 2019

(65) Prior Publication Data
US 2021/0087267 A1 Mar. 25, 2021

Related U.S. Application Data

(60) Provisional application No. 62/608,322, filed on Dec. 20, 2017.

(51) Int. Cl.
*A61K 39/395* (2006.01)
*C07K 16/28* (2006.01)
*A61K 39/00* (2006.01)

(52) U.S. Cl.
CPC .... *C07K 16/2803* (2013.01); *A61K 2039/505* (2013.01); *C07K 2317/565* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,403,484 A | 4/1995 | Ladner et al. | |
| 5,595,721 A | 1/1997 | Kaminski et al. | |
| 6,090,382 A | 7/2000 | Salfeld et al. | |
| 6,258,562 B1 | 7/2001 | Salfeld et al. | |
| 6,338,851 B1 | 1/2002 | Gorczynski | |
| 6,652,858 B2 | 11/2003 | Gorczynski et al. | |
| 6,749,854 B2 | 6/2004 | Gorczynski et al. | |
| 6,955,811 B2 | 10/2005 | Gorczynski et al. | |
| 6,984,625 B2 | 1/2006 | Gorczynski | |
| 7,238,352 B2 | 7/2007 | Gorczynski et al. | |
| 7,368,535 B2 | 5/2008 | Gorczynski et al. | |
| 7,408,041 B2 | 8/2008 | Bowdish et al. | |
| 7,422,739 B2 | 9/2008 | Anderson et al. | |
| 7,427,665 B2 | 9/2008 | Bowdish et al. | |
| 7,435,412 B2 | 10/2008 | Bowdish et al. | |
| 7,435,415 B2 | 10/2008 | Gelber | |
| 7,435,803 B2 | 10/2008 | Hansen et al. | |
| 7,452,536 B2 | 11/2008 | Gorczynski et al. | |
| 7,598,353 B2 | 10/2009 | Bowdish et al. | |
| 7,714,110 B2 | 5/2010 | Bowdish et al. | |
| 7,887,798 B2 | 2/2011 | Gorczynski et al. | |
| 7,915,000 B2 | 3/2011 | Bowdish et al. | |
| 8,075,884 B2 | 12/2011 | Bowdish et al. | |
| 8,114,403 B2 | 2/2012 | Bowdish et al. | |
| 8,187,877 B2 | 5/2012 | Bowdish et al. | |
| 8,252,285 B2 | 8/2012 | Rother et al. | |
| 8,637,014 B2 | 1/2014 | Rother et al. | |
| 8,709,415 B2 | 4/2014 | Bowdish et al. | |
| 8,840,885 B2 | 9/2014 | Bowdish et al. | |
| 8,986,684 B2 | 3/2015 | Wang | |
| 8,999,328 B2 | 4/2015 | Bowdish et al. | |
| 9,000,133 B2 | 4/2015 | Bowdish et al. | |
| 9,085,623 B2 | 7/2015 | Rother et al. | |
| 9,150,661 B2 | 10/2015 | Bowdish et al. | |
| 9,180,186 B2 | 11/2015 | Faas McKnight et al. | |
| 9,249,229 B2 | 2/2016 | Bowdish et al. | |
| 9,447,187 B2 | 9/2016 | Wang et al. | |
| RE46,323 E | 2/2017 | Rother et al. | |
| 9,862,767 B2 | 1/2018 | Rother et al. | |
| 11,802,154 B2 | 10/2023 | Mack et al. | |

(Continued)

FOREIGN PATENT DOCUMENTS

| JP | H0246297 A | 2/1990 |
|---|---|---|
| WO | 85/03508 A1 | 8/1985 |

(Continued)

OTHER PUBLICATIONS

Kausar, Fariha et al., "Ocrelizumab: a step forward in the evolution of B-cell therapy," Expert Opin. Biol. Ther., vol. 9(7):889-895 (2009).
Kretz-Rommel and Bowdish, "Rationale for anti-CD200 immunotherapy in B-CLL and other hematologic malignancies: new concepts in blocking immune suppression," Expert Opinion on Biological Therapy, vol. 8(1), pp. 5-15 (2008).
Kretz-Rommel, A. et al., "Blockade of CD200 in the presence or absence of antibody effector function: implications for anti-CD200 therapy," J Immuno., vol. 180:699-705 (2008).
Kretz-Rommel, Anke et al., "CD200 Expression on Tumor Cells Suppresses Antitumor Immunity: New Approaches to Cancer Immunotherapy," The Journal of Immunology, vol. 178:5595-5605 (2007).

(Continued)

*Primary Examiner* — Yunsoo Kim
(74) *Attorney, Agent, or Firm* — Nelson Mullins Riley & Scarborough LLP; Jane E. Remillard, Esq.; Jill Gorny Sloper, Esq.

(57) ABSTRACT

The present disclosure provides stable liquid pharmaceutical formulations comprising anti-CD200 antibodies or antigen-binding fragments thereof, and articles of manufacture and kits containing the formulations. Also featured are methods of using the formulations in cancer and autoimmune therapies, and for preventing, delaying or treating cell, tissue, or organ transplant rejection.

24 Claims, 6 Drawing Sheets
Specification includes a Sequence Listing.

(56) References Cited

U.S. PATENT DOCUMENTS

| | | |
|---|---|---|
| 2002/0168364 A1 | 11/2002 | Gorczynski et al. |
| 2002/0192215 A1 | 12/2002 | Hoek et al. |
| 2004/0018972 A1 | 1/2004 | Gorczynski et al. |
| 2004/0054145 A1 | 3/2004 | Gorczynski |
| 2004/0175692 A1 | 9/2004 | Bowdish et al. |
| 2004/0198661 A1 | 10/2004 | Bowdish et al. |
| 2005/0048069 A1 | 3/2005 | Gorczynski et al. |
| 2005/0074452 A1 | 4/2005 | Bowdish et al. |
| 2005/0107314 A1 | 5/2005 | Gorczynski et al. |
| 2005/0118163 A1* | 6/2005 | Mizushima ...... A61K 39/39591 514/557 |
| 2005/0129690 A1 | 6/2005 | Bowdish et al. |
| 2005/0169870 A1 | 8/2005 | Truitt et al. |
| 2006/0057651 A1 | 3/2006 | Bowdish et al. |
| 2006/0153846 A1 | 7/2006 | Krause et al. |
| 2007/0036786 A1 | 2/2007 | Tuaillon et al. |
| 2007/0065438 A1 | 3/2007 | Liversidge et al. |
| 2009/0053222 A1 | 2/2009 | Gorczynski et al. |
| 2010/0196374 A1 | 8/2010 | Wang |
| 2010/0239598 A1 | 9/2010 | Bowdish et al. |
| 2010/0285030 A1 | 11/2010 | Bowdish et al. |
| 2010/0291085 A1 | 11/2010 | Rother et al. |
| 2013/0158236 A1 | 6/2013 | Bowdish et al. |
| 2013/0189258 A1 | 7/2013 | Rother et al. |
| 2013/0202602 A1 | 8/2013 | Faas McKnight et al. |
| 2014/0170143 A1 | 6/2014 | Wang et al. |
| 2015/0368341 A1 | 12/2015 | Bowdish et al. |
| 2016/0009803 A1 | 1/2016 | Rother et al. |
| 2016/0033514 A1 | 2/2016 | McKnight et al. |
| 2016/0168237 A1 | 6/2016 | Fontenot et al. |
| 2021/0230273 A1 | 7/2021 | Mack et al. |

FOREIGN PATENT DOCUMENTS

| | | |
|---|---|---|
| WO | 94/28027 A1 | 12/1994 |
| WO | 97/21450 A1 | 6/1997 |
| WO | 99/24565 A1 | 5/1999 |
| WO | 01/87336 A1 | 11/2001 |
| WO | 02/11762 A2 | 2/2002 |
| WO | 02/42332 A2 | 5/2002 |
| WO | 02/059280 A2 | 8/2002 |
| WO | 02/095030 A2 | 11/2002 |
| WO | 2004060295 A2 | 7/2004 |
| WO | 2004/078938 A2 | 9/2004 |
| WO | 2005/115453 A2 | 12/2005 |
| WO | 2006/020266 A2 | 2/2006 |
| WO | 2006/031370 A2 | 3/2006 |
| WO | 2006/082515 A2 | 8/2006 |
| WO | 2007/037795 A2 | 4/2007 |
| WO | 2007/084321 A2 | 7/2007 |
| WO | 2008/089022 A2 | 7/2008 |
| WO | 2009/014744 A1 | 1/2009 |
| WO | 2009/014745 A1 | 1/2009 |
| WO | 2009/037190 A2 | 3/2009 |
| WO | 2009/83602 A1 | 7/2009 |
| WO | 2011/100538 A1 | 8/2011 |
| WO | 2012/106634 A1 | 8/2012 |
| WO | 2016/154290 A1 | 9/2016 |
| WO | 2018/102594 A1 | 6/2018 |
| WO | 2019/126536 A1 | 6/2019 |
| WO | 2019126133 A1 | 6/2019 |

OTHER PUBLICATIONS

Kretz-Rommel, Anke et al., "The Immuno-Regulatory Protein CD200 Is Overexpressed in a Subset of B-Cell Lymphocytic Leukemias and Plays a Role in Down-Regulating the TH1 Immune Response," J. Immunother., vol. 27(6):S46 (2004).
Levene, Adam P. et al., "Therapeutic monoclonal antibodies in oncology," Journal of the Royal Society of Medicine, vol. 98:146-152 (2005).
Lian, D. et al., "Synergy of Novel Anti-CD200 Antibody and Cyclosporine Enhance Myeloid-Derived Suppressor Cell Frequency and Leads to Long-Term Heart Allograft Survival," American Journal of Transplantation, vol. 11, Poster Board No. Session: P110.5-IV, p. 476, XP002739069, Apr. 4, 2011.
Mahadevan et al., 52nd American Society of Hematology (ASH) Annual Meeting and Exposition, Abstract 2465, 4 pages (2010).
Mahadevan, D. M.D. et al., "First-in-Human Phase I Dose Escalation Study of a Humanized Anti-CD200 Antibody (Samalizumab) in Patients with Advanced Stage B Cell Chronic Lymphocytic Leukemia (B-CLL) or Multiple Myeloma (MM)," Blood, vol. 116(21):2465-2467 (2010).
Marti, G.E. et al., "CD20 and CD5 Expression in B-Chronic Lymphocytic Leukemia," Ann. N.Y. Acad. Sci., vol. 651:480-483 (1992).
Mcwhirter, John R. et al., "Antibodies selected from combinatorial libraries block a tumor antigen that plays a key role In immunomodulation," PNAS, vol. 103(4):1041-1046 (2006).
Milani, Cannon et al., "Veltuzumab, an anti-CD20 mAb for the treatment of non-Hodgkin's lymphoma, chronic lymphocytic leukemia and immune thrombocytopenic purpura," Current Opinion in Molecular Therapeutics, vol. 11(2):200-207 (2009).
Morschhauser, Franck et al., "Humanized Anti-CD20 Antibody, Veltuzumab, in Refractory/Recurrent Non-Hodgkin's Lymphoma: Phase I/II Results," Journal of Clinical Oncology, vol. 27(20):3346-3353 (2009).
Nathan, Carl et al., "Putting the brakes on innate immunity: a regulatory role for CD200?" Nature Immunology, vol. 2(1):17-19 (2001).
Pallasch et al., "Disruption of T cell suppression in chronic lymphocytic leukemia by CD200 blockade," Leukemia Research, vol. 33(3), pp. 460-464 (2009).
Petermann, Kimberly B. et al., "CD200 is induced by ERK and is a potential therapeutic target in melanoma," The Journal of Clinical Investigation, vol. 117(12):3922-3929 (2007).
Preston, Sandy et al., "The leukocyte/neuron cell surface antigen OX2 binds to a ligand on macrophages," Eur. J. Immunol., vol. 27(8):1911-1918 (1997).
Ragheb, Rafik et al., "Preparation and functional properties of monoclonal antibodies to human, mouse and rat OX-2," Immunology Letters, vol. 68:311-315 (1999).
Ragheb, Rafik F.A. et al., "Exploration of OX-2 function in tolerance induction and graft acceptance using an anti-mouse OX-2 monoclonal antibody," Masters Abstracts International, vol. 38(4):971-972 (2000).
Ravandi et al., "Chronic lymphocytic leukemia (B-CLL) occurring with human immunodeficiency virus (HIV) infection: implications," Leukemia Research, vol. 27: 853-857 (2003).
Reddy, N.M. et al., Rituximab resistance and its association with changes in the internal domain of CD20 antigen and down-regulation of pro-apoptotic protein Bax and Bak in both rituximab-resistant cell lines (RRCL) and diffuse large B-cell lymphoma(DLBCL) patient (pt) samples, Journal of Clinical Oncology, 2006 ASCO Annual Meeting Proceedings, vol. 24(18S), Poster Presentation No. 17509 (2006).
Rijkers, Eva S.K. et al., "The inhibitory CD200R is differentially expressed on human and mouse T and B lymphocytes," Molecular Immunology, vol. 45:1126-1135 (2008).
Romagnani, Sergio et al., "Short Analytical Review, TH1 and TH2 in Human Diseases," Clinical Immunology and Immunopathology, vol. 80(3):225-235 (1996).
Rosenblum, Michael D. et al., "CD200 is a novel p53-target gene involved in apoptosis-associated immune tolerance," Blood, vol. 103(7):2691-2698 (2004).
Sequence alignment, 2015, 3 pages.
Simelyte et al., "CD200-Fc, a novel antiarthritic biological agent that targets proinflammatory cytokine expression in the joint of mice with collagen-induced arthritis," Arthritis & Rheumatism, vol. 58(4), pp. 1038-1043 (2008).
Supplementary European Search Report for EP 11 73 2296, dated Sep. 30, 2013.
Taylor, Neil et al., "Enhanced Tolerance to Autoimmune Uveitis in CD200-Deficient Mice Correlates wtih a Pronounced Th2 Switch in Response to Antigen Challenge, " The Journal of Immunology, vol. 174:143-154 (2005).

(56) References Cited

OTHER PUBLICATIONS

Tedder, Thomas F. et al., "Isolation and structure of a cDNA encoding the B1 (CD20) cell-surface antigen of human B lymphocytes," Proc. Natl. Acad. Sci. USA, vol. 85:208-212 (1988).
Teeling, Jessica L. et al., "The Biological Activity of Human CD20 Monoclonal Antibodies Is Linked to Unique Epitopes on CD20," The Journal of Immunology, vol. 177:362-371 (2006).
Transplantation Tech., Inc. WO02095030, "Modulation of CD200 Receptors as a Novel Method of Immunosuppression," Expert Opin. Ther. Patents, vol. 13(5):711-715 (2003).
Wang W. et al., "Antibody Structure Instability, and Formulation," Journal of Pharmaceutical Sciences, American Pharmaceutical Association, US, vol. 96 (1): 1-26(2007).
Wang W. et al., "Instability, stabilization, and formulation of liquid protein pharmaceuticals," International Journal of Pharmaceutics, vol. 185 (2):129-188 (1999).
Warne, I. et al., "Development of high concentration protein biopharmaceuticals: The use of platform approaches in formulation development," European Journal of Pharmaceutics and Biopharmaceutics, vol. 78 (2):208-212 (2011).
Wright, G.J. et al., "The lymphoid/neuronal OX-2 glycoprotein Interacts with a nove protein expressed by macrophages," Tissue Antigens, vol. 55(Suppl. 1):11, Poster Presentation A. 9 (2000).
Wright, Gavin J. et al., "Lymphoid/Neuronal Cell Surface OX2 Glycoprotein Recognizes a Novel Receptor on Macrophages Implicated in the Control of Their Function," Immunity, vol. 13:233-242 (2000).
Zhang, Shuli et al., "Molecular Mechanisms of CD200 Inhibition of Mast Cell Activation," The Journal of Immunology, vol. 173:6786-6793 (2004).
Wright, G. et al., "Characterization of the CD200 Receptor Family in Mice and Humans and Their Interactions with CD200," The Journal Immunology, vol. 171:3034-3046 (2003).
U.S. Appl. No. 16/954,562, filed Jun. 17, 2020, Taneisha Ann-Tanara Mack.
U.S. Appl. No. 13/521,671, filed Apr. 17, 2013, Susan Faas McKnight.
U.S. Appl. No. 14/827,693, filed Aug. 17, 2015, Susan Faas McKnight.
U.S. Appl. No. 13/983,415, filed Nov. 26, 2013, Yi Wang.
U.S. Appl. No. 14/739,862, filed Jun. 15, 2015, Russell P. Rother.
U.S. Appl. No. 13/578,367, filed Jan. 18, 2013, Russell P. Rother.
U.S. Appl. No. 12/452,772, filed Apr. 5, 2010, Yi Wang.
U.S. Appl. No. 14/080,457, filed Nov. 14, 2013, Russell P. Rother.
U.S. Appl. No. 13/533,546, filed Jun. 26, 2012, Russell P. Rother.
U.S. Appl. No. 12/670,379, filed Jul. 20, 2010, Russell P. Rother.
U.S. Appl. No. 12/087,683, filed Jan. 14, 2009, Katherine S. Bowdish.
U.S. Appl. No. 13/311,910, filed Dec. 6, 2011, Katherine S. Bowdish.
U.S. Appl. No. 13/771,911, filed Feb. 20, 2013, Katherine S. Bowdish.
U.S. Appl. No. 10/379,151, filed Mar. 4, 2003, Katherine S. Bowdish.
U.S. Appl. No. 10/433,207, filed May 30, 2003, Katherine S. Bowdish.
U.S. Appl. No. 12/286,759, filed Sep. 30, 2008, Katherine S. Bowdish.
U.S. Appl. No. 13/029,021, filed Feb. 16, 2011, Katherine S. Bowdish.
U.S. Appl. No. 10/736,188, filed Dec. 15, 2003, Katherine S. Bowdish.
U.S. Appl. No. 10/894,672, filed Jul. 20, 2004, Katherine S. Bowdish.
U.S. Appl. No. 12/221,134, filed Jul. 30, 2008, Katherine S. Bowdish.
U.S. Appl. No. 12/221,122, filed Jul. 30, 2008, Katherine S. Bowdish.
U.S. Appl. No. 12/715,303, filed Mar. 1, 2010, Katherine S. Bowdish.
U.S. Appl. No. 13/344,195, filed Jan. 5, 2012, Katherine S. Bowdish.
U.S. Appl. No. 10/996,316, filed Nov. 23, 2004, Katherine S. Bowdish.
U.S. Appl. No. 11/171,567, filed Jun. 30, 2005, Katherine S. Bowdish.
U.S. Appl. No. 11/985,322, filed Nov. 13, 2007, Katherine S. Bowdish.
U.S. Appl. No. 13/072,470, filed Mar. 25, 2011, Katherine S. Bowdish.
U.S. Appl. No. 14/630,262, filed Feb. 24, 2015, Katherine S. Bowdish.
U.S. Appl. No. 13/521,671, filed Jun. 23, 2020, I. Ouspenski.
U.S. Appl. No. 13/521,671, filed Mar. 11, 2015, I. Ouspenski.
U.S. Appl. No. 13/521,671, filed Nov. 10, 2014, J. Roarke,
U.S. Appl. No. 14/827,693, filed Apr. 3, 2018, L. Yao.
U.S. Appl. No. 14/827,693, filed Aug. 16, 2017, L. Yao.
U.S. Appl. No. 14/827,693, filed May 24, 2017, L. Yao.
U.S. Appl. No. 13/983,415, filed May 6, 2016, I. Ouspenski.
U.S. Appl. No. 13/983,415, filed Dec. 24, 2015, I. Ouspenski.
U.S. Appl. No. 13/983,415, filed Aug. 24, 2015, I. Ouspenski.
U.S. Appl. No. 13/983,415, filed May 22, 2015, I. Ouspenski.
U.S. Appl. No. 14/739,862, filed Nov. 1, 2017, I. Ouspenski.
U.S. Appl. No. 14/739,862, filed Sep. 25, 2017, I. Ouspenski.
U.S. Appl. No. 14/739,862, filed Jun. 7, 2017, I. Ouspenski.
U.S. Appl. No. 13/578,367, filed Jun. 11, 2015, I. Ouspenski.
U.S. Appl. No. 13/578,367, filed Mar. 5, 2015, I. Ouspenski.
U.S. Appl. No. 13/578,367, filed Jul. 7, 2014, I. Ouspenski.
U.S. Appl. No. 13/578,367, filed Feb. 20, 2014, I. Ouspenski.
U.S. Appl. No. 12/452,772, filed Nov. 12, 2014, J. Rogers.
U.S. Appl. No. 12/452,772, filed Mar. 13, 2014, J. Rogers.
U.S. Appl. No. 12/452,772, filed May 25, 2012, J. Rogers.
U.S. Appl. No. 12/452,772, filed Oct. 13, 2011, J. Rogers.
U.S. Appl. No. 12/452,772, filed Aug. 4, 2011, J. Rogers.
U.S. Appl. No. 12/670,379, filed Mar. 26, 2012, I. Ouspenski.
U.S. Appl. No. 12/670,379, filed Oct. 19, 2011, I. Ouspenski.
U.S. Appl. No. 12/670,379, filed Jul. 26, 2011, I. Ouspenski.
U.S. Appl. No. 13/533,546, filed Sep. 23, 2013, I. Ouspenski.
U.S. Appl. No. 13/533,546, filed May 2, 2013, I. Ouspenski.
U.S. Appl. No. 13/533,546, filed Mar. 14, 2013, I. Ouspenski.
U.S. Appl. No. 14/080,457, filed Oct. 14, 2016, B. Campell.
U.S. Appl. No. 12/087,683, filed Aug. 5, 2011, Ilia I. Ouspenski.
U.S. Appl. No. 12/087,683, filed May 24, 2011, Ilia I. Ouspenski.
U.S. Appl. No. 12/087,683, filed Jan. 4, 2011, Ilia I. Ouspenski.
U.S. Appl. No. 12/087,683, filed Sep. 23, 2010, Ilia I. Ouspenski.
U.S. Appl. No. 13/311,910, filed Dec. 13, 2013, Ilia I. Ouspenski.
U.S. Appl. No. 13/311,910, filed Jul. 1, 2013, Ilia I. Ouspenski.
U.S. Appl. No. 13/771,911, filed Oct. 23, 2014, Ilia I. Ouspenski.
U.S. Appl. No. 13/771,911, filed Jul. 18, 2014, Ilia I. Ouspenski.
U.S. Appl. No. 10/379,151, filed Jun. 4, 2008, Karen A. Canella.
U.S. Appl. No. 10/379,151, filed Mar. 19, 2008, Karen A. Canella.
U.S. Appl. No. 10/379,151, filed Sep. 24, 2007, Karen A. Canella.
U.S. Appl. No. 10/379,151, filed Mar. 28, 2007, Karen A. Canella.
U.S. Appl. No. 10/379,151, filed Jul. 13, 2006, Karen A. Canella.
U.S. Appl. No. 10/379,151, filed Mar. 27, 2006, Karen A. Canella.
U.S. Appl. No. 10/736,188, filed Apr. 3, 2008, Bradley Duffy.
U.S. Appl. No. 10/736,188, filed Jul. 30, 2007, Bradley Duffy.
U.S. Appl. No. 10/736,188, filed Jul. 26, 2006, Bradley Duffy.
U.S. Appl. No. 10/894,672, filed Sep. 18, 2015, Bradley Duffy.
U.S. Appl. No. 10/894,672, filed May 22, 2015, Bradley Duffy.
U.S. Appl. No. 10/894,672, filed Feb. 24, 2014, Bradley Duffy.
U.S. Appl. No. 10/894,672, filed Dec. 23, 2013, Bradley Duffy.
U.S. Appl. No. 10/894,672, filed Dec. 28, 2009, Bradley Duffy.
U.S. Appl. No. 10/894,672, filed May 12, 2009, Bradley Duffy.
U.S. Appl. No. 10/894,672, filed Oct. 15, 2008, Bradley Duffy.
U.S. Appl. No. 10/894,672, filed Mar. 19, 2008, Bradley Duffy.
U.S. Appl. No. 10/894,672, filed Nov. 7, 2007, Bradley Duffy.
U.S. Appl. No. 10/894,672, filed May 14, 2007, Bradley Duffy.
U.S. Appl. No. 10/894,672, filed Feb. 1, 2007, Bradley Duffy.
U.S. Appl. No. 12/221,134, filed May 29, 2009, Bradley Duffy.
U.S. Appl. No. 12/221,134, filed Feb. 25, 2009, Bradley Duffy.
U.S. Appl. No. 12/221,122, filed Dec. 1, 2009, Bradley Duffy.
U.S. Appl. No. 12/221,122, filed Jul. 24, 2009, Bradley Duffy.
U.S. Appl. No. 12/221,122, filed Apr. 30, 2009, Bradley Duffy.
U.S. Appl. No. 12/221,122, filed Jan. 23, 2009, Bradley Duffy.
U.S. Appl. No. 12/715,303, filed Oct. 26, 2011, Bradley Duffy.
U.S. Appl. No. 12/715,303, filed Jul. 11, 2011, Bradley Duffy.

(56) References Cited

OTHER PUBLICATIONS

U.S. Appl. No. 12/715,303, filed Nov. 8, 2010, Bradley Duffy.
U.S. Appl. No. 12/715,303, filed Jul. 22, 2010, Bradley Duffy.
U.S. Appl. No. 13/344,195, filed May 22, 2015, Bradley Duffy.
U.S. Appl. No. 13/344,195, filed Apr. 9, 2014, Bradley Duffy.
U.S. Appl. No. 13/344,195, filed Dec. 2, 2013, Bradley Duffy.
U.S. Appl. No. 13/344,195, filed Oct. 8, 2013, Bradley Duffy.
U.S. Appl. No. 10/996,316, filed May 28, 2008, Bradley Duffy.
U.S. Appl. No. 10/996,316, filed May 19, 2008, Bradley Duffy.
U.S. Appl. No. 10/996,316, filed May 12, 2008, Bradley Duffy.
U.S. Appl. No. 10/996,316, filed Feb. 8, 2008, Bradley Duffy.
U.S. Appl. No. 10/996,316, filed Nov. 7, 2007, Bradley Duffy.
U.S. Appl. No. 10/996,316, filed May 14, 2007, Bradley Duffy.
U.S. Appl. No. 10/996,316, filed Feb. 21, 2007, Bradley Duffy.
U.S. Appl. No. 11/171,567, filed May 14, 2007, Bradley Duffy.
U.S. Appl. No. 11/171,567, filed Feb. 14, 2007, Bradley Duffy.
U.S. Appl. No. 11/985,322, filed Nov. 30, 2010, Bradley Duffy.
U.S. Appl. No. 11/985,322, filed Jul. 30, 2010, Bradley Duffy.
U.S. Appl. No. 11/985,322, filed Oct. 5, 2009, Bradley Duffy.
U.S. Appl. No. 11/985,322, filed Jun. 11, 2009, Bradley Duffy.
U.S. Appl. No. 13/072,470, filed Nov. 25, 2014, Bradley Duffy.
U.S. Appl. No. 13/072,470, filed Jul. 17, 2014, Bradley Duffy.
U.S. Appl. No. 13/072,470, filed Feb. 28, 2014, Bradley Duffy.
U.S. Appl. No. 13/072,470, filed Jun. 22, 2012, Bradley Duffy.
U.S. Appl. No. 13/072,470, filed Jan. 27, 2012, Bradley Duffy.
U.S. Appl. No. 13/072,470, filed Sep. 8, 2011, Bradley Duffy.
U.S. Appl. No. 10/433,207, filed Mar. 25, 2008, Karen Canella.
U.S. Appl. No. 10/433,207, filed Oct. 31, 2007, Karen Canella.
U.S. Appl. No. 10/433,207, filed May 2, 2007, Karen Canella.
U.S. Appl. No. 10/433,207, filed Jul. 12, 2006, Karen Canella.
U.S. Appl. No. 10/433,207, filed Mar. 29, 2006, Karen Canella.
U.S. Appl. No. 12/286,759, filed Feb. 21, 2012, Karen Canella.
U.S. Appl. No. 12/286,759, filed Oct. 21, 2011, Karen Canella.
U.S. Appl. No. 12/286,759, filed May 20, 2011, Karen Canella.
U.S. Appl. No. 13/029,021, filed May 14, 2014, Karen Canella.
U.S. Appl. No. 13/029,021, filed Nov. 21, 2013, Karen Canella.
U.S. Appl. No. 13/029,021, filed Jul. 20, 2012, Karen Canella.
U.S. Appl. No. 13/029,021, filed Feb. 16, 2012, Karen Canella.
U.S. Appl. No. 14/630,262, filed May 19, 2016, Bradley Duffy.
Almasri, Nidal M. et al., "Reduced Expression of CD20 Antigen as a Characteristic Marker for Chronic Lymphocytic Leukemia," American Journal of Hematology, vol. 40:259-263 (1992).
Banerjee, Debatri et al., "Blocking CD200-CD200 receptor axis augments NOS-2 expression and aggravates experimental autoimmune uveoretinitis in Lewis rats," Ocular Immunology and Inflammation, vol. 12(2):115-125 (2004).
Barclay, A. Neil et al., "CD200 and membrane protein interactions in the control of myeloid cells," Trends in Immunology, vol. 23(6):285-290 (2002).
Bello, Celeste et al., "Monoclonal Antibodies for B-Cell Lymphomas: Rituximab and Beyond," Hematology, pp. 233-242 (2007).
Borriello, Frank et al., "Mrc OX-2 Defines a Novel T Cell Costimulatory Pathway," The Journal of Immunology, vol. 158:4548-4554 (1997).
Broderick, Cathryn et al., "Constitutive Retinal CD200 Expression Regulates Resident Microglia and Activation State of Inflammatory Cells during Experimental Autoimmune Uveoretinitis," American Journal of Pathology, vol. 161 (5):1669-1677 (2002).
Burge, Daniel J. et al., "Pharmacokinetic and Pharmacodynamic Properties of TRU-015, a CD20-Directed Small Modular Immunopharmaceutical Protein Therpeutic, in Patients with Rheumatoid Arthritis: A Phase I, Open-Label, Dose-Escalation ClinicalStudy," Clinical Therapeutics, vol. 30(10):1806-1816 (2008).
Chen, Dang-Xiao et al., "Synthetic peptides from the N-terminal regions of CD200 and CD200R1 modulate immunosuppressive and anti-inflammatory effects of CD200-CD200R1 interaction," International Immunology, vol. 17(3):289-296 (2005).
Chen, Z. et al., "Cloning and characterization of the murine homologue of the rat/human MRC OX-2 gene," Biochimica et Biophysica Acta, vol. 1362:6-10 (1997).

Cheng, Dang-Xiao et al., "Discrete Monoclonal Antibodies Define Functionally Important Epitopes in the CD200 Molecule Responsible for Immunosuppression Function," Transplantation, vol. 79:282-288 (2005).
Cherwinski, Holly M. et al., "The CD200 Receptor Is a Novel and Potent Regulator of Murine and Human Mast Cell Function," The Journal of Immunology, vol. 174:1348-1356 (2005).
Chi, E. et al., "Physical stability of proteins in aqueous solution: mechanism and driving forces in nonnative protein aggregation," Pharmaceutical Research, vol. 20:1325-1336 (2003).
Cui, Weiguo et al., "CD200 and its receptor, CD200R, modulate bone mass via the differentiation of osteoclasts," PNAS, vol. 104(36):14436-14441 (2007).
Ebert, Ellen C. et al., "Selective Immunosuppressive Action of a Factor Produced by Colon Cancer Cells," Cancer Research, vol. 50:6158-6161 (1990).
Ennishi, D. et al., "CD5 expression is potentially predictive of poor outcome among biomarkers in patients with diffuse large B-cell lymphoma receiving rituximab plus Chop therapy," Annals of Oncology, vol. 19:1921-1926 (2008).
Fallarino, Francesca et al., "Murine Plasmacytoid Dendritic Cells Initiate the Immunosuppressive Pathway of Tryptophan Catabolismin Response to CD200 Receptor Engagement," The Journal of Immunology, vol. 173:3748-3754 (2004).
Frediberg, Jonathan W., "Unique Toxicities and Resistance Mechanisms Associated with Monoclonal Antibody Therapy," Hematology, pp. 329-334 (2005).
Gorczynski, Laura et al., "Evidence That an Ox-2-Positive Cell Can Inhibit the Stimulation of Type 1 Cytokine Production by Bone Marrow-Derived B7-1 (and B7-2)-Positive Dendritic Cells," The Journal of Immunology, vol. 162:774-781 (1999).
Gorczynski, R. et al., "An immunoadhesin incorporating the molecule OX-2 is a potent immunosuppressant which prolongs allograft survival," FASEB Journal, vol. 13(5):A983, Poster Presentation 712.35 (1999).
Gorczynski, R. et al., "Breast Cancer Cell CD200 Expression Regulates Immune Response to EMT6 Tumor Cells in Mice," Breast Cancer Research and Treatment, vol. 123(2): 405-415 (2009).
Gorczynski, R. et al., "Dendritic Cells Expressing TGFbeta/IL-10, and Cho Cells With OX-2, Increase Graft Survival," Transplantation Proceedings, vol. 33:1585-1566 (2001).
Gorczynski, R.M. et al., "A CD200FC Immunoadhesin Prolongs Rat Islet Xenograft Survival in Mice," Transplantation, vol. 73(12):1948-1953 (2002).
Gorczynski, R.M. et al., "Anti-Rat OX-2 Blocks Increased Small Intestinal Transplant Survival After Portal Vein Immunization," Transplantation Proceedings, vol. 31:577-578 (1999).
Gorczynski, R.M. et al., "Evidence for Persistent Expression of OX2 as a Necessary Component of Prolonged Renal Allograft Survival Following Portal Vein Immunization," Clinical Immunology, vol. 97(1):69-78 (2000).
Gorczynski, R.M. et al., "Evidence of a role for CD200 in regulation of immune rejection of leukaemic tumour cells in C57BL/6 mice," Clin. Exp. Immunol., vol. 126:220-229 (2001).
Gorczynski, R.M. et al., "Persistent expression of OX-2 is necessary for renal allograft survival," FASEB Journal, vol. 14(6):A1069, Poster Presentation No. 102.4 (2000).
Gorczynski, R.M. et al., "Structural and Functional Heterogeneity in the CD200R Family of Immoregulatory Molecules and their Expression at the Feto-maternal Interface," American Journal of Reproeuctive Immunology, vol. 52:147-163 (2004).
Gorczynski, R.M. et al., "Synergy in Induction of Increased Renal Allograft Survival after Portal Vein Infusion of Dendritic Cells Transduced to Expression TGFbeta and IL-10, along with Administration of Cho Cells Expressing the Regulatory MoleculeOX-2," Clinical Immunology, vol. 95(3):182-189 (2000).
Gorczynski, Reg M., "Evidence for an Immunoregulatory Role of OX2 with Its Counter Ligand (OX2L) in the Regulation of Transplant Rejection, Fetal Loss, Autoimmunity and Tumor Growth," Archivum Immunologiae et Therapiae Experimentalis, vol. 49:303-309 (2001).

(56) References Cited

OTHER PUBLICATIONS

Gorczynski, Reginald et al., "CD200 Is a Ligand for All Members of the CD200R Family of Immunoregulatory Molecules," the Journal of Immunology, vol. 172:7744-7749 (2004).
Gorczynski, Reginald M. et al., "An Immunoadhesin Incorporating the Molecule OX-2 Is a Potent Immunosuppressant That Prolongs Allo-and Xenograft Survival," The Journal of Immunology, vol. 163:1654-1660 (1999).
Gorczynski, Reginald M. et al., "Anti-CD200R Ameliorates Collagen-Induced Arthritis in Mice," Clinical Immunology, vol. 104(3):256-264 (2002).
Gorczynski, Reginald M. et al., "Augmented Induction of CD4+ CD25+ Treg using Monoclonal Antibodies to CD200R," Transplantation, vol. 79:1180-1183 (2005).
Gorczynski, Reginald M. et al., "CD200 Immunoadhesin Suppresses Collagen-Induced Arthritis in Mice," Clinical Immunology, vol. 101(3):328-334 (2001).
Gorczynski, Reginald M. et al., "Increased Expression of the Novel Molecule OX-2 is Involved in Prolongation of Murine Renal Allograft Survival," Transplantation, vol. 65(8):1106-1114 (1998).
Gorczynski, Reginald M. et al., "Induction of Tolerance-Inducing Antigen-Presenting Cells in Bone Marrow Cultures in Vitro Using Monoclonal Antibodies to CD200R," Transplantation, vol. 77(8):1138-1144 (2004).
Gorczynski, Reginald M. et al., "Receptor Engagement on Cells Expressing a Ligand for the Tolerance-Inducing Molecule OX2 Induces an Immunoregulatory Population That Inhibits Alloreactivity in Vitro and in Vivo," The Journal of Immunology, vol. 165:4845-4860 (2000).
Gorczynski, Reginald M., "CD200 and its receptors as targets for immunoregulation," Current Opinion in Investigational Drugs, vol. 6(5):483-488 (2005).
Gorczynski, Reginald M., "Transplant tolerance modifying antibody to CD200 receptor, but not CD200, alters cytokine production profile from stimulated macrophages," Eur. J. Immunol., vol. 31:2331-2337 (2001).
Hatherley, Deborah et al., "The CD200 and CD200 receptor cell surface proteins interact through their N-terminal immunoglobulin-like domains," Eur. J. Immunol., vol. 34:1688-1694 (2004).
Hernandez-Ilizaliturri, F.J. et al., "Strategies to overcoming rituximab-chemotherapy resistance by targeting the autophagy pathway using bortezomib in combination with the BCL-2 inhibitor obatoclax in non-Hodgkin's lymphomas (NHL)," Journal of Clinical Oncology, 2009 ASCO Annual Meeting Proceedings, vol. 27(15S), Poster Presentation No. 8543, 1 page (2009).
Hoek, R.M., et al., "Macrophage regulation by the B7.1/2 homologue OX2?" FASEB Journal, vol. 14(6):A1232, Poster Presentation No. 193.1 (2000).
Hoek, Robert M., "Down-Regulation of the Macrophage Lineage Through Interaction with OX2 (CD200)," Science, vol. 290(5497):1768-1771 (2000).
Holodick, Nichol E. et al., "Adult Bm generates CD5+ B1 cells containing abundant N-region additions," Eur. J. Immunol., vol. 39(9):2383-2394 (2009).
Hutchings, N.J. et al., "Interactions of Cytoplasmic Region of OX2R are Consistent wtih an Inhibitory Function," Annual Congress of the British Society for Immunology, vol. 101(Suppl. 1), Poster Presentation No. 10.6, 1 page (2000).
International Preliminary Report on Patentability, PCT/US2018/066174, dated Jun. 23, 2020, 14 pages.
International Preliminary Report on Patentability. PCT/US2018/066855, dated Jun. 23, 2020, 8 pages.
International Search Report and Written Opinion, PCT/US2018/066174, dated Jun. 4, 2019, 22 pages.
International Search Report and Written Opinion. PCT/US2018/066855, dated Mar. 27, 2019, 12 pages.
Jorgensen, G. et al., "Recent trends in stabilising peptides and proteins in pharmaceutical formulation considerations in the choice of excipients," Expert Opinion on Drug Delivery, vol. 6 (11):66-108 (2009).
Shao, A. et al., "The immunoregulatory protein CD200 as a potentially lucrative yet elusive target for cancer therapy," Oncotarget, vol. 14:96-103 (2023).
Study of Samalizumab in Patients With Advanced Cancer, ClinicalTrials.gov, 7 pages (2018).
Akbar, R. et al., "A compact vocabulary of paratope-epitope interactions enables predictability of antibodyantigen binding," Cell Reports, vol. 34, 108856, 21 pages (2021).
Burd , A. et al., Precision medicine treatment in acute myeloid leukemia using prospective genomic profiling: feasibility and preliminary efficacy of the Beat AML Master Trial, Nat Med., vol. 26(12): 1852-1858 (2020).
Lo, Y-T, et al., "Conformational epitope matching and prediction based on protein surface spiral features," BMC Genomics, vol. 22, Article No. 116, 16 pages (2021).
MacCallum, R.M, et al., Antibody-antigen interactions: contact analysis and binding site topography,: J. Mol. Biol., vol. 262:732-745 (1996).
Marks, C. et al., "How repertoire data are changing antibody science," J. Biol. Chem. 295(29) 9823-9837 (2020).
Mehadevan, D. et al., "Phase I study of samalizumab in chronic lymphocytic leukemia and multiple myeloma: blockade of the immune checkpoint CD200," Journal for ImmunoTherapy of Cancer, vol. 7(1):227 (2019).
Vajda, S. et al., "Progress toward improved understanding of antibody maturation," Current Opinion in Structural Biology, vol. 67: 226-231 (2021).
Vajdos, F. et al., "Comprehensive functional maps of the antigen-binding site of an anti-ErbB2 antibody obtained with shotgun scanning mutagenesis," J. Mol. Biol. , vol. 320: 415-428 (2002).
Wu, H. et al., "Humanization of a murine monoclonal antibody by simultaneous optimization of framework and CDR residues," (J. Mol. Biol., vol. 294: 151-162 (1999).

\* cited by examiner

Appearance Analysis:

| Sample # | NaCl (mM) | Conc. (mg/mL) | pH | Mannitol (%) | T=0 | 1M | 2M | 3M | 6M | 9M | 11M | 12M | 15M | 18M | 24M |
|---|---|---|---|---|---|---|---|---|---|---|---|---|---|---|---|
| 1 | 150 | 5 | 5.75 | 0 | CC | CC | CC | CC | CC | CC | CC | CC | CC | CC | CC |
| 2 | 150 | 5 | 5.75 | 1 | CC | CC | CC | CC | CC | CC | CC | CC | CC | CC | CC |
| 3 | 150 | 5 | 5.75 | 3 | CC | CC | CC | CC | CC | CC | CC | CC | CC | CC | CC |
| 4 | 150 | 5 | 5.50 | 0 | CC | CC | CC | CC | CC | CC | CC | CC | CC | CC | CC |
| 5 | 150 | 5 | 5.50 | 1 | CC | CC | CC | CC | CC | CC | CC | CC | CC | CC | CC |
| 6 | 150 | 5 | 5.50 | 3 | CC | CC | CC | CC | CC | CC | CC | CC | Precip. | Precip. | Precip. |
| 7 | 150 | 5 | 5.25 | 0 | CC | CC | CC | CC | CC | CC | CC | Precip. | Precip. | Precip. | Precip. |
| 8 | 150 | 5 | 5.25 | 1 | CC | CC | CC | CC | CC | CC | CC | CC | CC | CC | CC |
| 9 | 150 | 5 | 5.25 | 3 | CC | CC | CC | CC | CC | CC | CC | CC | CC | CC | CC |
| 10 | 150 | 5 | 5.00 | 0 | CC | CC | CC | CC | CC | CC | CC | CC | CC | CC | CC |
| 11 | 150 | 5 | 5.00 | 1 | CC | CC | CC | CC | CC | CC | CC | CC | CC | CC | CC |
| 12 | 150 | 5 | 5.00 | 3 | CC | CC | CC | Precip. | CC | CC | CC | CC | CC | CC | CC |
| 13 | 150 | 10 | 5.75 | 0 | CC | CC | CC | CC | CC | Precip. | Precip. | Precip. | Precip. | Precip. | Precip. |
| 14 | 150 | 10 | 5.75 | 1 | CC | CC | CC | CC | CC | Precip. | Precip. | Precip. | Precip. | Precip. | Precip. |
| 15 | 150 | 10 | 5.75 | 3 | CC | CC | CC | CC | CC | CC | Precip. | Precip. | Precip. | Precip. | Precip. |
| 16 | 150 | 10 | 5.50 | 0 | CC | CC | CC | CC | CC | CC | Precip. | Precip. | Precip. | Precip. | Precip. |
| 17 | 150 | 10 | 5.50 | 1 | CC | CC | CC | CC | CC | CC | Precip. | Precip. | Precip. | Precip. | Precip. |
| 18 | 150 | 10 | 5.50 | 3 | CC | CC | CC | CC | CC | CC | CC | Precip. | Precip. | Precip. | Precip. |
| 19 | 150 | 10 | 5.25 | 0 | CC | CC | CC | CC | CC | CC | Precip. | Precip. | Precip. | Precip. | Precip. |
| 20 | 150 | 10 | 5.25 | 1 | CC | CC | CC | CC | CC | CC | CC | CC | CC | CC | CC |
| 21 | 150 | 10 | 5.25 | 3 | CC | CC | CC | CC | CC | CC | CC | CC | CC | CC | CC |
| 22 | 150 | 10 | 5.00 | 0 | CC | CC | CC | CC | CC | CC | CC | CC | CC | CC | CC |
| 23 | 150 | 10 | 5.00 | 1 | CC | CC | CC | CC | CC | CC | CC | CC | CC | CC | CC |
| 24 | 150 | 10 | 5.00 | 3 | CC | CC | CC | CC | CC | CC | CC | CC | CC | CC | CC |

*FIG. 2*

Appearance Analysis:

| Sample # | NaCl (mM) | Conc. (mg/mL) | pH | Mannitol (%) | T=0 | 1M | 2M | 3M | 6M | 9M | 11M | 12M | 15M | 18M | 24M |
|---|---|---|---|---|---|---|---|---|---|---|---|---|---|---|---|
| 25 | 75 | 5 | 5.75 | 0 | CC | CC | CC | CC | CC | CC | Precip. | Precip. | Precip. | Precip. | Precip. |
| 26 | 75 | 5 | 5.75 | 1 | CC | CC | CC | CC | CC | CC | CC | Precip. | Precip. | Precip. | Precip. |
| 27 | 75 | 5 | 5.75 | 3 | CC | CC | CC | CC | CC | CC | CC | CC | CC | CC | CC |
| 28 | 75 | 5 | 5.50 | 0 | CC | CC | CC | CC | CC | CC | CC | CC | CC | CC | CC |
| 29 | 75 | 5 | 5.50 | 1 | CC | CC | CC | CC | CC | CC | CC | CC | CC | CC | CC |
| 30 | 75 | 5 | 5.50 | 3 | CC | CC | CC | CC | CC | CC | CC | CC | CC | Precip. | Precip. |
| 31 | 75 | 5 | 5.25 | 0 | CC | CC | CC | CC | CC | CC | CC | CC | CC | CC | CC |
| 32 | 75 | 5 | 5.25 | 1 | CC | CC | CC | CC | CC | CC | CC | CC | CC | CC | CC |
| 33 | 75 | 5 | 5.25 | 3 | CC | CC | CC | CC | CC | CC | CC | CC | CC | CC | CC |
| 34 | 75 | 5 | 5.00 | 0 | CC | CC | CC | CC | CC | CC | CC | CC | CC | CC | CC |
| 35 | 75 | 5 | 5.00 | 1 | CC | CC | CC | CC | CC | CC | CC | CC | CC | CC | CC |
| 36 | 75 | 5 | 5.00 | 3 | CC | CC | CC | Precip. | Precip. | Precip. | Precip. | Precip. | Precip. | Precip. | Precip. |
| 37 | 75 | 10 | 5.75 | 0 | CC | CC | CC | CC | Precip. | Precip. | Precip. | Precip. | Precip. | Precip. | Precip. |
| 38 | 75 | 10 | 5.75 | 1 | CC | CC | CC | CC | CC | Precip. | CC | Precip. | CC | Precip. | Precip. |
| 39 | 75 | 10 | 5.75 | 3 | CC | CC | CC | CC | Precip. | CC | CC | Precip. | CC | Precip. | Precip. |
| 40 | 75 | 10 | 5.50 | 0 | CC | CC | CC | CC | CC | CC | Precip. | Precip. | Precip. | Precip. | Precip. |
| 41 | 75 | 10 | 5.50 | 1 | CC | CC | CC | CC | CC | CC | CC | Precip. | Precip. | Precip. | Precip. |
| 42 | 75 | 10 | 5.50 | 3 | CC | CC | CC | CC | CC | CC | CC | CC | Precip. | Precip. | Precip. |
| 43 | 75 | 10 | 5.25 | 0 | CC | CC | CC | CC | CC | CC | Precip. | Precip. | Precip. | Precip. | Precip. |
| 44 | 75 | 10 | 5.25 | 1 | CC | CC | CC | CC | CC | CC | CC | CC | Precip. | Precip. | Precip. |
| 45 | 75 | 10 | 5.25 | 3 | CC | CC | CC | CC | CC | CC | CC | CC | Precip. | Precip. | Precip. |
| 46 | 75 | 10 | 5.00 | 0 | CC | CC | CC | CC | CC | CC | CC | CC | CC | CC | CC |
| 47 | 75 | 10 | 5.00 | 1 | CC | CC | CC | CC | CC | CC | CC | CC | CC | CC | CC |
| 48 | 75 | 10 | 5.00 | 3 | CC | CC | CC | CC | CC | CC | CC | CC | CC | CC | CC |

*FIG. 2 – cont'd*

SEC-HPLC results:

| Sample ID | NaCl (mM) | Concentration (mg/mL) | pH | Mannitol (%) | T=0 | T=1M | T=2M | T=3M | T=6M | T=9M | T=12M | T=15M | T=18M | T=24M |
|---|---|---|---|---|---|---|---|---|---|---|---|---|---|---|
| 1 | 150 | 5 | 5.75 | 0 | 99.1 | 99.1 | 98.9 | 99.1 | 99 | 98.8 | 98.9 | 98.6 | N/A | N/A |
| 2 | 150 | 5 | 5.75 | 1 | 99.1 | 99 | 98.9 | 99 | 98.9 | 98.7 | 98.9 | 98.8 | N/A | N/A |
| 3 | 150 | 5 | 5.75 | 3 | 99.1 | 99 | 98.9 | 99 | 98.9 | 98.7 | 98.9 | 98.8 | N/A | N/A |
| 4 | 150 | 5 | 5.5 | 0 | 99.1 | 99 | 98.9 | 99 | 99 | 98.8 | 98.9 | 98.8 | N/A | N/A |
| 5 | 150 | 5 | 5.5 | 1 | 99 | 99 | 98.9 | 99 | 98.9 | 98.8 | 98.9 | 98.8 | N/A | N/A |
| 6 | 150 | 5 | 5.5 | 3 | 99 | 99 | 98.9 | 99 | 98.9 | 98.8 | 98.9 | 98.8 | N/A Prec | N/A Prec |
| 7 | 150 | 5 | 5.25 | 0 | 99.1 | 99 | 98.8 | 99 | 99 | 98.8 | 98.9 | N/A Prec | N/A Prec | N/A Prec |
| 8 | 150 | 5 | 5.25 | 1 | 99 | 99 | 98.8 | 99 | 98.9 | 98.7 | 98.8 | 98.7 | N/A | N/A |
| 9 | 150 | 5 | 5.25 | 3 | 99 | 99 | 98.9 | 99 | 98.9 | 98.7 | 98.8 | 98.8 | N/A | N/A |
| 10 | 150 | 5 | 5 | 0 | 99 | 99 | 98.9 | 99 | 98.9 | 98.8 | 98.9 | 98.8 | N/A | N/A |
| 11 | 150 | 5 | 5 | 1 | 99 | 98.9 | 98.9 | 99 | 98.9 | 98.8 | 98.6 | 98.7 | N/A | N/A |
| 12 | 150 | 5 | 5 | 3 | 99 | 98.9 | 98.9 | 99 | 98.9 | 98.8 | 98.8 | 98.7 | N/A | N/A |
| 13 | 150 | 10 | 5.75 | 0 | 99 | 98.9 | 98.8 | 99.0* | N/A Prec | N/A Prec | N/A Prec | N/A Prec | N/A Prec | N/A Prec |
| 14 | 150 | 10 | 5.75 | 1 | 99 | 99 | 98.8 | 98.9 | 98.9 | N/A Prec | N/A Prec | N/A Prec | N/A Prec | N/A Prec |
| 15 | 150 | 10 | 5.75 | 3 | 99 | 98.9 | 98.8 | 98.9 | 98.8 | 98.7 | 98.8 | 98.7 | N/A | N/A |
| 16 | 150 | 10 | 5.5 | 0 | 99 | 99 | 98.8 | 99 | 98.9 | 98.7 | N/A Prec | N/A Prec | N/A Prec | N/A Prec |
| 17 | 150 | 10 | 5.5 | 1 | 99 | 98.9 | 98.8 | 99 | 98.8 | 98.8 | N/A Prec | N/A Prec | N/A Prec | N/A Prec |
| 18 | 150 | 10 | 5.5 | 3 | 99 | 98.9 | 98.8 | 99 | 98.9 | 98.8 | 98.8 | N/A Prec | N/A Prec | N/A Prec |
| 19 | 150 | 10 | 5.25 | 0 | 99 | 99 | 98.8 | 99 | 98.8 | 98.8 | 98.8 | 98.7 | N/A | N/A |
| 20 | 150 | 10 | 5.25 | 1 | 99 | 98.9 | 98.8 | 98.9 | 98.9 | 98.7 | 98.8 | 98.7 | N/A Prec | N/A Prec |
| 21 | 150 | 10 | 5.25 | 3 | 99 | 98.9 | 98.9 | 98.9 | 98.9 | 98.7 | 98.7 | 98.7 | N/A | N/A |
| 22 | 150 | 10 | 5 | 0 | 99 | 98.9 | 98.8 | 98.9 | 98.9 | 98.8 | 98.7 | 98.2 | N/A | N/A |
| 23 | 150 | 10 | 5 | 1 | 99 | 98.9 | 98.8 | 98.9 | 98.9 | 98.8 | 98.7 | 98.2 | N/A | N/A |
| 24 | 150 | 10 | 5 | 3 | 99 | 98.9 | 98.8 | 98.9 | 98.9 | 98.8 | 98.7 | 98.4 | N/A | N/A |

*Sample was centrifuged prior to analysis

FIG. 3

| Sample ID | NaCl (mM) | Concentration (mg/mL) | pH | Mannitol (%) | T=0 | T=1M | T=2M | T=3M | T=6M | T=9M | T=12M | T=15M | T=18M | T=24M |
|---|---|---|---|---|---|---|---|---|---|---|---|---|---|---|
| 25 | 75 | 5 | 5.75 | 0 | 99 | 98.9 | 98.9 | 98.9 | 98.9 | 98.8 | N/A Prec | N/A Prec | N/A Prec | N/A Prec |
| 26 | 75 | 5 | 5.75 | 1 | 99 | 98.9 | 98.8 | 98.9 | 98.9 | 98.8 | 98.9 | N/A Prec | N/A Prec | N/A Prec |
| 27 | 75 | 5 | 5.75 | 3 | 98.9 | 98.9 | 98.8 | 98.9 | 98.8 | 98.8 | 98.8 | 98.8 | N/A | N/A |
| 28 | 75 | 5 | 5.5 | 0 | 99 | 98.9 | 98 | 98.9 | 98.9 | 98.8 | 98.8 | 98.6 | 98.8 | 98.6 |
| 29 | 75 | 5 | 5.5 | 1 | 99 | 98.9 | 98.8 | 98.9 | 98.9 | 98.8 | 98.8 | 98.8 | 98.8 | 98.7 |
| 30 | 75 | 5 | 5.5 | 3 | 99 | 98.9 | 98.9 | 98.9 | 98.9 | 98.8 | 98.7 | 98.7 | N/A | N/A |
| 31 | 75 | 5 | 5.25 | 0 | 99 | 98.9 | 98.8 | 98.9 | 98.9 | 98.8 | 98.7 | 98.8 | N/A Prec | N/A Prec |
| 32 | 75 | 5 | 5.25 | 1 | 99 | 98.9 | 98.9 | 98.9 | 98.9 | 98.7 | 98.8 | 98.8 | 98.8 | 98.7 |
| 33 | 75 | 5 | 5.25 | 3 | 98.9 | 98.9 | 98.8 | 98.9 | 98.8 | 98.8 | 98.8 | 98.8 | 98.8 | 98.7 |
| 34 | 75 | 5 | 5 | 0 | 99 | 98.9 | 100 | 98.9 | 98.9 | 98.7 | 98.7 | 98.7 | N/A | N/A |
| 35 | 75 | 5 | 5 | 1 | 99 | 98.9 | 98.9 | 98.9 | 98.9 | 98.8 | 98.7 | 98.7 | 98.7 | 100 |
| 36 | 75 | 5 | 5 | 3 | 98.9 | 98.9 | 98.8 | 98.9 | 98.9 | 98.8 | 98.8 | 98.7 | 98.7 | 98.6 |
| 37 | 75 | 10 | 5.75 | 0 | 99 | 98.9 | 98.8 | 98.9* | N/A Prec | N/A Prec | N/A Prec | N/A Prec | N/A Prec | N/A Prec |
| 38 | 75 | 10 | 5.75 | 1 | 98.9 | 98.9 | 98.8 | 98.9 | N/A Prec | N/A Prec | 98.8 | N/A Prec | N/A Prec | N/A Prec |
| 39 | 75 | 10 | 5.75 | 3 | 98.9 | 98.9 | 98.8 | 98.8 | 98.8 | 98.7 | 98.8 | 98.7 | N/A Prec | N/A Prec |
| 40 | 75 | 10 | 5.5 | 0 | 98.9 | 98.9 | 98.8 | 98.9 | N/A Prec | N/A Prec | N/A Prec | N/A Prec | N/A Prec | N/A Prec |
| 41 | 75 | 10 | 5.5 | 1 | 98.9 | 98.8 | 98.8 | 98.9 | 98.8 | 98.8 | 98.8 | 98.8 | N/A Prec | N/A Prec |
| 42 | 75 | 10 | 5.5 | 3 | 98.9 | 98.9 | 98.9 | 98.8 | 98.9 | 98.9 | 98.8 | 98.6 | 98.7 | N/A Prec |
| 43 | 75 | 10 | 5.25 | 0 | 98.9 | 98.8 | 98.8 | 98.9 | 98.9 | 98.8 | 98.8 | 98.7 | 98.7 | N/A Prec |
| 44 | 75 | 10 | 5.25 | 1 | 98.9 | 98.8 | 98.8 | 98.8 | 98.8 | 98.9 | 98.7 | 98.7 | 98.7 | 98.6 |
| 45 | 75 | 10 | 5.25 | 3 | 98.9 | 98.8 | 98.8 | 98.8 | 98.8 | 98.8 | 98.8 | 98.8 | 98.8 | 98.6 |
| 46 | 75 | 10 | 5 | 0 | 98.9 | 98.9 | 98.8 | 98.8 | 98.9 | 98.8 | N/A Prec | N/A Prec | N/A Prec | N/A Prec |
| 47 | 75 | 10 | 5 | 1 | 98.9 | 98.9 | 98.8 | 98.8 | 98.9 | 98.8 | 98.7 | 98.2 | 98.7 | 97.4 |
| 48 | 75 | 10 | 5 | 3 | 98.9 | 98.83 | 98.8 | 98.9 | 98.9 | 98.8 | 98.7 | 98.2 | 98.7 | 97.6 |

*Sample was centrifuged prior to analysis

FIG. 3 – cont'd

LIQUID FORMULATIONS OF ANTI-CD200 ANTIBODIES

CROSS-REFERENCE TO RELATED APPLICATIONS

This application is a 35 U.S.C. 371 national stage filing of International Application No. PCT/US2018/066174, filed Dec. 18, 2018, which claims priority to U.S. Provisional Application 62/608,322, filed Dec. 20, 2017. The contents of the aforementioned applications are hereby incorporated by reference in their entirety.

SEQUENCE LISTING

The instant application contains a Sequence Listing which has been submitted in ASCII format via EFS-Web, and is hereby incorporated by reference in its entirety. Said ASCII copy, created on Jun. 17, 2020, is named AXJ_215US.txt and is 48,223 bytes in size.

TECHNICAL FIELD

The field of the invention relates to liquid pharmaceutical formulations comprising at least one antibody that binds to CD200, a process for the preparation the pharmaceutical formulations, and methods of use thereof.

BACKGROUND

Antibody-based therapeutics has found a prominent place in the biopharmaceutical industry, and have contributed significantly to advancing treatment in multiple disease areas, including inflammatory and autoimmune diseases and cancer. A number of antibody products have been approved by the Federal Drug Administration in recent years. However, while liquid formulations are generally preferred, antibodies are only marginally stable in liquid formulations and are prone to physical and chemical degradation. Relatively small changes of external variables (e.g., temperature, pH, light exposure) can destabilize the protein structure leading to denaturation, aggregation, and precipitation (Chi et al., *Pharmaceutical Research* 20:1325-1336, 2003). Accordingly, the production of liquid antibody formulations which retain physical and chemical stability during storage and shipping at a regulated temperature (e.g., refrigerated at 2-8° C.) remains a major challenge.

Anti-CD200 targeted therapy has been proposed as an immunotherapeutic treatment for cancer, autoimmune disorders, and for prolonging allograft survival (e.g., U.S. Pat. Nos. 7,408,041 and 9,085,623; and U.S. Pat. Pub. No. 2014/0170143). For example, in an animal model of CLL, anti-CD200 antibody administration resulted in nearly complete tumor growth inhibition (Kretz-Rommel et al., *J. Immunol.* 178:5595-5605, 2007). CD200 knockout animal studies, as well as experiments using antagonist anti-CD200 antibodies and recombinant CD200-Fe fusion proteins have also demonstrated that CD200 is an immunosuppressive agent in autoimmune disorders and during transplantation (e.g., Hoek et al., Science 290:1768-1771, 2000; Gorczynski et al., *J Immunol.* 163:1654-1.660, 1999).

In early clinical trials for or adult patients with advanced stage B-cell chronic lymphocytic leukemia (B-CLL) or multiple myeloma (MM), samalizumab (ALXN6000), a humanized, anti-human CD200 antibody, was well tolerated at all doses studied, exhibited a dose-dependent biological and pharmacokinetic response, and exhibited initial evidence of anti-tumor activity (Mahadevan et al., 52nd American Society of Hematology (ASH) Annual Meeting and Exposition, Abstract 2465, 2010).

However, initial pharmaceutical formulations of samalizumab were limited to 5 mg/mL or less and had stability issues when stored at 4° C., with a propensity to aggregate. The drug concentration thus limited the maximum dose, weight/size of the patient and route of administration.

Accordingly, there is a need for improved liquid formulations containing anti-human CD200 antibodies, which are stable under standard storage and shipping conditions (e.g., 2-8° C.), and/or have higher concentrations, and which are suitable for administration to patients, for example, by intravenous and/or subcutaneous injection.

SUMMARY

Provided herein are liquid pharmaceutical formulations comprising at least one anti-CD200 antibody, or antigen binding fragment thereof, in an amount suitable for therapeutic use that is stable at 2-8° C. for an extended period of time (e.g., at least 9, 12, 15, 18, 21, or 24 months).

Accordingly, in one aspect, provided herein is a liquid formulation comprising (a) at least one anti-CD200 antibody, or antigen binding fragment thereof, (b) a non-ionic surfactant, (c) a polyol, and (d) a citrate buffer at a pH of about 5.0 to about 5.5, wherein the formulation is stable at 2-8° C. for at least about 9 months.

In certain embodiments of the this first aspect, the concentration of the anti-CD200 antibody or antigen binding fragment thereof in the formulation is between about 2 mg/mL and about 20 mg/mL, or between about 5 mg/mL and about 10 mg/mL.

In certain embodiments of the first aspect, the polyol in the liquid pharmaceutical formulation is a sugar alcohol, for example, mannitol, and is present at a concentration of at least 1.0% (w/v); or between about 1.0% and about 5% (w/v).

In certain embodiments of this first aspect, the non-ionic surfactant in the liquid pharmaceutical formulation is a polysorbate (e.g., Polysorbate 20, Polysorbate 40, Polysorbate 60, Polysorbate 80 or a combination of one or more thereof), and is present at a concentration between about 0.001% and 1.0% (w/v). In certain embodiments, the polysorbate is present at a concentration of between about 0.01% and 0.1% (w/v). In certain embodiments, the non-ionic surfactant is Polysorbate 80 at a concentration between about 0.01% and 0.04% (w/v). In certain embodiments, the non-ionic surfactant is Polysorbate 80 at a concentration of about 0.02% (w/v).

In certain embodiments of this first aspect, the concentration of the citrate buffer in the liquid pharmaceutical formulation is sufficient to maintain a pH between 5.0 and 5.5. In certain embodiments, the concentration of the citrate buffer in the liquid pharmaceutical formulation is between about 10 mM and 100 mM; or between about 25 mM and 75 mM. In certain embodiments the concentration of the citrate buffer in the liquid pharmaceutical formulation is about 50 mM.

In certain embodiments of this first aspect, the liquid pharmaceutical formulation comprises a tonicity agent. In certain embodiments, the tonicity agent contributes to maintaining the osmolality of the formulation between about 340 mOsm/kg and about 575 mOsm/kg. In certain embodiments of this aspect, the osmolality of the formulation is between about 350 to about 525 mOsm/kg. In some embodiments, the tonicity agent is NaCl. In certain embodiments, the concentration of the NaCl in the liquid pharmaceutical formulation is between about 25 mM and about 200 mM; or between about 75 mM and about 150 mM.

In certain embodiments of this aspect, the liquid formulation exhibits low to undetectable levels of antibody precipitation, aggregation and/or degradation, with little to no loss of biological activity during manufacture, transportation and storage at 2-8° C. for extended periods of at least 12 months, at least 18 months, and/or at least 24 months. In certain embodiments, at least 95%, at least 97%, or at least 98% o of the anti-CD200 antibody molecules or antigen-binding fragments in the liquid pharmaceutical formulation are monomers after storage at 2-8° C. for 24 months.

In a second aspect, provided herein is a liquid formulation comprising (a) at least one anti-CD200 antibody, or antigen binding fragment thereof; (b) a least one neutral amino acid with a non-charged side chain; (c) a non-ionic surfactant; and (d) an acetate buffer at a pH of about 5.0 to about 6.0, wherein the formulation is stable at 2-8° C. for at least about 9 months.

In certain embodiments of the second aspect of the invention, the concentration of the anti-CD200 antibody or antigen binding fragment thereof in the formulation is between about 20 mg/mL and about 100 mg/mL; or is between 20 mg/mL and 50 mg/mL. In certain embodiments, the concentration of anti-CD200 antibody or antigen binding fragment thereof in the formulation is 50 mg/mL.

In certain embodiments of this second aspect, the liquid formulation comprises at least one neutral amino acid selected from the group consisting of alanine, glycine, proline, lysine, leucine or a combination thereof. In certain embodiments, the liquid formulation comprises glycine. In certain embodiments, the concentration of the neutral amino acid of combination thereof is between about 250 mM and about 350 mM. In certain embodiments, the concentration of the neutral amino acid is about 290 mM.

In certain embodiments of this second aspect, the liquid formulation the non-ionic surfactant in the liquid pharmaceutical formulation is a polysorbate (e.g., Polysorbate 20, Polysorbate 40, Polysorbate 60, Polysorbate 80 or a combination of one or more thereof), and is present at a concentration between about 0.001% and 1.0% (w/v). In certain embodiments, the polysorbate is present at a concentration between about 0.01% and 0.1% (w/v). In certain embodiments, the non-ionic surfactant is Polysorbate 80 at a concentration between about 0.01% and 0.1% (w/v). In certain embodiments, the non-ionic surfactant is Polysorbate 80 at a concentration between about 0.025% and 0.1%, particularly 0.05% (w/v).

In certain embodiments of this second aspect, the concentration of the acetate buffer in the liquid pharmaceutical formulation is sufficient to maintain a pH between 5.0 and 6.0. In certain embodiments, the concentration of the acetate buffer in the liquid pharmaceutical formulation is between about 5 mM and 50 mM; or between about 5 mM and 10 mM. In certain embodiments the concentration of the acetate buffer in the liquid pharmaceutical formulation is about 10 mM.

In certain embodiments of this aspect, the liquid formulation exhibits low to undetectable levels of antibody precipitation, aggregation and/or degradation, with little to no loss of biological activity during manufacture, transportation and storage at 2-8° C. for extended periods of at least 9 months, at least 12 months, at least 18 months, and/or at least 24 months.

Also provided are articles of manufacture and kits containing the liquid pharmaceutical formulations disclosed herein, as well as methods for using the liquid pharmaceutical formulations in cancer and autoimmune therapies, and for preventing, delaying or treating cell, tissue, or organ transplant rejection.

Other features and advantages of the liquid antibody formulations will be apparent from the following description, the examples, and from the claims. All publications, patent applications, patents, and other references mentioned herein are incorporated by reference in their entirety.

BRIEF DESCRIPTION OF THE DRAWINGS

FIG. 2 depicts the fractorial analysis of 11M appearance data of the citrate buffered formulations using JMP statistical software. Formulations where precipitation was observed were assigned data values of 0 (zero) while clear and colorless formulations (no precipitation observed) were assigned data values of 1 (one).

FIG. 3 is a table depicting the purity of the 48 citrate buffered test formulations over the 24-month stability study as measured by gel permeation high-performance liquid chromatography (GP-HPLC).

DETAILED DESCRIPTION

Figure 1:
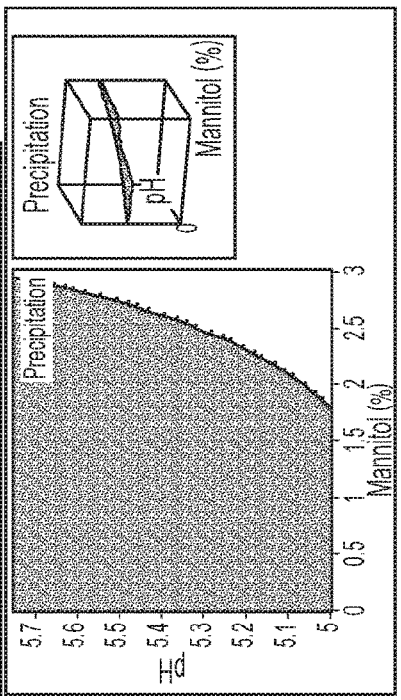
FIG. 1 depicts the stability data for 48 citrate buffered formulations of one anti-CD200 antibody, samalizumab, based on visual appearance of precipitate over 24 months. CC=clear and colorless.

Provided herein are liquid formulations comprising an anti-CD200 antibody that are stable under standard storage and shipping conditions (i.e., 2-8° C.), kits and articles of manufacture containing the liquid formulations, as well as methods for the preparation thereof. Particularly, these liquid formulations are suitable for intravenous and subcutaneous administration. These antibody formulations (or kits or articles of manufacture) can be used alone, or in combination with one or more additional therapeutic agents, in methods for treating cancers or autoimmune diseases, and for prolonging the survival of allografts. While in no way intended to be limiting, suitable applications in which the antibody formulations, kits and articles of manufacture can be used are set forth in this section and exemplified in the working Examples.

I. DEFINITIONS

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of immunology, protein chemistry, biochemistry, recombinant DNA techniques and pharmacology are employed.

As used herein, the singular forms "a", "an" and "the" include plural referents unless the context clearly dictates otherwise. The use of "or" or "and" means "and/or" unless stated otherwise. Furthermore, use of the term "including" as well as other forms, such as "include", "includes", and "included", is not limiting.

The term "about" as used herein when referring to a measurable value such as an amount, a temporal duration and the like, is encompasses variations of up to ±10% from the specified value. Unless otherwise indicated, all numbers expressing quantities of ingredients, properties such as molecular weight, reaction conditions, etc., used herein are to be understood as being modified by the term "about".

The terms "CD200", "OX-2" and "OX-2/CD200" are used interchangeably herein and refers to the highly conserved type I transmembrane glycoprotein having an amino acid sequence of the full-length precursor human CD200 isoform A (SEQ ID NO:1; Genbank Accession No. NP005935.2), the full-length human CD200 isoform B (SEQ ID NO: 2; Genbank Accession No. NP001004196.2), or the full-length human CD200 of SEQ ID NO: 3 (Genbank Accession No. CAA28943.1; FIG. 3 of McCaughan et al. (1987) Immunogenetics 25:329-335).

The term "CD200 antagonist" as used herein includes any agent that is capable of inhibiting the activity, function and/or the expression of CD200 or its receptor. In certain embodiments, the antagonist disrupts the interaction of CD200 and CD200R. In other embodiments, the CD200 antagonist is capable of decreasing the immunosuppressive effects of CD200 or are capable of targeting CD200-expressing cells for depletion or elimination.

The term "antibody" as used herein refers to polypeptides comprising at least one antibody derived antigen binding site (e.g., VH/VL region or Fv, or CDR), and includes whole antibodies and any antigen binding fragments (i.e., "antigen-binding portions") or single chains thereof. Antibodies include known forms of antibodies. For example, the antibody can be a human antibody, a humanized antibody, a bispecific antibody, or a chimeric antibody. A whole "antibody" refers to a glycoprotein comprising at least two heavy (H) chains and two light (L) chains inter-connected by disulfide bonds, in which each heavy chain is comprised of a heavy chain variable region (abbreviated herein as $V_H$) and a heavy chain constant region; and each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered by a protein engineering technique (e.g., by mutation, deletion, substitution, conjugation to a non-antibody moiety). For example, an antibody may include one or more variant amino acids (compared to a naturally occurring antibody) which change a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

The term "antigen-binding portion" of an antibody (or simply "antibody portion"), as used herein, refers to one or more fragments of an antibody that retain the ability to specifically bind to an antigen (e.g., CD200), e.g., a Fab, Fab'2, ScFv, SMIP, Affibody®, nanobody, or a domain antibody. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., Science 242:423-426 (1988); and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. Proc. Natl. Acad. Sci. USA 90:6444-6448 (1993); Poljak, R. J., et al. Structure 2:1121-1123 (1994)). In one embodiment of the invention, the formulation contains an antigen-binding portions described in U.S. Pat. Nos. 6,090,382 and 6,258,562, each incorporated by reference herein.

The term "monoclonal antibody," as used herein, includes an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. The monoclonal antibodies to be used in accordance with the formulations disclosed herein may be made by the hybridoma method first described by Kohler, et a/., (1975) Nature 256: 495 or other methods known in the art. A "polyclonal antibody" is an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

A "humanized" antibody refers to an antibody in which some, most or all of the amino acids outside the CDR domains of a non-human antibody are replaced with corresponding amino acids derived from human immunoglobulins.

A "chimeric antibody" refers to an antibody in which the variable regions are derived from one species and the constant regions are derived from another species, such as an antibody in which the variable regions are derived from a mouse antibody and the constant regions are derived from a human antibody.

An "Fc region," "Fc domain," or "Fc" refers to the C-terminal region of the heavy chain of an antibody. Thus, an Fc region comprises the constant region of an antibody excluding the first constant region immunoglobulin domain (e.g., CH1 or CL). A "native sequence Fc region" or "native sequence Fc" comprises an amino acid sequence that is identical to the amino acid sequence of an Fc region found in nature.

An "antigen" is an entity (e.g., a proteinaceous entity or peptide) to which an antibody binds.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

As used herein, "isotype" refers to the antibody class (e.g., IgG1, IgG2, IgG3, IgG4, IgM, IgA1, IgA2, IgD, and IgE antibody) that is encoded by the heavy chain constant region genes.

Also provided are "conservative sequence modifications" of the sequences set forth herein, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below. The percent identity between two nucleotide or amino acid sequences can also be determined using the algorithm of E. Meyers and W. Miller (*CABIOS,* 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

An "isolated" antibody or antigen binding fragment is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified to greater than 95% by weight of antibody, and in some embodiments, to greater than 99% by weight.

The term "pharmaceutical formulation" refers to preparations which are in such form as to permit the biological activity of the active ingredients to be unequivocally effective, and which contain no additional components which are significantly toxic to the subjects to which the formulation would be administered.

As used herein, an "aqueous" pharmaceutical composition is a composition suitable for pharmaceutical use, wherein the aqueous carrier is water. A composition suitable for pharmaceutical use may be sterile, homogeneous and/or isotonic. Aqueous pharmaceutical compositions may be prepared directly in an aqueous form and/or may be reconstituted from a lyophilisate.

An "isotonic" formulation is one which has essentially the same osmotic pressure as human blood. Isotonic formulations will generally have an osmotic pressure from about 275 to 350 mOsm/kg. The term "hypotonic" describes a formulation with an osmotic pressure below that of human blood. Correspondingly, the term "hypertonic" is used to describe a formulation with an osmotic pressure above that of human blood. Isotonicity can be measured, for example, using a vapor pressure or ice-freezing type osmometer. A "tonicity agent" is a compound which renders the formulation isotonic.

As used herein, the "osmolality" of a solution is the number of osmoles of solute per kilogram of solvent. Osmolality is a measure of the number of particles present in solution and is independent of the size or weight of the particles. It can be measured only by use of a property of the solution that is dependent only on the particle concentration. These properties are vapour pressure depression, freezing point depression, boiling point elevation, and osmotic pressure, and are collectively referred to as colligative properties.

A "sterile" formulation is aseptic or free or essentially free from all living microorganisms and their spores.

A "stable" formulation, as used herein, is one in which the antibody therein essentially retains its physical stability and/or chemical stability and/or biological activity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993).

An antibody "retains its physical stability" in a pharmaceutical formulation if it shows substantially no signs of aggregation, precipitation and/or denaturation upon visual examination of color and/or clarity, or as measured by UV light scattering or by size exclusion chromatography.

The term "aggregation" refers to the assembly of native, folded proteins to from aggregates containing non-native structures. Aggregation can occur even under physiological, non-denaturing conditions, and is often irreversible, resulting in non-native aggregates that are inactive, and sometimes immunogenic and toxic.

The phrase "low to undetectable levels of aggregation" as used herein refers to samples containing no more than about 5%, no more than about 4%, no more than about 3%, no more than about 2%, no more than about 1% and no more than about 0.5% aggregation by weight of protein as measured by gel permeation high-performance liquid chromatography (GP-HPLC), size exclusion chromatography high pressure liquid chromatography (SEC-HPLC), or static light scattering (SLS) techniques.

An antibody "retains its chemical stability" in a pharmaceutical formulation, if the chemical stability at a given time is such that the antibody is considered to still retain its biological activity as defined below. Chemical stability can be assessed by detecting and quantifying chemically altered forms of the antibody. Chemical alteration may involve size modification (e.g., clipping), deamidation, racemization, hydrolysis, oxidation, beta elimination and disulfide exchange which can be evaluated using known techniques, for example, size exclusion chromatography, SDS-PAGE, matrix-assisted laser desorption ionization/time-of-flight mass spectrometry (MALDI/TOF MS), and/or ion-exchange chromatography.

An antibody "retains its biological activity" in a pharmaceutical formulation, if the antibody in a pharmaceutical formulation is biologically active for its intended purpose. For example, biological activity is retained if the biological activity of the antibody in the pharmaceutical formulation is within about 30%, about 20%, or about 10% (within the errors of the assay) of the biological activity exhibited at the time the pharmaceutical formulation was prepared (e.g., as determined in an antigen binding assay).

Herein, "biological activity" of a monoclonal antibody refers to the ability of the antibody to bind to antigen. It can further include antibody binding to antigen and resulting in a measurable biological response which can be measured in vitro or in vivo.

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 surface plasmon resonance instrument using the predetermined antigen, e.g., recombinant human CD200, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, unless otherwise indicated, an antibody that "specifically binds to human CD200" refers to an antibody that binds to soluble or cell bound human CD200 with a $K_D$ of $10^{-7}$ M or less, such as approximately less than $10^{-8}$ M, $10^{-9}$ M or $10^{-10}$ M or even lower.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. *Ann. Biol. Clin.* 51:19-26 (1993); Jonsson, U., et al. (1991) *Biotechniques* 11:620-627; Johnsson, B., et al. (1995) *J. Mol. Recognit.* 8:125-131; and Johnnson, B., et al. *Anal. Biochem.* 198:268-277 (1991).

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore system or flow cytometry and Scatchard analysis.

The term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

A "polyol" is a substance with multiple hydroxyl groups, and includes sugars (reducing and nonreducing sugars), sugar alcohols and sugar acids. A "reducing sugar" is one which contains a hemiacetal group that can reduce metal ions or react covalently with lysine and other amino groups in proteins, and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. Examples of sugar acids, include L-gluconate and metallic salts thereof. A polyl may also act as a tonicity agent.

The term "surfactant" refers to organic substances having amphipathic structures (i.e., composed of groups of opposing solubility tendencies, typically an oil-soluble hydrocarbon chain and a water-soluble ionic group), which can lower the surface tension (or interfacial tension) between two liquids or between a liquid and a solid. Surfactants may act as detergents, wetting agents, emulsifiers, foaming agents, and dispersants. Surfactants can be classified, depending on the charge of the surface-active moiety, into anionic, cationic and non-ionic agents for various pharmaceutical compositions and preparations of biological materials.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

The terms "treat," "treating," and "treatment," as used herein, refer to therapeutic measures described herein. The methods of "treatment" employ administration to a subject the combination disclosed herein in order to cure, delay, reduce the severity of, or ameliorate one or more symptoms of the disease or disorder or recurring disease or disorder, or in order to prolong the survival of a subject beyond that expected in the absence of such treatment.

As used herein, "administering" refers to the physical introduction of a composition comprising a therapeutic agent to a subject, using any of the various methods and delivery systems known to those skilled in the art. Preferred routes of administration for formulations described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intra-arterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually, or topically. Administering can also be performed, for example, once, a plurality of times, and/or over one or more extended periods.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc The terms "effective amount" or "therapeutically effective amount" are used interchangeably and refers to an amount of formulation or antibody effective to alleviate or ameliorate symptoms of disease or to prolong the survival of the subject being treated. Determination of a therapeutically effective amount is within the capability of those skilled in the art, especially in light of the detailed disclosure provided herein. Therapeutically effective dosages may be determined by using in vitro and in vivo methods.

The term "prophylaxis" refers to decreasing the likelihood of, or prevention of, a disease or condition (e.g., cancer, autoimmune disease, allograft rejection).

As used herein, the term "chronically" (e.g., to chronically administer a compound), or similar terms, refers to a method of administration in which an agent (e.g., an anti-CD200 antibody) is administered to a subject in an amount and with a frequency sufficient to maintain an effective amount of the agent in the subject for at least seven (e.g., at least eight, nine, 10, 11, 12, 13, 14, 15, 16, 17, 18, 19, 20, 21, 22, 23, 24). In some embodiments, an agent can be chronically administered to a subject for at least one (e.g., at least two, three, four, five, or six) month(s). In some embodiments, an agent can be chronically administered to a subject for a year or more.

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune response or reaction includes, e.g., activation or inhibition of a T cell, e.g., an effector T cell or a Th cell, such as a CD4+ or CD8+ T cell, or the inhibition of a Treg cell "Immunotherapy" refers to the treatment of a subject afflicted with, or at risk of contracting or suffering a recurrence of, a disease by a method comprising inducing, enhancing, suppressing or otherwise modifying an immune response. "Immunostimulating therapy" or "immunostimulatory therapy" refers to a therapy that results in increasing (inducing or enhancing) an immune response in a subject for, e.g., treating cancer. "Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, the term "T cell-mediated response" refers to a response mediated by T cells, including effector T cells (e.g., CD8$^+$ cells) and helper T cells (e.g., CD4$^+$ cells). T cell mediated responses include, for example, T cell cytotoxicity and proliferation. As used herein, the term "cytotoxic T lymphocyte (CTL) response" refers to an immune response induced by cytotoxic T cells. CTL responses are mediated primarily by CD8$^+$ T cells.

As used herein, the terms "inhibits" or "blocks" (e.g., referring to inhibition/blocking of CD200 binding or activity) are used interchangeably and encompass both partial and complete inhibition/blocking. The term "inhibition" as used herein, refers to any statistically significant decrease in biological activity, including partial and full blocking of the activity. For example, "inhibition" can refer to a statistically significant decrease of about 10%, 20%, 30%, 40%, 50%, 60%, 70%, 80%, 90%, 95%, 96%, 97%, 98%, 99%, or 100% in biological activity.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream. As used herein, the term includes pre-malignant as well as malignant cancers.

As used herein, the term "hematological malignancy" includes a lymphoma, leukemia, myeloma or a lymphoid malignancy, as well as a cancer of the spleen and the lymph nodes. Exemplary lymphomas include both B cell lymphomas and T cell lymphomas.

An "autoimmune disorder," as used herein, refers to a disease state in which, via the action of white blood cells (e.g., B cells, T cells, macrophages, monocytes, or dendritic cells), a pathological immune response (e.g., pathological in duration and/or magnitude) has been generated in a host organism against a substance or a tissue that is normally present within the host organism. Autoimmune diseases are characterized by increased inflammation due to immune system activation against self-antigens.

The terms "allograft," "homograft," and "allogeneic graft" refer to the transplant of an organ or tissue from one individual to another of the same species with a different genotype, including transplants from cadaveric, living related, and living unrelated donors. A graft transplanted from one individual to the same individual is referred to as an "autologous graft" or "autographt". A graft transplanted between two genetically identical or syngeneic individuals is referred to as a "syngeneic graft." A graft transplanted between individuals of different species is referred to as a "xenogeneic graft" or "xenograft.".

Various aspects described herein are described in further detail in the following subsections.

II. ANTI-CD200 ANTIBODIES

Anti-CD200 antibodies for use in the liquid formulations provided herein are CD200 antagonists and include whole antibodies, or antibody fragments capable of binding to CD200 or CD200R, and specifically including anti-CD200 antibodies which block the binding between CD200 and CD200R. Exemplary anti-CD200 antibodies, or antigen binding fragments thereof, which can be used in the formulations described herein include, but are not limited to, those disclosed in U.S. Pat. Nos. 7,408,041; 8,075,884; International Pub. No. WO 2012/106634; and U.S. Provisional Application No. 62/608,300, entitled "Humanized Anti-CD200 Antibodies and Uses Thereof," filed on Dec. 20, 2017 (the contents of each of which are herein incorporated by reference in their entirety).

In certain embodiments, the anti-CD200 antibody, or antigen binding fragment thereof, comprises: (a) a light chain variable domain that comprises (i) a light chain CDR1 comprising the sequence set forth in SEQ ID NO: 4, (ii) a light chain CDR2 comprising the sequence set forth in SEQ ID NO: 5, and (iii) a light chain CDR3 comprising the sequence set forth in SEQ ID NO: 6; and (b) a heavy chain variable domain comprising (i) a heavy chain CDR1 comprising the sequence set forth in SEQ ID NO: 7, (ii) a heavy chain CDR2 comprising the sequence set forth in SEQ ID NO: 8 and (iii) a heavy chain CDR3 comprising the sequence set forth in SEQ ID NO: 9.

In certain embodiments, the amino acid sequences of framework regions of the variable heavy chain domain and a variable light chain domain of the anti-CD200 antibody, or antigen binding fragment thereof are at least 90%, 91%, 92%, 93%, 94%, 95%, 96%, 97%, 98% or 99% identical to the amino acid sequences of the variable heavy chain and variable light chain regions selected from the group consisting of:
 (a) SEQ ID NOs: 10 and 11;
 (b) SEQ ID NOs: 12 and 13;
 (c) SEQ ID NOs: 14 and 15; (d) SEQ ID NOs: 16 and 17; and
 (e) SEQ ID NOs: 18 and 19.

In certain embodiments, the antibody or antigen binding fragment comprises a variable heavy chain sequence and a variable light chain sequence selected from the group consisting of:
 (a) SEQ ID NOs: 10 and 11;
 SEQ ID NOs: 12 and 13;
 (c) SEQ ID NOs: 14 and 15;
 (d) SEQ ID NOs: 16 and 17; and
 (e) SEQ ID NOs: 18 and 19.

In certain embodiments, the antibody or fragment thereof comprises a variable heavy chain sequence as set forth in SEQ ID NO: 10, and a variable light chain sequence as set forth in SEQ ID NO: 11.

In certain embodiments, the antibody comprises a heavy chain sequence and a light chain sequence selected from the group consisting of:
 (a) SEQ ID NOs: 20 and 21;
 (c) SEQ ID NOs: 22 and 23;
 (d) SEQ ID NOs: 24 and 25; and
 (e) SEQ ID NOs: 26 and 27.

In certain embodiments, the antibody comprises a heavy chain sequence as set forth in SEQ ID NO: 20, and a light chain sequence as set forth in SEQ ID NO: 21. In certain embodiments, the anti-CD200 antibody is samalizumab (ALXN6000; Alexion Pharmaceuticals, Inc., New Haven, CT).

The anti-CD200 antibodies in the formulations provided herein include all known forms of antibodies and other protein scaffolds with antibody-like properties. For example, the antibody can be a humanized antibody, bispecific antibody, an immunoconjugate, a chimeric antibody, or a protein scaffold with antibody-like properties, such as fibronectin or ankyrin repeats. The antibody also can be a Fab, Fab'2, scFv, affibody, avimer, nanobody, or a domain antibody. Full-length antibodies can be prepared from $V_H$ and $V_L$ sequences using standard recombinant DNA techniques and nucleic acids encoding the desired constant region sequences can be operatively linked to the variable region sequences In some embodiments, the anti-CD200 antibodies in the formulations provided herein bind to human CD200 with a $K_D$ of about $10^{-7}$ M or less, about $10^{-8}$ M or less, about $10^{-9}$ M or less, about $10^{-10}$ M or less, about $10^{-11}$ M or less, about $10^{-12}$ M or less, about $10^{-7}$ M to about $10^{-12}$ M, about $10^{-7}$ M to about $10^{-11}$ M, about $10^{-7}$ M to about $10^{-10}$ M, about $10^{-8}$ M to about $10^{-12}$ M, about $10^{-9}$ M to about $10^{-12}$ M, about $10^{-10}$ M to about $10^{-12}$ M, about $10^{-10}$ M to about $10^{-11}$ M, about $10^{-9}$ M to about $10^{-11}$ M, or about $10^{-10}$ M to about $10^{-11}$ M.

Standard assays to evaluate the binding ability of the antibodies toward human CD200 are known in the art, including for example, ELISAs, Western blots, and RIAs. Suitable assays are also described in detail in the Examples. The binding kinetics (e.g., binding affinity) of the antibodies also can be assessed by standard assays known in the art, such as by surface plasmon resonance (Biacore analysis) and the Octet assay.

In some embodiments, the anti-CD200 antibodies in the formulations provided herein comprise a modified Fc constant region which has reduced effector function (e.g., antibody-dependent cell-mediated cytotoxicity (ADCC), complement dependent cytotoxicity (CDC), and/or binding to one or more Fc receptors relative to the effector function of the corresponding unmodified Fc constant region. In some embodiments, the anti-CD200 antibodies described herein have no effector function. Modulation refers to an increase, decrease, or elimination of an activity compared to the activity of a second antibody. In certain embodiments, the second antibody is an antibody with effector function, e.g., an antibody having a native sequence Fc or constant region.

In some embodiments, the modified Fc constant region is a G2/G4 constant region (see e.g., Burton et al. (1992) *Adv Immun* 51:1-18; Canfield et al. (1991) *J Exp Med* 173:1483-1491; and Mueller et al. (1997) *Mol Immunol* 34(6):44'-452). For example (and in accordance with Kabat numbering). For example (and in accordance with Kabat numbering), the IgG1 and IgG4 constant regions contain $G_{249}G_{250}$ residues whereas the IgG2 constant region does not contain residue 249, but does contain $G_{250}$. In a G2/G4 hybrid constant region, where the 249-250 region comes from the G2 sequence, the constant region can be further modified to introduce a glycine residue at position 249 to produce a G2/G4 fusion having $G_{249}/G_{250}$. Accordingly, in certain embodiments, the modified Fc constant region of the anti-CD200 antibody in the formulation comprises (i) the CH1 and hinge regions of an IgG2 antibody; (ii) the CH2 and CH3 regions of an IgG4 antibody; or (iii) the CH1 and hinge regions of an IgG2 antibody and the CH2 and CH3 regions of an IgG4 antibody. In another embodiment, the modified Fc constant region lacks a hinge region. In some embodiments, the modified Fc constant region is a G2/G4 constant region comprising the amino acid sequence set forth in SEQ ID NO: 28.

In addition to using a G2/G4 construct as described above, anti-CD200 antibodies with reduced effector function may be produced by introducing other types of changes in the amino acid sequence of certain regions of the antibody. Such amino acid sequence changes include but are not limited to the Ala-Ala mutation described in, e.g., International Publication Nos. WO 94/28027 and WO 98/47531; and Xu et al. (2000) *Cell Immunol* 200:16-26. Thus, in some embodiments, anti-CD200 antibodies with mutations within the constant region including the Ala-Ala mutation may be used to reduce or abolish effector function. According to these embodiments, the constant region of an anti-CD200 antibody comprises a mutation to an alanine at position 234 or a mutation to an alanine at position 235. Additionally, the constant region may contain a double mutation: a mutation to an alanine at position 234 and a second mutation to an alanine at position 235. In one embodiment, the anti-CD200 antibody comprises an IgG4 framework, wherein the Ala-Ala mutation would describe a mutation(s) from phenylalanine to alanine at position 234 and/or a mutation from leucine to alanine at position 235. In another embodiment, the anti-CD200 antibody comprises an IgG 1 framework, wherein the Ala-Ala mutation would describe a mutation(s) from leucine to alanine at position 234 and/or a mutation from leucine to alanine at position 235. An anti-CD200 antibody may alternatively or additionally carry other mutations, including the point mutation K322A in the CH2 domain (Hezareh et al. (2001) *J Virol* 75:12161-8).

Additional substitutions that, when introduced into a heavy chain constant region, result in decreased effector function are set forth in, e.g., Shields et al. (2001) *J Biol Chem* 276(9):6591-6604. See particularly Table 1 ("Binding of human IgG1 variants to human FcRn and FcγR) of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al.) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669.

In some embodiments, anti-CD200 antibodies in the formulations provided herein may be modified to either enhance or inhibit complement dependent cytotoxicity (CDC). Modulated CDC activity may be achieved by introducing one or more amino acid substitutions, insertions, or deletions in an Fc region of the antibody (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., *J. Exp Med.* 176:1191-1195 (1992) and Shopes, B. *J. Immunol.* 148:2918-2922 (1992), WO 99/51642, Duncan & Winter, *Nature* 322: 738-40 (1988); U.S. Pat. Nos. 5,648, 260; 5,624,821; and WO 94/29351. Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317, 091; 8,101,720; International Publication Nos. WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

Anti-CD200 antibodies comprising Fc variants that enhance affinity for an inhibitory receptor FcγRIIb may also be used. Such variants may provide an Fc fusion protein with immunomodulatory activities related to FcγRIIb cells, including for example B cells and monocytes. In one embodiment, the Fc variants provide selectively enhanced affinity to FcγRIIb relative to one or more activating receptors. In certain embodiments, the antibody is modified to increase its biological half-life. For example, this may be done by increasing the binding affinity of the Fc region for FcRn. The binding sites of human IgG1 for FcγR1, FcγRII, FcγRIII and FcRn have been mapped and variants with improved binding have been described (see Shields, R. L. et al. (2001) *J. Biol. Chem.* 276:6591-6604).

III. METHODS OF ANTIBODY PRODUCTION

Antibodies and antigen binding fragments thereof may be obtained according to established hybridoma and recombinant procedures. Suitable methods for producing an antibody (e.g., an anti-CD200 antibody) or antigen-binding fragments thereof may be obtained according to established hybridoma and recombinant procedures as previously disclosed (see, e.g., U.S. Pat. Nos. 7,427,665; 7,435,412; and 7,408,041, the disclosures of each of which are incorporated herein by reference in their entirety).

For example, a process for the production of an antibody disclosed herein includes culturing a host (e.g., *E. coli* or a mammalian cell), which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic, for example bicistronic, DNA sequences encoding antibody proteins each individually operably linked to a signal peptide in the proper reading frame.

Multiplication of hybridoma cells or mammalian host cells in vitro (e.g., E. coli or a mammalian cell (e.g., CHO cell) which have been transformed with nucleic acids encoding the anti-CD200 antibody or antibody fragment) is carried out in suitable culture media, which include the customary standard culture media (such as, for example Dulbecco's Modified Eagle Medium (DMEM) or RPMI 1640 medium), optionally replenished by a mammalian serum (e.g., fetal calf serum), or trace elements and growth sustaining supplements (e.g., feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2.times.YT, or M9 Minimal Medium. For yeast, suitable culture media include medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast, plant, or mammalian cell cultivation are known in the art and include homogeneous suspension culture (e.g., in an airlift reactor or in a continuous stirrer reactor), and immobilized or entrapped cell culture (e.g., in hollow fibers, microcapsules, on agarose microbeads or ceramic cartridges).

Large quantities of the desired antibodies can also be obtained by multiplying mammalian cells in vivo. For this purpose, cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristine. After one to two weeks, ascitic fluid is taken from the animals.

The antibody which is formulated is preferably essentially pure and desirably essentially homogeneous (e.g., free from contaminating proteins etc). "Essentially pure" antibody means a composition comprising at least about 90% by weight of the antibody, based on total weight of the composition, preferably at least about 95% by weight. "Essentially homogeneous" antibody means a composition comprising at least about 99% by weight of antibody, based on total weight of the composition.

Techniques for purification of therapeutic antibodies to pharmaceutical grade are known in the art. For example, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g., affinity chromatography with a one or more surface polypeptides derived from a CD200-expressing cell line, synthetic CD200 peptide fragments, or with Protein-A or G.

The foregoing, and other, techniques are discussed in, for example, Kohler and Milstein, Nature 256:495-497 (1975); U.S. Pat. No. 4,376,110; Harlow and Lane, Antibodies: a Laboratory Manual (1988) Cold Spring Harbor, the disclosures of which are all incorporated herein by reference. Techniques for the preparation of recombinant antibody molecules is described in the above references and also in, for example, International Pub. No. WO 97/08320; U.S. Pat. Nos. 5,427,908; 5,508,717; Smith, Science, 225:1315-1317 (1985); Parmley and Smith Gene 73:305-318 (1988); De La Cruz et al., J. Biol. Chem., 263:4318-4322 (1988); U.S. Pat. Nos. 5,403,484; 5,223,409; WO88/06630; WO92/15679; U.S. Pat. Nos. 5,780,279; 5,571,698; 6,040,136; Davis et al., Cancer Metastasis Rev., 18(4):421-5 (1999); Taylor, et al., Nucleic Acids Research 20: 6287-6295 (1992); Tomizuka et al., Proc. Nat. Academy of Sciences USA 97(2): 722-727 (2000) (the contents of each are incorporated herein by reference).

IV. ANTI-CD200 ANTIBODY FORMULATIONS

The liquid formulations provided herein comprise a therapeutically effective amount of the anti-CD200 antibody or antigen binding fragment thereof, in a buffered solution having a pH between about 5.0 and 6.0, and an osmolality of less than 600 mOsmo/kg. These formulations exhibit improved stability at low temperatures (e.g., 2-8° C.) for an extended period, and improved physiological properties (e.g., osmolality) compared to previous anti-CD200 antibody formulations.

A. Citrate Buffered Anti-CD200 Formulations

In one aspect, the liquid formulations provided herein comprise a therapeutically effective amount of at least one anti-CD200 antibody, or antigen binding fragment thereof, a polyol, a non-ionic surfactant, and a citrate buffer at a pH of about 5.0 to 5.5.

The concentration of the anti-CD200 antibody, or antigen binding fragment thereof in the citrate buffered liquid formulation described herein is determined, for example, by taking into account the desired dose volumes and mode(s) of administration. In some embodiments, the antibody concentration in the citrate buffered formulation is at least about 5 mg/ml, for example, between about 5 mg/ml to about 25 mg/ml. In some embodiments, the concentration of the antibody in the citrate buffered formulation is between about 5 to about 15 mg/ml. In other embodiments, the concentration of the antibody in the citrate buffered formulation is between about 5-10 mg/ml.

In some embodiments, the concentration of antibody in the citrate-buffered formulation is about 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml or 25 mg/ml. In one embodiment, the antibody concentration in the formulation is about 5 mg/ml.

In another embodiment, the antibody concentration in the formulation is about 10 mg/ml. Ranges intermediate to the above recited concentrations (e.g., about 6-23 mg/ml) can also be used in the liquid formulations. For example, ranges of values using a combination of any of the above recited values as upper and/or lower limits are intended to be included.

The amount of polyol added to the citrate buffered formulation may vary with respect to the desired isotonicity of the formulation, and the molecular weight of the polyol. Polyols which can be used in the formulations include sugars (reducing and nonreducing sugars), sugar alcohols and sugar acids. In certain embodiments, the polyol in the citrate buffered formulation has a molecular weight which is less than about 600 kD (e.g., in the range from about 120 to about 400 kD). In some embodiments, the polyol in the formulation is a sugar alcohol, including but not limited to mannitol, xylitol, erythritol, threitol, sorbitol and glycerol. In certain embodiments, the polyol in the formulation is mannitol.

In some embodiments, the citrate buffered formulation comprises at least 1% mannitol (w/v). In other embodiments, the formulation comprises between about 1% to about 5% mannitol, or between about 1% to about 3% mannitol. In certain embodiments, the formulation comprises about 1.0, 1.1, 1.2, 1.3, 1.4, 1.5, 1.6, 1.6, 1.7, 1.8, 1.9, 2.0, 2.1, 2.2, 2.3, 2.4, 2.5, 2.6, 2.7, 2.8, 2.9, or 3.0% mannitol. In one embodiment, the formulation comprises about 1% mannitol. In another embodiment, the formulation comprises about 2% mannitol. In another embodiment, the formulation comprises about 3% mannitol.

Surfactants for use in the citrate buffered formulation protect the anti-CD200 antibody or fragment thereof from surface (e.g., agitation or shaking) and stress induced aggregation (e.g., freezing, lyophilization, and reconstitutution). Suitable surfactants include, but are not limited to, sorbitan fatty acid esters (e.g., sorbitan monocaprylate, sorbitan monolaurate, sorbitan monopalmitate), sorbitan trioleate, glycerine fatty acid esters (e.g., glycerine monocaprylate, glycerine monomyristate, glycerine monostearate, etc.), polyglycerine fatty acid esters (e.g., decaglyceryl monostearate, decaglyceryl distearate, decaglyceryl monolinoleate), polyoxyethylene sorbitan fatty acid esters (e.g., polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g., polyoxyethylene sorbitol tetrastearate, polyoxyethylene sorbitol tetraoleate), polyoxyethylene glycerine fatty acid esters (e.g., polyoxyethylene glyceryl monostearate), polyethylene glycol fatty acid esters (e.g., polyethylene glycol distearate), polyoxyethylene alkyl ethers (e.g., polyoxyethylene lauryl ether), polyoxyethylene polyoxypropylene alkyl ethers (e.g., polyoxyethylene polyoxypropylene glycol, polyoxyethylene polyoxypropylene propyl ether, polyoxyethylene polyoxypropylene cetyl ether), polyoxyethylene alkylphenyl ethers (e.g., polyoxyethylene nonylphenyl ether), polyoxyethylene hydrogenated castor oils (e.g., polyoxyethylene castor oil, polyoxyethylene hydrogenated castor oil), polyoxyethylene beeswax derivatives (e.g., polyoxyethylene sorbitol beeswax), polyoxyethylene lanolin derivatives (e.g., polyoxyethylene lanolin), and polyoxyethylene fatty acid amides (e.g., polyoxyethylene stearic acid amide); $C_{12}$-$C_{18}$ alkyl sulfates (e.g., sodium cetyl sulfate, sodium lauryl sulfate, sodium oleyl sulfate), polyoxyethylene $C_{10}$-$C_{18}$ alkyl ether sulfate with an average of 2 to 4 moles of ethylene oxide units added (e.g., sodium polyoxyethylene lauryl sulfate), and $C_{10}$-$C_{18}$ alkyl sulfosuccinate ester salts (e.g., sodium lauryl sulfosuccinate ester); and natural surfactants such as lecithin, glycerophospholipid, sphingophospholipids (e.g., sphingomyelin), t-octylphenoxypolyethoxyethanol (Triton-X100), polyethylene glycol oleyl ether (Brij, Aldrich), and sucrose esters of $C_{12}$-$C_{18}$ fatty acids.

In some embodiments, the surfactant in the citrate buffered formulation is a non-ionic surfactant. In certain embodiments, the surfactant in the citrate buffered formulation is a polyoxyethylene sorbitan fatty acid ester, for example, polysorbate 20, 40, 60, 80, or a combination of one or more thereof. In one embodiment, the surfactant in the citrate buffered formulation is polysorbate 80 (Tween 80). In another embodiment, the surfactant in the formulation is polysorbate 60. In another embodiment, the surfactant in the formulation is polysorbate 40. In another embodiment, the surfactant in the formulation is polysorbate 20 (Tween 20).

The amount of non-ionic surfactant added to the citrate buffered formulation is sufficient to reduce aggregation of the formulated antibody and/or minimize the formation of particulates in the formulation. For example, the non-ionic surfactant may be present in the formulation in an amount from about 0.001% to about 1%, or about 0.001% to about 0.5%, or about 0.01% to about 0.2%. In certain embodiments, the citrate buffered formulations comprise a polysorbate at a concentration from about 0.001% to about 0.5%, from about 0.005% to about 0.2%, from about 0.01% to about 0.1%, or from about 0.02% to about 0.06%, or about 0.03% to about 0.05% (w/v). In certain embodiments, the citrate buffered formulation comprises a polysorbate at a concentration of 0.01%, or 0.02%, or 0.03%, or 0.04%, or 0.05%, or 0.06%, or 0.07%, or 0.08%, or 0.09%, or 0.1%, or 0.15%, or 0.2% (w/v). In certain embodiments, the surfactant is present in the citrate buffered formulation in an amount of 0.02% or about 0.04% (w/v). In one embodiment, the polysorbate is present in the citrate buffered formulation in an amount of 0.02% (w/v).

In certain embodiment, the citrate buffered formulation comprises at least about 0.01%, at least about 0.02%, at least about 0.05%, at least about 0.1%, at least about 0.2%, at least about 0.3%, at least about 0.4%, or at least about 0.5% polysorbate 80. In certain embodiment, the citrate buffered formulation comprises between about 0.01% and about 0.5%, between about 0.01% and about 0.3%, between about 0.01% and about 0.2%, between about 0.02% and about 0.5%, between about 0.02% and about 0.3%, between about 0.02% and about 0.2%, between about 0.05% and about 0.5%, between about 0.05% and about 0.3%, between about 0.05% and about 0.2%, between about 0.075% and about 0.5%, between about 0.075% and about 0.3%, or between about 0.075% and about 0.2% Polysorbate 80. In a further embodiment, the formulation comprises about 0.01%, about 0.02%, about 0.03%, about 0.04%, about 0.05%, about 0.1%, about 0.2%, about 0.3%, about 0.4%, or about 0.5% Polysorbate 80. In one embodiment, the formulation comprises about comprises about 0.04% polysorbate 80. In one embodiment, the formulation comprises about 0.03% polysorbate 80. In one embodiment, the formulation comprises about 0.02% polysorbate 80. In one embodiment, the formulation comprises about 0.01% polysorbate 80.

The liquid citrate buffered formulations provided herein are at a pH of between about 5.0 to about 6.0. As used herein, "buffer" refers to a buffered solution that resists changes in pH by the action of its acid-base conjugate components. Suitable citrate buffers contain citric acid (e.g., citric acid monohydrate), sodium citrate, sodium citrate dehydrate, trisodium citrate, dibasic sodium phosphate or sodium phosphate heptahydrate. In certain embodiments, the citrate buffer is a sodium citrate buffer.

In certain embodiments, the liquid citrate buffered formulation is buffered at a pH between about 5.0-5.9, 5.0-5.8, 5.0-5.7, 5.0-5.6, 5.0-5.5, 5.0-5.4, 5.0-5.3, 5.0-5.2. In certain embodiments, the pH of the formulation is about 5.0, 5.1, 5.15, 5.2, 5.25, 5.3, 5.4, 5.45, 5.5, 5.55, 5.6, 5.65, 5.7, 5.75, 5.8, 5.85, 5.9, 5.95 or 6.0. In certain embodiments, the pH of the citrate buffered formulation is about 5.25-5.5. In one embodiment, the pH of the citrate buffered formulation is about 5.2

The concentration of the citrate buffer in the formulation is sufficient to maintain the desired pH and may also be varied, for example, to maintain the isotonicity of the formulation. Typical concentrations of conventional buffering agents employed in parenteral formulations can be found in: *Pharmaceutical Dosage Form: Parenteral Medications*, Volume 1, 2nd Edition, Chapter 5, p. 194, De Luca and Boylan, "Formulation of Small Volume Parenterals", Table 5: Commonly Used Additives in Parenteral Products. In some embodiments, the concentration of the citrate buffer in the formulation is about 10 mM to 100 mM. In some embodiments, the concentration of the citrate buffer in the formulation is about 20 mM to about 80 mM, or about 25 mM to about 75 mM. In some embodiments, the concentration of the citrate buffer in the formulation is at least about 20 mM or at least about 25 mM. In certain embodiments, the concentration of the citrate buffer in the formulation is about 20 mM, 25 mM, 30 mM, 35 mM, 40 mM, 45 mM, 50 mM, 55 mM, 60 mM, 65 mM, 70 mM, 75 mM, 80 mM, 90 mM, 95 mM or about 100 mM. In one, the concentration of the citrate buffer in the formulation is about 25 mM. In another embodiment, the concentration of the citrate buffer in the formulation is about 50 mM. In another embodiment, the concentration of the citrate buffer in the formulation is about 75 mM.

In some embodiments, the liquid citrate buffered formulation contains sodium chloride as a tonicity agent to adjust the osmolality of the formulation (e.g., greater than about 340 mOsm/k and less than about 600 mOsm/k). In certain embodiments, the final concentration of sodium chloride in the formulation is from about 25 mM to about 200 mM, or from about 50 mM to 150 mM. In certain embodiments, the final concentration of sodium chloride in the formulation is about 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, or about 150 mM.

In particular embodiments, the liquid citrate buffered formulation comprises:
a. about 5 mg/ml to about 10 mg/ml the anti-CD200 antibody or antigen binding fragment thereof;
b. about 1% to about 3% mannitol;
c. about 0.01% to about 0.05% polysorbate;
d. about 25 mM to about 75 mM citrate buffer to a pH of 5.0 to 5.5; and
e. about 75 mM to about 150 mM NaCl.

In one embodiment, the anti-CD200 antibody is samalizumab. In another embodiment, the polysorbate is polysorbate 80. In another embodiment, the pH of the formulation is about 5.25. In another embodiment, the osmolality of the formulation is about 350 mOsm/kg to about 525 mOsm/kg.

In other particular embodiments, the liquid formulation consists essentially of:
a. about 5 mg/ml to about 10 mg/ml the anti-CD200 antibody or antigen binding fragment thereof;
b. about 1% to about 3% mannitol;
c. about 0.01% to about 0.05% polysorbate;
d. about 25 mM to about 75 mM citrate buffer to a pH of 5.0 to 5.5; and
e. about 75 mM to about 150 mM NaCl.

In one embodiment, the anti-CD200 antibody is samalizumab. In another embodiment, the polysorbate is polysorbate 80. In another embodiment, the pH of the formulation is about 5.25. In another embodiment, the osmolality of the formulation is about 350 mOsm/kg to about 525 mOsm/kg.

In other particular embodiments, the liquid formulation comprises:
a. about 5 mg/ml to about 10 mg/ml samalizumab;
b. about 1% to about 3% mannitol;
c. about 0.01% to about 0.05% polysorbate;
d. about 50 mM citrate buffer to a pH of 5.0 to 5.5; and
e. about 75 mM to about 150 mM NaCl.

In one embodiment, the polysorbate is polysorbate 80. In one embodiment, the formulation comprises about 0.02% polysorbate 80. In another embodiment, the osmolality of the formulation is about 350 mOsm/kg to about 525 mOsm/kg.

In one particular embodiment, the liquid formulation comprises:
a. about 5 mg/ml samalizumab;
b. about 1% mannitol;
c. about 0.02% polysorbate 80;
d. about 50 mM citrate buffer to a pH of about 5.5; and
e. about 75 mM NaCl.

In one particular embodiment, the liquid formulation comprises:
a. about 5 mg/ml samalizumab;
b. about 3% mannitol;
c. about 0.02% polysorbate 80;
d. about 50 mM citrate buffer to a pH of about 5.5; and
e. about 75 mM NaCl.

In one particular embodiment, the liquid formulation comprises:
a. about 5 mg/ml samalizumab;
b. about 1% mannitol;
c. about 0.02% polysorbate 80;
d. about 50 mM citrate buffer to a pH of about 5.25; and
e. about 75 mM NaCl.

In one particular embodiment, the liquid formulation comprises:
a. about 5 mg/ml samalizumab;
b. about 3% mannitol;
c. about 0.02% polysorbate 80;
d. about 50 mM citrate buffer to a pH of about 5.5; and
e. about 75 mM NaCl.

In one particular embodiment, the liquid formulation comprises:
a. about 5 mg/ml samalizumab;
b. about 1% mannitol;
c. about 0.02% polysorbate 80;
d. about 50 mM citrate buffer to a pH of about 5.0; and
e. about 75 mM NaCl.

In one particular embodiment, the liquid formulation comprises:
a. about 5 mg/ml samalizumab;
b. about 3% mannitol;
c. about 0.02% polysorbate 80;
d. about 50 mM citrate buffer to a pH of about 5.0; and
e. about 75 mM NaCl.

In one particular embodiment, the liquid formulation comprises:
a. about 10 mg/ml samalizumab;
b. about 1% mannitol;
c. about 0.02% polysorbate 80;
d. about 50 mM citrate buffer to a pH of about 5.25; and
e. about 75 mM NaCl.

In one particular embodiment, the liquid formulation comprises:
a. about 10 mg/ml samalizumab;
b. about 3% mannitol;
c. about 0.02% polysorbate 80;
d. about 50 mM citrate buffer to a pH of about 5.25; and
e. about 75 mM NaCl.

In one particular embodiment, the liquid formulation comprises:
a. about 10 mg/ml samalizumab;
b. about 1% mannitol;
c. about 0.02% polysorbate 80;
d. about 50 mM citrate buffer to a pH of about 5.00; and
e. about 75 mM NaCl.

In one particular embodiment, the liquid formulation comprises:
a. about 10 mg/ml samalizumab;
b. about 3% mannitol;
c. about 0.02% polysorbate 80;
d. about 50 mM citrate buffer to a pH of about 5.00; and
e. about 75 mM NaCl.

B. Acetate Buffered Anti-CD200 Formulations

In a second aspect, provided herein are the liquid formulations which comprise a therapeutically effective amount of at least one anti-CD200 antibody, or antigen binding fragment thereof, a neutral amino acid with a non-charged side chain, a non-ionic surfactant, and an acetate buffer at a pH of about 5.0 to 6.0.

In some embodiments, the antibody concentration in the acetate buffered formulation at least about 20 mg/ml, for example, between about 20 mg/ml to about 100 mg/ml. In some embodiments, the concentration of the antibody in the acetate buffered formulation is between about 20 to about 75 mg/ml. In other embodiments, the concentration of the antibody in the acetate buffered formulation is between about 25 to about 50 mg/ml. In some embodiments, the concentration of the antibody in the acetate buffered formulation is suitable for subcutaneous (SC) delivery.

In some embodiments, the concentration of antibody in the acetate buffered formulation is about 20 mg/ml, 25 mg/ml, 30 mg/ml, 35 mg/ml, 40 mg/ml, 45 mg/ml, 50 mg/ml, 55 mg/ml, 60 mg/ml, 65 mg/ml, 70 mg/ml, 75 mg/ml, 80 mg/ml, 85 mg/ml, 90 mg/ml, 95 mg/ml, 100 mg/ml or greater than 100 mg/ml, e.g., up to 150 mg/ml. In one embodiment, the antibody concentration in the formulation is about 50 mg/ml. Ranges intermediate to the above recited concentrations can also be used in the liquid formulations. For example, ranges of values using a combination of any of the above recited values as upper and/or lower limits are intended to be included.

In some embodiments, the neutral amino acid in the acetate buffered formulation is alanine, glycine, isoleucine, leucine, methionine, phenylalanine, proline, valine or a combination thereof. In some embodiments, the neutral amino acid in the acetate buffered formulation is glycine, proline, arginine, lysine or leucine. In certain embodiments, the neutral amino acid in the acetate buffered formulation is glycine.

The concentration of the neutral amino acid in the acetate buffered formulation is sufficient to act as a stabilizer/tonicifier. In some embodiments, the concentration of the neutral amino acid in the acetate buffered formulation is at least 200 mM, for example, between about 200 mM and 500 mM. In some embodiments, the concentration of the neutral amino acid is between 250 mM and 350 mM. In some embodiments, the concentration of the neutral amino acid is about 220 mM, 230 mM, 240 mM, 250 mM, 260 mM, 270 mM, 280 mM, 290 mM, 300 mM, 310 mM, 320 mM, 330 mM, 340 mM or 350 mM.

In certain embodiments, the concentration of the neutral amino acid in the acetate buffered formulation is glycine at a concentration of between about 250 mM and 350 mM. In some embodiments, the concentration of the glycine in the formulation is about 220 mM, 230 mM, 240 mM, 250 mM, 260 mM, 270 mM, 280 mM, 290 mM, 300 mM, 310 mM, 320 mM, 330 mM, 340 mM or 350 mM. In certain embodiments, the concentration of glycine in the formulation is 290 mM.

Suitable surfactants for use in the acetate buffered formulation include those which protect the anti-CD200 antibody or fragment thereof from surface (e.g., agitation or shaking) and stress induced aggregation (e.g., freezing, lyophilization, and reconsititution. In some embodiments, the surfactant in the acetate buffered formulation is a non-ionic surfactant. In certain embodiments, the surfactant in the acetate buffered formulation is a polyoxyethylene sorbitan fatty acid ester, for example, polysorbate 20, 40, 60, 80, or a combination of one or more thereof. In certain embodiments, the surfactant in the acetate buffered formulation is polysorbate 80 (Tween 80). In other embodiments, the surfactant in the formulation is polysorbate 60. In other embodiments, the surfactant in the formulation is polysorbate 40. In other embodiments, the surfactant in the formulation is polysorbate 20 (Tween 20).

The amount of non-ionic surfactant added to the acetate buffered formulation is sufficient to reduce aggregation of the formulated antibody and/or minimize the formation of particulates in the formulation. For example, the non-ionic surfactant may be present in the formulation in an amount from about 0.001% to about 1%, or about 0.001% to about 0.5%, or about 0.01% to about 0.2%. In certain embodiments, the acetate buffered formulations comprise a polysorbate at a concentration from about 0.001% to about 0.5%, from about 0.005% to about 0.2%, from about 0.01% to about 0.1%, or from about 0.02% to about 0.06%, or about 0.03% to about 0.05% (w/v). In certain embodiments, the acetate buffered formulation comprises a polysorbate at a concentration of 0.01%, or 0.02%, or 0.03%, or 0.04%, or 0.05%, or 0.06%, or 0.07%, or 0.08%, or 0.09%, or 0.1%, or 0.15%, or 0.2% (w/v). In certain embodiments, the surfactant is present in the acetate buffered formulation in an amount of 0.02% or about 0.06% (w/v). In one embodiment, the polysorbate is present in the acetate buffered formulation in an amount of 0.05% (w/v).

In certain embodiments, the acetate buffered formulation comprises at least about 0.01%, at least about 0.02%, at least about 0.05%, at least about 0.1%, at least about 0.2%, at least about 0.3%, at least about 0.4%, or at least about 0.5% polysorbate 80. In certain embodiment, the acetate buffered formulation comprises between about 0.01% and about 0.5%, between about 0.01% and about 0.3%, between about 0.01% and about 0.2%, between about 0.02% and about 0.5%, between about 0.02% and about 0.3%, between about 0.02% and about 0.2%, between about 0.05% and about 0.5%, between about 0.05% and about 0.3%, between about 0.05% and about 0.2%, between about 0.075% and about 0.5%, between about 0.075% and about 0.3%, or between about 0.075% and about 0.2% Polysorbate 80. In a further embodiment, the formulation comprises about 0.01%, about 0.02%, about 0.03%, about 0.04%, about 0.05%, about 0.1%, about 0.2%, about 0.3%, about 0.4%, or about 0.5% Polysorbate 80. In one embodiment, the formulation comprises about comprises about 0.05% polysorbate 80.

The liquid acetate buffered formulations provided herein are at a pH of between about 5.0 to about 6.0. Suitable acetate buffers include sodium acetate, sodium acetate dehydrate, trisodium acetate, dibasic sodium phosphate or sodium phosphate heptahydrate. In certain embodiments, the acetate buffer is a sodium acetate buffer.

In certain embodiments, the liquid acetate buffered formulation is buffered at a pH between about 5.0-5.9, 5.0-5.8, 5.0-5.7, 5.0-5.6, 5.0-5.5, 5.0-5.4, 5.0-5.3, 5.0-5.2. In certain embodiments, the pH of the formulation is about 5.0, 5.1, 5.15, 5.2, 5.25, 5.3, 5.4, 5.45, 5.5, 5.55, 5.6, 5.65, 5.7, 5.75, 5.8, 5.85, 5.9, 5.95 or 6.0. In certain embodiments, the pH of the acetate buffered formulation is about 5.25-5.5. In one embodiment, the pH of the acetate buffered formulation is about 5.5.

The concentration of the acetate buffer in the formulation is sufficient to maintain the desired pH and may also be varied, for example, to maintain the isotonicity of the formulation. Typical concentrations of conventional buffering agents employed in parenteral formulations can be found in: *Pharmaceutical Dosage Form: Parenteral Medications*, Volume 1, 2nd Edition, Chapter 5, p. 194, De Luca and Boylan, "Formulation of Small Volume Parenterals", Table 5: Commonly Used Additives in Parenteral Products. In some embodiments, the concentration of the acetate buffer in the formulation is about 5 mM to 50 mM. In some embodiments, the concentration of the acetate buffer in the formulation is about 5 mM to about 25 mM, or about 5 mM to about 10 mM. In some embodiments, the concentration of the acetate buffer in the formulation is at least about 5 mM or at least about 10 mM. In certain embodiments, the concentration of the acetate buffer in the formulation is about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM or about 20 mM. In one, the concentration of the acetate buffer in the formulation is about 10 mM.

In particular embodiments of this aspect of the invention, the liquid formulation comprises:
  (a) about 20 mg/ml to about 100 mg/ml of at least one anti-CD200 antibody or antigen binding fragment thereof;
  (b) about 200 mM to 500 mM of at least one neutral amino acid with a non-charged side chain;
  (c) about 0.01% to about 0.1% polysorbate; and
  (d) about 5 mM to about 20 mM acetate buffer to a pH of 5.0 to 6.0.

In one embodiment, the anti-CD200 antibody is samalizumab. In another embodiment, the polysorbate is polysorbate 80. In another embodiment, the pH of the formulation is about 5.5.

In other particular embodiments, the acetate buffered formulation consists essentially of:
  (a) about 20 mg/ml to about 100 mg/ml of at least one anti-CD200 antibody or antigen binding fragment thereof;
  (b) about 200 mM to 500 mM of at least one neutral amino acid with a non-charged side chain;
  (c) about 0.01% to about 0.1% polysorbate; and
  (d) about 5 mM to about 20 mM acetate buffer to a pH of 5.0 to 6.0.

In one embodiment, the anti-CD200 antibody is samalizumab. In another embodiment, the polysorbate is polysorbate 80. In another embodiment, the pH of the formulation is about 5.5.

In other particular embodiments, the acetate buffered formulation comprises:
  a) about 50 mg/ml of at least one anti-CD200 antibody or antigen binding fragment thereof;
  (b) about 250 mM to about 350 mM glycine;
  (c) about 0.02% to about 0.0.5% polysorbate; and
  (d) about 10 mM acetate buffer to a pH of 5.0 to 6.0.

In one embodiment, the anti-CD200 antibody is samalizumab. In another embodiment, the polysorbate is polysorbate 80. In another embodiment, the pH of the formulation is about 5.5. In one particular embodiment, the acetate buffered formulation comprises:
  a) about 50 mg/ml of samalizumab;
  (b) about 290 mM glycine;
  (c) about 0.0.5% polysorbate 80; and
  (d) about 10 mM acetate buffer to a pH of 5.5.

C. Additional Embodiments

In additional embodiments, both the citrate buffered and acetate buffered formulations provided herein containing an anti-CD200 antibody or antigen binding fragment thereof, are not hypertonic (i.e., are isotonic) with respect to blood (e.g., plasma), or are not so hypertonic (i.e., slightly hypertonic) as to cause significant thrombosis, phlebitis and/or vessel irritation. The osmolality of any pharmaceutical preparation can be calculated by using the following formula: Osmolality=(weight of substance (g) divided by the molecular weight of the substance (g/L)) multiplied by the number of species multiplied by 1000 for milliosmolarity. The term "species" refers to the number of ions or chemical species formed when dissolution occurs.

The reference range of osmolality in human plasma is about 275-295 mOsm/kg. The osmolality of the liquid formulation can be adjusted by varying the amounts of tonicity agents in the formulation (e.g., mannitol or neutral amino acid), or by including additional tonicity agents. Additional tonicity agents which may be used in the liquid formulation include, for example, dextrose, glycerin, potassium chloride and sodium chloride.

Accordingly, the osmolality of the citrate buffered and acetate buffered formulations provided herein is less than about 600 mOsmo/kg. In some embodiments, the formulation is slightly hypertonic and has an osmolality that is greater than about 340 mOsm/kg and less than about 600 mOsm/kg. In some embodiments, the liquid formulation has an osmolality that is greater than about 340 and less than about 375, 400, 425, 450, 475, 500, or about 575 mOsm/kg. In certain embodiments, the formulations described herein demonstrate an osmolality from about 350 mOsmo/kg to about 525 mOsmo/kg, about 350-500 mOsmo/kg, about 350-475 mOsmo/kg, about 350-450 mOsmo/kg, 350-425 mOsmo/kg, 350-400 mOsmo/kg, or 350-375 mOsmo/kg.

In some embodiments, the both the citrate buffered and acetate buffered formulations provided herein are essentially free of one or more preservatives, such as benzyl alcohol, phenol, m-cresol, chlorobutanol and benzethonium Cl. In other embodiments, a preservative may be included in the formulation, particularly where the formulation is a multi-dose formulation.

In some embodiment the both the citrate buffered and acetate buffered formulations provided herein are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, *Pharmacopeial Forum* 26 (1):223 (2000)). When therapeutic proteins are administered in amounts of several hundred or thousand milligrams per kilogram body weight, as can be the case with antibodies, even trace amounts of harmful and dangerous endotoxin must be removed. In certain specific embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

One or more other pharmaceutically acceptable carriers, excipients or stabilizers such as those described in *Remington's Pharmaceutical Sciences* 16th edition, Osol, A. Ed. (1980) also may be included in the both the citrate buffered and acetate buffered formulations provided that they do not significantly adversely affect the desired characteristics of the formulation. Acceptable carriers, excipients or stabilizers are nontoxic to recipients at the dosages and concentrations employed and include; additional buffering agents; co-solvents; antioxidants; chelating agents such as EDTA; and/or biodegradable polymers such as polyesters.

The liquid formulations anti-CD200 antibody formulations provided herein are stable at under standard shipping and storage conditions. The stability of the formulations is determined, for example, as described in the Examples. In some embodiments, the formulation is considered stable if the anti-CD200 antibody or antigen binding fragment remains soluble (i.e., shows no visible precipitation upon visual inspection) at 2-8° C. for at least 9 months, at least 12 months, at least 15 months, at least 18 months, at least 21 months, or at least 24 months.

In related embodiments, the both the citrate buffered and acetate buffered formulations provided herein demonstrate low to undetectable levels of aggregation. In some embodiments, the formulation contains no more than about 5%, no more than about 4%, no more than about 3%, no more than about 2%, no more than about 1% and no more than about 0.5% aggregation by weight of protein as measured by gel permeation high-performance liquid chromatography (GP-HPLC), SEC-HPLC, or static light scattering (SLS) techniques. In certain embodiments, at least 95% of the anti-CD200 antibody molecules in the formulation are present as a monomer at 2-8° C. for 24 months. In some embodiments, at least 97% of the anti-CD200 antibody molecules in the formulation are present as a monomer at 2-8° C. for 24 months. In some embodiments, at least 98% of the anti-CD200 antibody molecules in the formulation are present as a monomer at 2-8° C. for 24 months.

V. FORMULATION PREPARATION

The citrate and acetate buffered formulations provided herein were prepared by standard pharmaceutical laboratory methods, i.e., where the anti-CD200 antibody is initially anion exchange column purified, subsequently concentrated via tangential flow filtration to the desired concentration in the buffered solution.

The formulations of the invention may be sterilized by various sterilization methods, including sterile filtration, radiation, etc. In one embodiment, the antibody formulation is filter-sterilized with a presterilized 0.22-micron filter. Sterile compositions for injection can be formulated according to conventional pharmaceutical practice as described in "*Remington: The Science & Practice of Pharmacy*", 21st ed., Lippincott Williams & Wilkins, (2005). Formulations comprising antibodies, such as those disclosed herein, ordinarily will be stored in lyophilized form or in solution. It is contemplated that sterile compositions comprising antibodies are placed into a container having a sterile access port, for example, an intravenous solution bag or vial having an adapter that allows retrieval of the formulation, such as a stopper pierceable by a hypodermic injection needle.

VI. ADMINISTRATION

The formulation is administered to a mammal in need of treatment with the anti-CD200 antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In certain embodiments, the formulation is administered to the mammal by intravenous administration. For such purposes, the formulation may be injected using a syringe or via an IV line, for example. In certain embodiments, administration of the citrate buffered formulations provided herein is by intravenous administration, e.g., intravenous infusion. In other embodiments, the formulation is administered to the mammal by subcutaneous administration. In certain embodiments, administration of the acetate buffered formulations provided herein is by subcutaneous administration.

The appropriate dosage ("therapeutically effective amount") of the anti-CD200 antibody will depend, for example, on the condition to be treated, the severity and course of the condition, whether the antibody is administered for preventive or therapeutic purposes. Other factors can include, e.g., other medical disorders concurrently or previously affecting the subject, the general health of the subject, the genetic disposition of the subject, diet, time of administration, rate of excretion, drug combination, and any other additional therapeutics that have been previously or concurrently administered to the subject. It should also be understood that a specific dosage and treatment regimen for any particular subject will depend upon the judgment of the treating medical practitioner (e.g., doctor or nurse). The anti-CD200 antibody is suitably administered to the patient at one time or over a series of treatments and may be administered to the patient at any time from diagnosis onwards. In some embodiments, an anti-CD200 antibody is for use, and formulated as such, as a monotherapy. In some embodiments, an anti-CD200 antibody can be formulated with, or for use with, one or more additional active agents.

Dosage regimens comprising a formulation as described herein are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, in some embodiments, the formulations provided herein may be administered once or twice weekly by intravenous injection or once or twice monthly by intravenous injection. In other embodiments. In other embodiments, subcutaneous administration—or a more localized or depot delivery—of an anti-CD200 antibody to a mammal can be as effective as systemic delivery of the antibody (e.g., to prolong the survival of an allograft organ, e.g., kidney or heart).

The liquid formulations provided herein can be administered as a fixed dose of anti-CD200 antibody, or in a milligram per kilogram (mg/kg) dose. While in no way intended to be limiting, dosages of the anti-CD200 antibody include, e.g., 1-100 µg/kg, 0.5-50 µg/kg, 0.1-100 µg/kg, 0.5-25 µg/kg, 1-20 µg/kg, and 1-10 µg/kg, 1-100 mg/kg, 0.5-50 mg/kg, 0.1-100 mg/kg, 0.5-25 mg/kg, 1-20 mg/kg, and 1-10 mg/kg. Exemplary dosages of an anti-CD200 antibody formulation described herein include, without limitation, 0.1 µg/kg, 0.5 µg/kg, 1.0 µg/kg, 2.0 µg/kg, 4 µg/kg, and 8 µg/kg, 0.1 mg/kg, 0.5 mg/kg, 1.0 mg/kg, 2.0 mg/kg, 4 mg/kg, and 8 mg/kg.

In some embodiments, the formulations can be prepared in dosage unit form for ease of administration and uniformity of dosage. "Dosage unit form," as used herein refers to physically discrete units suited as unitary dosages for the subject to be treated; each unit dosage containing a predetermined quantity of comprising an anti-CD200 antibody (e.g., samalizumab) calculated to produce the desired therapeutic effect in a liquid formulation provided herein, e.g., a quantity calculated to provide an amount sufficient for a single cycle of administration.

The formulations provided herein may also be combined with one or more other therapeutic agents as necessary for the particular indication being treated, preferably those with complementary activities that do not adversely affect the antibody of the formulation. Such therapeutic agents are suitably present in combination in amounts that are effective for the purpose intended. Accordingly, in some embodiments, the formulations provided herein contain a sub-therapeutic amount of the anti-CD200 antibody or antigen binding fragment thereof and a sub-therapeutic amount of one or more additional active agents such that the components in total are therapeutically effective for treating the particular disease or disorder, for example, according to the treatment methods described herein. Additional therapeutic agents which can be combined with the formulation of the invention are further described herein.

VII. KITS AND ARTICLES OF MANUFACTURE

In a related aspect, provided herein is an article of manufacture with a container which holds the liquid formulations disclosed herein. Suitable containers include, for example, bottles, vials and syringes. The container may be formed from a variety of materials such as glass or plastic. In some embodiments, the container is a 3-20 cc single use glass vial. In other embodiments, e.g., for a multidose formulation, the container may be 3-100 cc glass vial.

In some embodiments, the article of manufacture can contain a syringe pre-filled with the liquid formulation (e.g., a pen device containing the solution) described herein or can contain a pump (e.g., an osmotic pump) and one or more disposable cassettes configured for use with the pump, the cassettes pre-filled with an liquid solution described herein. In some embodiments, the means for delivering the high concentration solution is a pen device for drug delivery. In some embodiments, the container may hold a formulation as described herein, and may have a sterile access port (for example the container may be an intravenous solution bag or a vial having a stopper pierceable by a hypodermic injection needle). In certain embodiments, the container excludes UV light.

In some embodiments, a doser such as the doser device described in U.S. Pat. No. 6,302,855 may also be used. For example, a dosage mechanism such as a rotatable knob allows the user to accurately adjust the amount of medication that will be injected by the pen from a prepackaged vial of medication. To inject the dose of medication, the user inserts the needle under the skin and depresses the knob once as far as it will depress. The pen may be an entirely mechanical device or it may be combined with electronic circuitry to accurately set and/or indicate the dosage of medication that is injected into the user (See, e.g., U.S. Pat. No. 6,192,891). In some embodiments, the needle of the pen device is disposable and the kits include one or more disposable replacement needles. Pen devices suitable for delivery of the any one of the presently featured antibody solutions are also described in, e.g., U.S. Pat. Nos. 6,277,099; 6,200,296; 6,146,361; and 7,556,615.

In some embodiments, the container holds the formulation and the label on, or associated with, the container may indicate directions for use. The article of manufacture may further include other materials desirable from a commercial and user standpoint, including other buffers, diluents, filters, needles, syringes, and package inserts with instructions for use.

The formulations described herein also can be provided in a kit, a packaged combination of reagents in predetermined amounts with instructions for use in the methods described herein. For example, in some embodiments, the kits comprise a formulation as described herein include instructions, e.g., comprising administration parameters including dosages and infusion rates, to allow a practitioner (e.g., a physician, nurse, or patient) to administer the formulation contained therein to a patient having cancer, an autoimmune disorder or an allograft in accordance with the methods disclosed herein. In one embodiment, the kit further comprises an additional therapeutic agent. In another embodiment, the additional therapeutic agent comprises an immunomodulatory compound, vaccine or chemotherapy.

VIII. METHODS OF USE

Provided herein are methods for treating cancer, autoimmune disorders and for preventing or inhibiting allograft rejection by administering a formulation disclosed herein comprising an effective amount of an anti-CD200 antibody or antigen binding fragment thereof to a subject in need thereof. In some embodiments, the disease or disorder is associated with the upregulation of OX-2/CD200.

A. Cancer

In one aspect, provided are methods of treating cancer by administering the liquid formulation provided herein to a subject in need thereof. Methods of using anti-CD200 antibodies for the treatment of cancer have been described, for example, in U.S. Pat. Nos. 7,435,412; 8,709,415; and 9,085,623.

Cancers for which the disclosed methods may be used include but are not limited to lung cancer (e.g., small-cell lung cancer, non-small cell lung cancer), breast cancer, colon cancer, colorectal cancer, pancreatic cancer, kidney cancer, gastric cancer, salivary gland carcinoma, liver cancer (e.g., hepatic carcinoma), bone cancer, hematological cancer, neural tissue cancer (e.g., neuroblastoma), glial cell tumors such as glioblastoma and neurofibromatosis, melanoma, thyroid cancer, endometrial carcinoma, ovarian cancer, testicular cancer, prostate cancer, cervical cancer, vaginal cancer, bladder cancer and various types of head and neck cancer. Also included are cancers derived from neural crest cells and any cancers that express CD200.

In certain embodiments, this disclosure provides a method for treating hematological malignancies, such as, for example, a lymphoma, leukemia, myeloma or a lymphoid malignancy, as well as a cancer of the spleen and the lymph nodes. Exemplary lymphomas include both B cell lymphomas and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological cancers also include leukemia, such as, but not limited to, secondary leukemia, chronic lymphocytic leukemia (CLL), acute myelogenous leukemia (AML), chronic myelogenous leukemia (CML), and acute lymphoblastic leukemia (ALL). Hematological cancers further include myelomas, such as, but not limited to, multiple myeloma and smoldering multiple myeloma. Other hematological and/or B cell- or T-cell-associated cancers are encompassed by the term hematological cancer.

In some embodiments, the subject treating according to the methods provided herein has a tumor or hematological malignancy comprising cancer cells overexpress CD200 relative to normal cells of the same histological type as the cells from which the cancer cells are derived. Methods of determining the expression of CD200 are well-known and described, for example, in U.S. Pat. Nos. 7,435,412; 8,709,415; and 9,085,623.

In particular embodiments, provided herein are methods of treating chronic lymphocytic leukemia by administering a liquid formulation comprising an anti-CD200 antibody (e.g., samalizumab) or antigen binding fragment thereof as disclosed herein. "CLL", as used herein, refers to chronic lymphocytic leukemia involving any lymphocyte, including but not limited to various developmental stages of B cells and T cells, including but not limited to B cell CLL. B-CLL, as used herein, refers to leukemia with a mature B cell phenotype which is $CD5^+$, $CD23^+$, $CD20^{dim+}$, $sIg^{dim+}$ and arrested in G0/G1 of the cell cycle.

In certain embodiments, a patient can have a cancer that is suspected of being resistant or is likely to become resistant to an anti-CD20 therapy. One biomarker useful in assessing whether a cancer is likely to become resistant to an anti-CD20 therapeutic agent such as rituximab is the presence or concentration of $CD5^+$ cancer cells in the population (see, U.S. Pat. No. 9,085,623). In some embodiments, the anti-CD20 therapeutic agent is an anti-CD20 antibody such as, but not limited to, rituximab, ofatumumab, TRU-015, veltuzumab, ocrelizumab, or AME-133v. In some embodiments, the methods comprise treating a subset of CLL patients that are refractory to treatment with anti-CD20 therapy (e.g., rituximab-resistant).

For instance, the formulations described herein can be administered as a therapeutic to cancer patients or autoimmune disease patients, especially, but not limited to CLL patients.

The anti-CD200 antibody formulations provided herein can also be administered in combination with other immunomodulatory compounds, vaccines or chemotherapy. As used herein, adjunctive or combined administration (coadministration) includes simultaneous administration of the formulation with the immunomodulatory compound, vaccine or chemotherapy, in the same or different dosage form, or separate administration of the compounds (e.g., sequential administration). Thus, the anti-CD200 formulation and immunomodulatory compounds, vaccines or chemotherapy, can be simultaneously administered in a single formulation. Alternatively, the anti-CD200 formulation and immunomodulatory compounds, vaccines or chemotherapy, can be formulated for separate administration and are administered concurrently or sequentially.

Illustrative examples of suitable immunomodulatory therapies include the administration of agents that block negative regulation of T cells or antigen presenting cells (e.g., anti-CTLA4 antibodies, anti-PD-L1 antibodies, anti-PDL-2 antibodies, anti-PD-1 antibodies and the like) or the administration of agents that enhance positive co-stimulation of T cells (e.g., anti-CD40 antibodies or anti 4-1BB antibodies). Furthermore, immunomodulatory therapy could be cancer vaccines such as dendritic cells loaded with tumor cells, tumor RNA or tumor DNA, tumor protein or tumor peptides, patient derived heat-shocked proteins (hsp's) or general adjuvants stimulating the immune system at various levels such as CpG, Luivac, Biostim, Ribominyl, Imudon, Bronchovaxom or any other compound activating receptors of the innate immune system (e.g., toll like receptors). Also, immunomodulatory therapy could include treatment with cytokines such as IL-2, GM-CSF and IFN-gamma.

Accordingly in some embodiments, the methods of treatment provided herein enhance the immune response to cancer cells by the administration of the anti-CD200 formulation provided herein, alone or in combination with one of the previously mentioned immunomodulatory therapies. For example, in certain embodiments, the formulations provided herein may be used in combination with a monoclonal antibody (e.g., rituximab, trastuzumab, alemtuzumab, cetuximab, or bevacizumab), including a conjugated monoclonal antibody (e.g., gemtuzumab ozogamicin, ibritumomab tiuxetan, or tositumomab).

In other embodiments, existing regulatory T cells are eliminated with reagents such as anti-CD25 or cyclophosphamide before starting anti-CD200 treatment. Also, therapeutic efficacy of myeloablative therapies followed by bone marrow transplantation or adoptive transfer of T cells reactive with CLL cells is enhanced by treatment with the anti-CD200 formulations described herein. Furthermore, treatment with the anti-CD200 formulations can substantially enhance efficacy of cancer vaccines such as dendritic cells loaded with CLL cells or proteins, peptides or RNA derived from such cells, patient-derived heat-shocked proteins, tumor peptides or protein. In other embodiments, the anti-CD200 formulation is used in combination with an immuno-stimulatory compound, such as CpG, toll-like receptor agonists or any other adjuvant, anti-CTLA-4 antibodies, and the like. In other embodiments, efficacy of the anti-CD200 formulation is improved by blocking of immunosuppressive mechanisms with, e.g., anti-PDL1 and/or 2 antibodies, anti-PD1 antibodies, anti-IL-10 antibodies, or anti-IL-6 antibodies. In yet other embodiments, efficacy of an anti-CD200 formulation is improved by administration of agents that increase NK cell number or T-cell, e.g., the small molecule inhibitor IMiDs, thalidomide, or thalidomide analogs. In certain embodiments, the methods described herein further comprise administering one or more additional therapeutics with the anti-CD200 formulation, for example, Non-limiting examples of cytotoxic compounds include therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Furthermore, the combined administration of the anti-CD200 formulation with chemotherapeutics could be particularly useful to reduce overall tumor burden, to limit angiogenesis, to enhance tumor accessibility, to enhance susceptibility to ADCC, to result in increased immune function by providing more tumor antigen, or to increase the expression of the T cell attractant LIGHT. When the anti-CD200 formulation is administered to a subject in combination with another conventional anti-neoplastic agent, either concomitantly or sequentially, anti-CD200 formulation may be shown to enhance the therapeutic effect of either agent alone. These chemotherapeutic anti-tumor compounds may be categorized by their mechanism of action into groups, including, for example, the following classes of agents: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prenisolone); growth factor signal transduction kinase inhibitors; mitochondrial dysfunction inducers and caspase activators; and chromatin disruptors.

B. Autoimmune Disorders

In another aspect, the disclosure relates to methods of treating patients with autoimmune disorders by administering a liquid formulation provided herein to a subject in need thereof. Methods of treating autoimmune disorders by administering an anti-CD200 antibody or fragment thereof are described for example, in U.S. Pat. Nos. 8,637,014 and 9,085,623.

Examples of autoimmune disease include but are not limited to, psoriasis, pancreatitis, type I diabetes (IDDM), Graves' Disease, inflammatory bowel disease (IBD), Crohn's Disease, ulcerative colitis, irritable bowel syndrome, multiple sclerosis, rheumatoid arthritis, reactive arthritis, enteropathic arthritis, spondyloarthropathy, autoimmune myocarditis, Kawasaki disease, celiac disease, uveitis, Behcet's disease, coronary artery disease, chronic obstructive pulmonary disease (COPD), interstitial lung disease, inflammatory muscle disease (polymyositis, dermatomyositis), microscopic polyangiitis, autoimmune aplastic anemia, autoimmune thyroiditis, autoimmune hepatitis, Wegener's syndrome, diverticulosis, systemic lupus erythematosus, ankylosing spondylitis, scleroderma, systemic sclerosis, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, autoimmune nephritis, pemphigus vulgaris, myasthenia gravis, autoimmune hearing loss, neuromyelitis optica, Goodpasture's syndrome, cryoglobulinemia, Guillain Barre syndrome, chronic inflammatory demyelinating polyneuropathy (CIDP), autoimmune hemolytic anemia, idiopathic thrombocytopenic purpura (ITP), CAD (or cold hemagglutinin disease or CHD/CHAD), transplant rejection, PCH (known as the "Donath-Landsteiner antibody"), MG (express antibodies to nicotinic acetylcholine receptor, AChR), highly sensitized transplant patients, antiphospholipid syndrome, allergy, and asthma, and other autoimmune diseases, or other diseases mediated by CD200.

A human "at risk of developing an autoimmune disorder" refers to a human with a family history of autoimmune disorders (e.g., a genetic predisposition to one or more inflammatory disorders) or one exposed to one or more autoimmune disorder/autoantibody-inducing conditions. For example, a human exposed to a shiga toxin is at risk for developing typical HUS. Humans with certain cancers (e.g., liquid tumors such as multiple myeloma or chronic lymphocytic leukemia) can pre-dispose patients to developing certain autoimmune hemolytic diseases. For example, PCH can follow a variety of infections (e.g., syphilis) or neoplasms such as non-Hodgkin's lymphoma. In another example, CAD can be associated with HIV infection, *Mycoplasma pneumonia* infection, non-Hodgkin's lymphoma, or Waldenstrom's macroglobulinemia. In yet another example, autoimmune hemolytic anemia is a well-known complication of human chronic lymphocytic leukemia, approximately 11% of CLL patients with advanced disease will develop AIHA. As many as 30% of CLL may be at risk for developing AIHA. See, e.g., Diehl et al. *Semin Oncol* 25(1):80-97 (1998) and Gupta et al. *Leukemia* 16(10):2092-2095 (2002). From the above it will be clear that humans "at risk of developing an autoimmune disorder" are not all the humans within a species of interest.

A human "suspected of having an autoimmune disorder" is one who presents with one or more symptoms of an autoimmune disorder. Symptoms of autoimmune disorders can vary in severity and type with the particular autoimmune disorder and include, but are not limited to, redness, swelling (e.g., swollen joints), joints that are warm to the touch, joint pain, stiffness, loss of joint function, fever, chills, fatigue, loss of energy, pain, fever, pallor, icterus, urticarial dermal eruption, hemoglobinuria, hemoglobinemia, and anemia (e.g., severe anemia), headaches, loss of appetite, muscle stiffness, insomnia, itchiness, stuffy nose, sneezing, coughing, one or more neurologic symptoms such as dizziness, seizures, or pain. From the above it will be clear that not all humans are "suspected of having an autoimmune disorder."

Methods for detecting the presence or amount of an autoimmune disorder-associated autoantibody in a human are well known in the art and are described in, e.g., Burbelo et al. (2009) *J Transl Med* 7:83; Hanke et al. (2009) *Arthritis Res Ther* 11(1):R22; Hoch et al. (2001), supra; Vernino et al. (2008) *J Neuroimmunol* 197(1):63-69; Sokol et al. (1982), supra; and Littleton et al. (2009) *Mol Cell Proteomics* 8(7):1688-1696.

In some embodiments, the anti-CD200 antibody formulation is administered to a subject in an amount and with a frequency to maintain a reduced concentration (or a reduced expression or production) of the autoimmune disorder-associated autoantibody. Methods for detecting expression or a change in concentration of autoantibodies are well known in the art (e.g., Western blot, immunohistochemistry, and flow cytometry techniques) and described herein. Through an iterative process, a medical practitioner can determine the appropriate dose amount, and frequency of administration of each dose, required to maintain a reduced concentration of the autoimmune disorder-associated autoantibodies in the patient. For example, a medical practitioner can administer to a patient with an autoimmune disorder such as AIHA one or more (e.g., one, two, three, four, five, six, seven, eight, nine, or 10 or more or, e.g., at least two, at least three, four, five, six, seven, or eight or more) times the liquid formulation provided herein comprising the anti-CD200 antibody or antibody fragment thereof (e.g., samalizumab) in an amount that reduces (or is at least expected to reduce) the concentration of autoantibodies in the human. The at least two doses should be spaced apart in time by at least one (e.g., at least two, three, four, five, six, seven, eight, nine, 10, 11, 12, 13, or even 14) day(s). Biological samples (e.g., blood samples) containing the autoantibodies are obtained from the patient at various times, e.g., prior to the first anti-CD200 antibody administration, between the first dose and at least one additional dose, and at least one biological sample collection following the second dose. In some embodiments, biological samples may be collected at least two times between doses and/or at least one time after the final dose administered to the patient. The autoantibodies in each biological sample obtained are then interrogated for relative titer of the autoimmune-disease associated autoantibody to determine whether the amount and/or the frequency of administration of the anti-CD200 antibody are sufficient to maintain a reduced concentration of the autoantibody in the patient. The medical practitioner (and/or a computer) can determine an anti-CD200 antibody dosing schedule for the patient that is sufficient to maintain a reduced concentration of autoimmune disorder-associated autoantibodies in the patient over the course of the treatment.

In some embodiments, administration of the anti-CD200 antibody formulation to the human reduces the autoantibody concentration by at least 5 (e.g., at least 6, 7, 8, 9, 10, 11, 12, 13, 14, 15, 16, 17, 18, 19, 20, 25, 30, 35, 40, 45, 50, 55, 60, 65, 70, 75, 80, or 85 or more) %. In some embodiments, the anti-CD200 antibody can be chronically administered to the human. For example, an anti-CD200 antibody can be chronically administered a patient with MG to maintain a reduced concentration of anti-AChR antibodies in the blood of the patient for a prolonged period of time. Accordingly, a patient chronically treated with an anti-CD200 antibody formulation can be treated for a period of time that is greater than or equal to 2 weeks (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life).

An anti-CD200 antibody formulation described herein can be co-administered with one or more additional therapeutic agents useful for treating or preventing an inflammatory condition. The one or more agents include, e.g., a non-steroidal anti-inflammatory drug (NSAID), a disease-modifying anti-rheumatic drug (DMARD), a biological response modifier, or a corticosteroid. Biological response modifiers include, e.g., an anti-TNF agent (e.g., a soluble TNF receptor or an antibody specific for TNF such as adulimumab, infliximab, or etanercept). In some embodiments, the one or more additional therapeutic agents can be, e.g., steroids, anti-malarials, aspirin, non-steroidal anti-inflammatory drugs, immunosuppressants, cytotoxic drugs, corticosteroids (e.g., prednisone, dexamethasone, and prednisolone), methotrexate, methylprednisolone, macrolide immunosuppressants (e.g., sirolimus and tacrolimus), mitotic inhibitors (e.g., azathioprine, cyclophosphamide, and methotrexate), fungal metabolites that inhibit the activity of T lymphocytes (e.g., cyclosporine), mycophenolate mofetil, glatiramer acetate, and cytotoxic and DNA-damaging agents (e.g., chlorambucil or any other DNA-damaging agent described herein or known in the art).

In some embodiments, the anti-CD200 formulation may be combined with antibody treatments including daclizumab, a genetically engineered human IgG1 monoclonal antibody that binds specifically to the α-chain of the interleukin-2 receptor, as well as various other antibodies targeting immune cells or other cells. Such combination therapies may be useful in the treatment of type 1 diabetes, rheumatoid arthritis, lupus, and idiopathic thrombocytopenic purpura, and other autoimmune indications.

C. Cell and Tissue Transplants

Further provided are methods of inhibiting an immune response to a tissue or cell transplant in a subject by administering an anti-CD200 antibody formulation as provided herein. Methods of inhibiting allograft rejection using anti-CD200 antibodies have been described, for example, in U.S. Pat. No. 8,252,285 and US 2014/0170143.

The formulations as described herein may be used to inhibit or prevent a humoral immune response in recipients of various kinds of transplanted cells, tissues, and organs. For example, a graft may be autologous, allogeneic, or xenogeneic to the recipient. The graft may be a cell, tissue, or organ graft, including, but not limited to, bone marrow grafts, peripheral blood stem cell grafts, skin grafts, arterial and venous grafts, pancreatic islet cell grafts, and transplants of the kidney, liver, pancreas, thyroid, and heart. In one embodiment, the autologous graft is a bone marrow graft, an arterial graft, a venous graft, or a skin graft. In another embodiment, the allograft is a bone marrow graft, a corneal graft, a kidney transplant, a heart transplant, a liver transplant, a lung transplant, a pancreatic transplant, a pancreatic islet cell transplant, or a combined transplant of a kidney and pancreas. In another embodiment, the graft is a xenograft, preferably wherein the donor is a pig. Further, an anti-CD200 antibody, used alone or in combination with a second agent, may also be used to suppress a deleterious immune response to a non-biological graft or implant, including, but not limited to, an artificial joint, a stent, or a pacemaker device.

In certain embodiments, the graft recipient is a recipient of a hematopoietic cell or bone marrow transplant, an allogeneic transplant of pancreatic islet cells, or a solid organ transplant selected from the group consisting of a heart transplant, a kidney-pancreas transplant, a kidney transplant, a liver transplant, a lung transplant, and a pancreas transplant. Additional examples of grafts include but are not limited to allotransplanted cells, tissues, or organs such as vascular tissue, eye, cornea, lens, skin, bone marrow, muscle, connective tissue, gastrointestinal tissue, nervous tissue, bone, stem cells, cartilage, hepatocytes, or hematopoietic cells.

In some embodiments, provided are methods for the treatment and prevention of graft versus host disease (GVHD) and graft rejection in patients by administering a liquid formulation comprising an anti-CD200 antibody or antigen binding fragment thereof as provided herein. In some embodiments, the formulations can be used in methods for treating or preventing an acute or a chronic humoral rejection in a transplant recipient. In other embodiments, the formulations can be used in methods of treating patients who have received or will receive a transplant (e.g., a xenotransplant or allotransplant).

In some embodiments, the liquid formulations of the present disclosure may be administered to a patient prior to a transplant or allograft procedure, or after the procedure in order to decrease or eliminate CD200-positive immune cells that could reduce acceptance of the transplanted organ, tissue, or cell. In certain embodiments where the graft recipient is human, an allograft may be MHC mismatched. In certain embodiments, the MHC mismatched allograft is an HLA mismatched allograft. In further embodiments, the recipient is ABO mismatched to the allograft.

In some embodiments, a method of prolonging or promoting graft survival by administering an anti-CD200 antibody formulation as provided herein increases graft survival in the recipient by at least about 15%, by at least about 20%, by at least about 25%, by at least about 30%, by at least about 40%, or by at least about 50%, compared to the graft survival observed in a control recipient. A control recipient may be, for example, a graft recipient that does not receive a therapy post-transplant or that receives a monotherapy following transplant.

In some embodiments, the anti-CD200 antibody formulation is administered to the recipient mammal for at least seven (e.g., at least eight, nine, 10, 11, 12, 13, 14, 15, 16, 17, 18, 19, 20, 21, 22, 23, 24, 25, 26, 27, 28, 29, 30, 31) days following transplantation of the allograft into the recipient mammal. In some embodiments, the anti-CD200 antibody formulation is administered at least once per day for up to seven (e.g., up to eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) days following transplantation of the allograft into the recipient mammal. In some embodiments, the anti-CD200 antibody formulation is administered at least once per day for at least seven, but less than 30 (e.g., less than 29, 28, 27, 26, 25, 24, 23, 22, 21, 20, 19, 18, 17, 16, 15, 14, 13, 12, 11, 10, 9, or 8) days following transplantation of the allograft into the recipient mammal. In some embodiments of any of the methods described herein, anti-CD200 antibody formulation is administered to the recipient mammal once every two days. In some embodiments of any of the methods described herein, the anti-CD200 antibody formulation can be administered at least once a week. In some embodiments of any of the methods described herein, the anti-CD200 antibody formulation can be administered at least once every two weeks (e.g., at least once every 12, 13, 14, 15, or 16 days).

In certain embodiments, a method of promoting graft survival by administering the anti-CD200 antibody formulation promotes long-term graft survival, wherein the long-term graft survival is selected from among: at least about 6 months post-transplant, at least about 1 year post transplant; at least about 5 years post transplant; at least about 7.5 years post-transplant; and at least about 10 years post-transplant. In certain embodiments, the therapies described herein promote accommodation of the graft and the graft survives for the remaining life-time of the recipient.

In some embodiments, the anti-CD200 antibody formulation is therapeutically effective as a single-agent therapy (such therapy is also referred to herein as a "monotherapy") to substantially prolong the survival of an allograft (e.g., a renal transplant) in the transplant recipient.

In other embodiments, a liquid formulation of the present disclosure, is used in combination with lower doses of traditional therapeutic drugs than would be possible in the absence of the anti-CD200 antibody. In another embodiment, the formulations and methods of the disclosure obviate the need for a more severe form of therapy, such as radiation therapy, high-dose immunomodulatory therapy, or splenectomy. Combination treatments are discussed in more detail in the previous section related to autoimmune disorders and include, for example, adriamycin, azathiopurine, busulfan, cyclophosphamide, cyclosporine A, Cytoxan, fludarabine, 5-fluorouracil, methotrexate, mycophenolate mofetil, a nonsteroidal anti-inflammatory, rapamycin, sirolimus, and tacrolimus. Other examples include antibodies such as, e.g., OKT3™ (muromonab-CD3), CAMPATH™-1G, CAMPATH™-1H (alemtuzumab), or CAMPATH™-1M, SIMULEC™ (basiliximab), ZENAPAX™ (daclizumab), RITUXAN™ (rituximab), and anti-thymocyte globulin.

In some embodiments, an immunomodulatory treatment method such as plasmapheresis, splenectomy, or immunoadsorption, can be used in combination with the anti-CD200 antibody formulation. In embodiments where the anti-CD200 antibody formulation is administered to a transplant recipient to inhibit a humoral immune response, the anti-CD200 antibody formulation may be administered to a transplant recipient prior to or following transplantation, alone or in combination with one or more therapeutic agents or regimens for the treatment or prevention of GVHD and graft rejection. For example, an anti-CD200 antibody formulation may be used to deplete alloantibodies from a transplant recipient prior to or following transplantation of an allogeneic graft.

In additional embodiments of inhibiting graft rejection, the immunomodulatory or immunosuppressive agent is selected from the group consisting of adriamycin, azathiopurine, busulfan, cyclophosphamide, cyclosporine A, fludarabine, 5-fluorouracil, methotrexate, mycophenolate mofetil, 6-mercaptopurine, a corticosteroid, a nonsteroidal anti-inflammatory, sirolimus (rapamycin), and tacrolimus (FK-506). In alternative embodiments, the immunomodulatory or immunosuppressive agent is an antibody selected from the group consisting of muromonab-CD3, alemtuzumab, basiliximab, daclizumab, rituximab, anti-thymocyte globulin and IVIg.

In particular embodiments, an anti-CD200 antibody formulation is administered in conjunction with an inhibitor of cellular immune function. Such inhibitors include but are not limited to cyclosporine A, tacrolimus, rapamycin, anti-T cell antibodies, daclizumab, and muromonab-CD3. As demonstrated in the present disclosure, a combination of an anti-CD200 antibody and an inhibitor of cellular immune function increases survival of a graft compared to the survival observed in a control graft recipient (e.g., a recipient receiving no treatment or a recipient receiving monotherapy, such as an inhibitor of cellular immune function). Increased survival includes, for example, at least about 15%, at least about 20%, at least about 25%, at least about 30%, at least about 40%, or at least about 50% increase in survival time (measured in days, months, or years, for example).

The following examples are merely illustrative and should not be construed as limiting the scope of this disclosure in any way as many variations and equivalents will become apparent to those skilled in the art upon reading the present disclosure.

Example 1

Formulations containing samalizumab, containing 12.5 mM histidine, 12.5 mM glycine, 150 mM NaCl, 5% mannitol, 0.02% Polysorbate 80 at pH 6.0, which were used in early clinical trials demonstrated instability (i.e., precipitated out of solution) at low temperatures (i.e., 2-8° C.). In addition, this formulation demonstrated an osmolality of greater than 600 mOsm/kg, which is undesirable as an intravenous therapeutic. Accordingly, alternative formulations were investigated to identify improved formulations of samalizumab which comply with clinical criteria for efficacy and which are stable for under standard production, storage and shipping conditions.

Materials and Methods

A twenty-four (24) month formulation stability study was conducted to identify improved anti-CD200 antibody formulations containing samalizumab, citrate buffer, a polyol (i.e., mannitol), a surfactant (i.e., polysorbate 80), and a tonicity agent (i.e., NaCl).

The formulations were prepared by standard pharmaceutical laboratory methods in which the anti-CD200 antibody is initially anion exchange column purified, subsequently concentrated via tangential flow filtration to approximately 8 g/L into the desired buffer, e.g., 50 mM Na citrate with NaCl at pH 5.2. Mannitol is added with mixing as an 18% (w/v) citrate buffer solution to the sample to make up the desired mannitol concentration. Polysorbate is added as a 10% aqueous solution with stirring to make the desired concentration. All steps were performed at room temperature (approx. 18-25° C.). Samples were then diluted to 5 mg/ml or 10 mg/ml with the appropriate solution. Samples were stored (after sterile filtration) into one of polypropylene tubes, polystyrene bottles, or process bags at 2-8° C.

This study assessed forty-eight (24×5 mg/mL and 24×10 mg/mL) formulations prepared with 50 mM citrate containing NaCl, mannitol and polysorbate 80 (summarized in Table 1). Samalizumab was obtained from a fractogel pool generated according to established procedures and stored at −80° C., and the excipients were obtained from standard commercial sources. All sample formulations were stored in 4 mL polypropylene screw cap bottles at 2-8° C.

TABLE 1

| Citrate buffer formulation conditions 50 mM Citrate, 0.02% Polysorbate 80 | | | | |
|---|---|---|---|---|
| NaCl | 150 mM | 75 mM | | |
| pH | 5.75 | 5.50 | 5.25 | 5.00 |
| Mannitol | 0 | 1% | 3% | |
| Protein (mg/mL) | 5 | 10 | | |

Formulations were tested for appearance by visual inspection and GP-HPLC at T=0, 1, 2, 3, 6, 9, 12, 15 and 24 months. Densitometry by SDS-PAGE, isoelectric focusing (IEF), size exclusion chromatography and osmolality testing were performed at T=0, 6, 12, 18 and 24 months.

Gel permeation (size exclusion) HPLC was used to distinguish monomeric IgG from aggregates consisting of dimeric or larger species. Test samples were injected onto a TSK gel G3000 SWXL column equilibrated in 0.3 M NaCl, 10 mM sodium phosphate, pH 6.0. Protein peaks were monitored at 214 nm and analyzed. The percent purity of the monomer is reported as a percentage of the total integrated peak area.

SDS PAGE (Coomassie), Reduced and Non Reduced was used to test the homogeneity and purity of the product. Samples were denatured by treatment with sodium dodecyl sulfate and the disulfide bonds were disrupted with dithiothreitol (reducing conditions). Polypeptides were separated according to subunit molecular size by electrophoresis through 4.0-20.0% w/v precast SDS PAGE gels and visualized by staining with Coomassie blue. Polypeptide bands were quantified by laser densitometry. A non reduced gel was run using the same method with the omission of dithiothreitol.

Osmolality—sample osmolality was determined using a freezing point depression osmometer. The osmometer was calibrated prior to use with commercially available, certified osmolality standards bracketing the sample range. A reference solution was used to confirm successful calibration prior to testing samples. Samples were tested in triplicate and the results must not differ by more than 3% RSD. The value reported is the mean of the three results.

Protein Concentration (A280)—absorbance at 280 nm was used to determine the protein concentration in the test sample using a theoretically determined extinction coefficient of 1.408. The test sample was suitably diluted to give an absorbance reading in the working range of the assay (0.2 to 0.85 absorbance units). The absorbance of triplicate samples was measured and results must not differ by more than 3% RSD. The value reported is the mean of the three independent measurements. Spectrophotometers used for these determinations were calibrated against metal on quartz filters traceable by the National Institute of Standards and Technology (NIST).

Isoelectric Focusing (IEF) Analysis was performed using a flat-bed electrophoresis system. Precast agarose gels covering a range of pH 7.0 to pH 11.0 were employed. Samples were loaded onto the gel at a predetermined optimized load position. Following focusing for a set number of volt hours, separated charge variants were visualized using Coomassie blue. Gels were scanned using a densitometer and the pI of bands calculated.

Analysis of Visual Appearance

Solubility of samalizumab at 2-8° C. was monitored by a visual appearance inspection of all formulations at T=0, 1, 2, 3, 6, 9, 11, 12, 15, 18 and 24 months. Appearance results showed samples were clear and colorless (CC) and free of visible particles up to T=2 months. Precipitation was first observed at T=3 months in 10 mg/mL formulations containing no mannitol at pH 5.75. The appearance data at T=11 months indicated that concentrations of >1% polyol (e.g., mannitol) is necessary for maintaining solubility at pH ranges from 5.75 to 5.25. In addition, lower pH formulations, pH 5.25 to 5.0 showed less precipitation than samples formulated at higher pH.

The appearance test performed on all formulations at 11 months indicated that an increasing number of 10 mg/ml formulations showed precipitation at 11 months (FIG. 2). These results suggest that concentrations of >1% mannitol are important for maintaining stability at pH ranges from 5.75 to 5.25. In addition, lower pH formulations, pH 5.25 to 5.00, showed less precipitation than higher pH formulated samples.

The 11 month appearance test also showed precipitation in the first 5 mg/mL formulation containing 50 mM Citrate, 75 mM NaCl and 0.02% Tween 80, pH 5.75. The absence of mannitol in this formulation further supports the importance of this excipient in maintaining solubility of samalizumab in theses formulations.

The appearance data from the 10 mg/mL formulation samples at 11 months was further evaluated using JMP statistical software. Formulations where precipitation was observed were assigned data values of 0 (zero), while clear and colorless formulations (no precipitation observed) were assigned data values of 1 (one). The results are provided in Table 2.

TABLE 2

| | | | | | | |
|---|---|---|---|---|---|---|
| | | | JMP Assignments | | | |
| Sample # | NaCl (mM) | Conc. (mg/mL) | pH | Mannitol (%) | 11M (Appearance) | JMP Assignments |
| 13 | 150 | 10 | 5.75 | 0 | Precipitated | 0 |
| 14 | 150 | 10 | 5.75 | 1 | Precipitated | 0 |
| 15 | 150 | 10 | 5.75 | 3 | Clear | 1 |
| 16 | 150 | 10 | 5.50 | 0 | Precipitated | 0 |
| 17 | 150 | 10 | 5.50 | 1 | Precipitated | 0 |
| 18 | 150 | 10 | 5.50 | 3 | Clear | 1 |
| 19 | 150 | 10 | 5.25 | 0 | Precipitated | 0 |
| 20 | 150 | 10 | 5.25 | 1 | Clear | 1 |
| 21 | 150 | 10 | 5.25 | 3 | Clear | 1 |
| 22 | 150 | 10 | 5.00 | 0 | Clear | 1 |
| 23 | 150 | 10 | 5.00 | 1 | Clear | 1 |
| 24 | 150 | 10 | 5.00 | 3 | Clear | 1 |
| 37 | 75 | 10 | 5.75 | 0 | Precipitated | 0 |
| 38 | 75 | 10 | 5.75 | 1 | Precipitated | 0 |
| 39 | 75 | 10 | 5.75 | 3 | Clear | 1 |
| 40 | 75 | 10 | 5.50 | 0 | Precipitated | 0 |
| 41 | 75 | 10 | 5.50 | 1 | Precipitated | 0 |
| 42 | 75 | 10 | 5.50 | 3 | Clear | 1 |
| 43 | 75 | 10 | 5.25 | 0 | Precipitated | 0 |
| 44 | 75 | 10 | 5.25 | 1 | Clear | 1 |
| 45 | 75 | 10 | 5.25 | 3 | Clear | 1 |
| 46 | 75 | 10 | 5.00 | 0 | Precipitated | 0 |
| 47 | 75 | 10 | 5.00 | 1 | Clear | 1 |
| 48 | 75 | 10 | 5.00 | 3 | Clear | 1 |

The results of a full factorial analysis of the JMP assignments are depicted in FIG. 1. The data indicate that the mannitol concentrations and pH are important parameters in maintaining solubility of samalizumab. In addition, the contour plot suggests a lower pH and higher mannitol concentrations would promote samalizumab solubility, while the concentration of NaCl would not have a substantial impact.

At 24 months, the appearance results of all formulations showed numerous formulations that did not exhibit precipitation at 2-8° C. throughout the testing period (see FIG. 2). It is evident from these results that 50 mM citrate plays a critical role in maintaining solubility. In addition, the 24 month results confirm the JMP statistical analysis indicating that lower pH (≤5.5) and higher mannitol concentrations (≥1%) are important parameters in maintaining solubility, while NaCl concentrations are less important for maintaining solubility.

Based on the results of the visual appearance tests, further evaluation focused on formulations 29, 30, 32, 33, 35, 36, 39, 42, 44, 45, 47 and 48. These formulations contain 1 and 3% mannitol, pH<5.50, and 75 mM NaCl as follows:

Formulation 29: 5 mg/mL samalizumab in 50 mM citrate, 75 mM NaCl, pH 5.50, 1% mannitol, 0.02% Tween 80;
Formulation 30: 5 mg/mL samalizumab in 50 mM citrate, 75 mM NaCl, pH 5.50, 3% mannitol, 0.02% Tween 80;
Formulation 32: 5 mg/mL samalizumab in 50 mM citrate, 75 mM NaCl, pH 5.25, 1% mannitol, 0.02% Tween 80;
Formulation 33: 5 mg/mL samalizumab in 50 mM citrate, 75 mM NaCl, pH 5.25, 3% mannitol, 0.02% Tween 80;
Formulation 35: 5 mg/mL samalizumab in 50 mM citrate, 75 mM NaCl, pH 5.00, 1% mannitol, 0.02% Tween 80;
Formulation 36: 5 mg/mL samalizumab in 50 mM citrate, 75 mM NaCl, pH 5.00, 3% mannitol, 0.02% Tween 80;
Formulation 39: 10 mg/mL samalizumab in 50 mM citrate, 75 mM NaCl, pH 5.50, 1% mannitol, 0.02% Tween 80;
Formulation 42: 10 mg/mL samalizumab in 50 mM citrate, 75 mM NaCl, pH 5.50, 3% mannitol, 0.02% Tween 80;
Formulation 44: 10 mg/mL samalizumab in 50 mM citrate, 75 mM NaCl, pH 5.25, 1% mannitol, 0.02% Tween 80;
Formulation 45: 10 mg/mL samalizumab in 50 mM citrate, 75 mM NaCl, pH 5.25, 3% mannitol, 0.02% Tween 80;
Formulation 47: 10 mg/mL samalizumab in 50 mM citrate, 75 mM NaCl, pH 5.00, 1% mannitol, 0.02% Tween 80; and
Formulation 48: 10 mg/mL samalizumab in 50 mM citrate, 75 mM NaCl, pH 5.00, 3% mannitol, 0.02% Tween 80.

Osmolality Analysis

Osmolality testing was performed at T=0 and 6 months for all forty-eight formulations irrespective of precipitation. At 12 months, osmolality testing was performed on all formulations except for those that showed precipitation. At 24 months, osmolality testing was focused primarily on target formulations 29, 30, 32, 33, 35, and 36, including the higher protein 10 mg/mL counterpart formulations (39, 42, 44, 45, 47, and 48). Overall, osmolality results showed little or no change from T=0 through the 24 month time point for all formulations evaluated. The osmolality results are summarized in Table 3.

TABLE 3

Osmolality Results

| Sample # | NaCl (mM) | Conc. (mg/mL) | pH | Mannitol (%) | T = 0 | T = 6M | T = 12M | T = 24M |
|---|---|---|---|---|---|---|---|---|
| 1 | 150 | 5 | 5.75 | 0 | 446 | 450 | 447 | N/A |
| 2 | 150 | 5 | 5.75 | 1 | 502 | 507 | 506 | N/A |
| 3 | 150 | 5 | 5.75 | 3 | 620 | 622 | 619 | N/A |
| 4 | 150 | 5 | 5.50 | 0 | 455 | 460 | 454 | N/A |
| 5 | 150 | 5 | 5.50 | 1 | 518 | 522 | 515 | N/A |
| 6 | 150 | 5 | 5.50 | 3 | 627 | 635 | 635 | Precip. |
| 7 | 150 | 5 | 5.25 | 0 | 472 | 472 | 471 | Precip. |
| 8 | 150 | 5 | 5.25 | 1 | 531 | 540 | 534 | N/A |
| 9 | 150 | 5 | 5.25 | 3 | 649 | 653 | 662 | N/A |
| 10 | 150 | 5 | 5.00 | 0 | 483 | 491 | 485 | N/A |
| 11 | 150 | 5 | 5.00 | 1 | 562 | 563 | 557 | N/A |
| 12 | 150 | 5 | 5.00 | 3 | 661 | 668 | 663 | N/A |
| 13 | 150 | 10 | 5.75 | 0 | 447 | 454 | Precip. | Precip. |
| 14 | 150 | 10 | 5.75 | 1 | 503 | 515 | Precip. | Precip. |
| 15 | 150 | 10 | 5.75 | 3 | 618 | 626 | 627 | N/A |
| 16 | 150 | 10 | 5.50 | 0 | 463 | 469 | Precip. | Precip. |
| 17 | 150 | 10 | 5.50 | 1 | 517 | 526 | Precip. | Precip. |
| 18 | 150 | 10 | 5.50 | 3 | 635 | 634 | 633 | N/A |
| 19 | 150 | 10 | 5.25 | 0 | 476 | 482 | Precip. | Precip. |
| 20 | 150 | 10 | 5.25 | 1 | 542 | 544 | 536 | N/A |
| 21 | 150 | 10 | 5.25 | 3 | 647 | 662 | 657 | N/A |
| 22 | 150 | 10 | 5.00 | 0 | 494 | 499 | 494 | N/A |
| 23 | 150 | 10 | 5.00 | 1 | 556 | 561 | 565 | N/A |
| 24 | 150 | 10 | 5.00 | 3 | 673 | 670 | 670 | N/A |
| 25 | 75 | 5 | 5.75 | 0 | 328 | 334 | Precip. | Precip. |
| 26 | 75 | 5 | 5.75 | 1 | 380 | 380 | 375 | Precip. |
| 27 | 75 | 5 | 5.75 | 3 | 482 | 490 | 485 | N/A |
| 28 | 75 | 5 | 5.50 | 0 | 351 | 356 | 375 | IS |
| 29 | 75 | 5 | 5.50 | 1 | 383 | 388 | 390 | 411 |
| 30 | 75 | 5 | 5.50 | 3 | 491 | 492 | 491 | N/A |
| 31 | 75 | 5 | 5.25 | 0 | 355 | 356 | 353 | N/A |
| 32 | 75 | 5 | 5.25 | 1 | 400 | 401 | 399 | 401 |
| 33 | 75 | 5 | 5.25 | 3 | 510 | 509 | 511 | 511 |
| 34 | 75 | 5 | 5.00 | 0 | 368 | 369 | 371 | N/A |
| 35 | 75 | 5 | 5.00 | 1 | 416 | 421 | 415 | 426 |
| 36 | 75 | 5 | 5.00 | 3 | 522 | 528 | 524 | 535 |
| 37 | 75 | 10 | 5.75 | 0 | 322 | 326 | Precip. | Precip. |
| 38 | 75 | 10 | 5.75 | 1 | 383 | 379 | Precip. | Precip. |
| 39 | 75 | 10 | 5.75 | 3 | 501 | 504 | 500 | N/A |

TABLE 3-continued

Osmolality Results

| Sample # | NaCl (mM) | Conc. (mg/mL) | pH | Mannitol (%) | T = 0 | T = 6M | T = 12M | T = 24M |
|---|---|---|---|---|---|---|---|---|
| 40 | 75 | 10 | 5.50 | 0 | 337 | 340 | Precip. | Precip. |
| 41 | 75 | 10 | 5.50 | 1 | 395 | 394 | Precip. | Precip. |
| 42 | 75 | 10 | 5.50 | 3 | 512 | 522 | 518 | N/A |
| 43 | 75 | 10 | 5.25 | 0 | 350 | 354 | Precip. | Precip. |
| 44 | 75 | 10 | 5.25 | 1 | 417 | 415 | 413 | 430 |
| 45 | 75 | 10 | 5.25 | 3 | 527 | 531 | 527 | 538 |
| 46 | 75 | 10 | 5.00 | 0 | 371 | 366 | Precip. | Precip. |
| 47 | 75 | 10 | 5.00 | 1 | 431 | 434 | 431 | 442 |
| 48 | 75 | 10 | 5.00 | 3 | 544 | 545 | 542 | 558 |

These results indicate that 5 mg/mL and 10 mg/mL target formulations demonstrate an osmolality greater than 340 mOsm/kg and less than 600 mOsm/kg. In addition, several of the formulations satisfy exemplary clinical expectations of <500 mOsmo/kg. In contrast, the osmolality of the previous samalizumab formulation (i.e., 12.5 mM histidine, 12.5 mM glycine, 150 mM NaCl, 5% mannitol, 0.02% Polysorbate 80, pH 6.0), is >600 mOsm/kg, which has limited the maximum dosing that could be used in clinical settings. Accordingly, the decreased osmolality of these new formulations provide further flexibility for clinical applications and, thus, is an unexpected and significant, clinically relevant improvement over the previous samalizumab formulation.

HPLC Purity Analysis

SEC-HPLC was performed on the sample formulations to determine samalizumab purity by determining the levels of aggregate formation during the 24 month stability. The results are summarized in FIG. 3.

SEC-HPLC testing was performed at 15 months and 18 months only on formulations 29, 30, 32, 33, 35, 36, 44, 45, 47, and 48. The 5 mg/mL formulations maintained a purity level of ≥98.6% throughout the 24 month time point, compared to ~99.0% at T=0. The 10 mg/mL formulations showed a slight increase in aggregate levels throughout the 24M time point with results of ≥97.4%.

Figure 4:
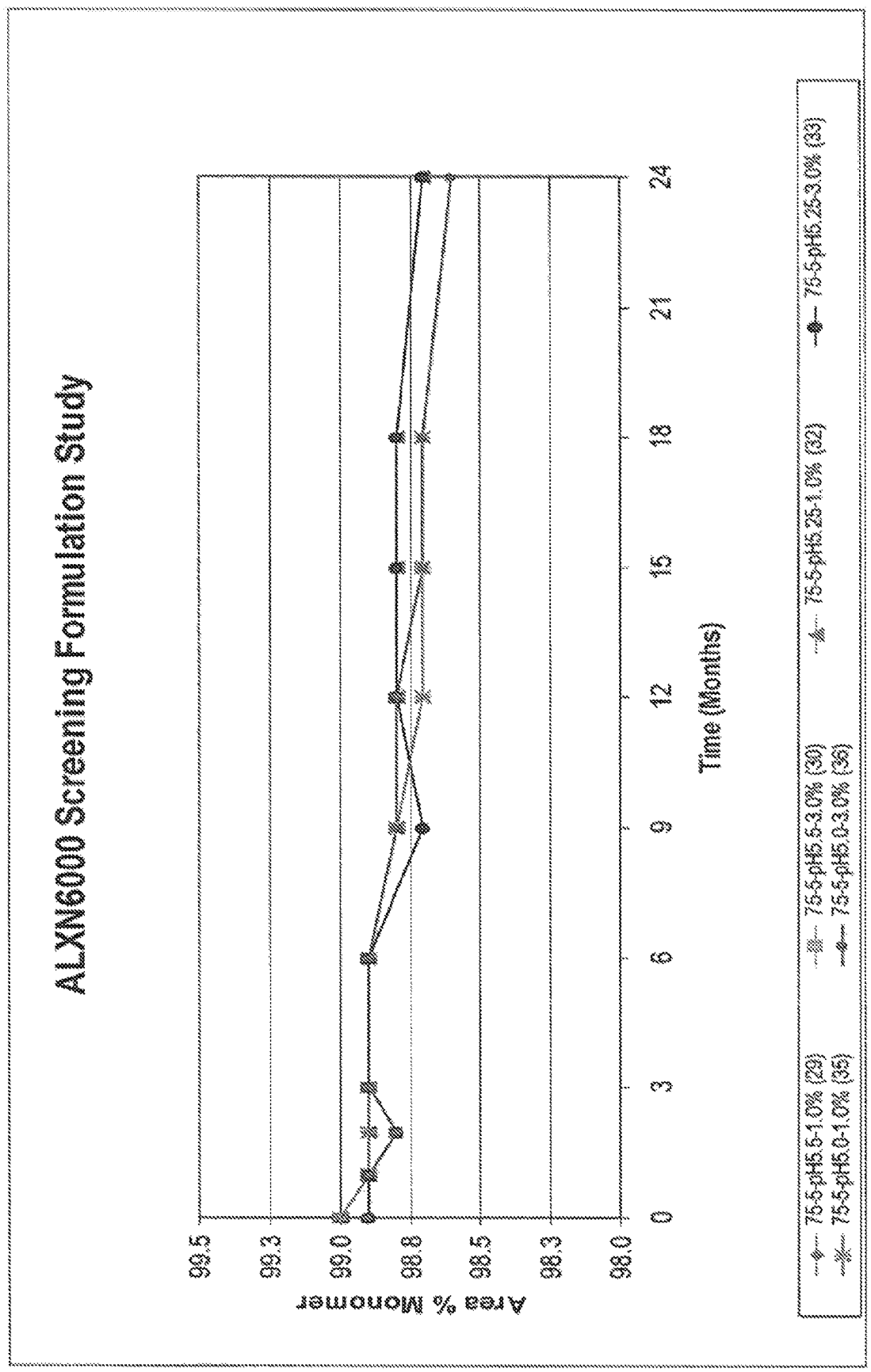
FIG. 4 is a line graph depicting the % monomer of the anti-CD200 antibody in citrate buffered formulations #29, 30, 32, 33, 35, and 36 for a 24-month period as measured by GP-HPLC.

A plot of the % monomer as assessed by GP-HPLC for the target formulations 29, 30, 32, 33, 35, and 36 is presented in FIG. 4, and show that there was no significant increase in aggregation in these formulations throughout the 24 month study, indicating that the citrate buffer maintains samalizumab monomer levels for extended periods of time at 2-8° C. These data demonstrate that all citrate formulations met the GP-HPLC specification of >95% ALXN600 monomer throughout the 24 month study.

SDS-PAGE Analysis of Stability

SDS-PAGE Coomassie testing was performed at T=0 and 6 months (6M) was performed on all 48 formulations. At T=12 months (12M), 18 months (18M) and 24 months (24M), testing was focused on formulations 29, 30, 32, 33, 35, and 36. Results for the 10 mg/mL formulations of 44 and 45 were also included at all time points. Non-reduced SDS-PAGE results were comparable to the reference material for the formulations and time points indicated. No indications of aggregation or degradation were observed. Testing was not performed on all precipitated samples except for formulations 13, 37, 38, and 41 at T=6M. These samples were centrifuged prior to testing to remove precipitation. SDS-PAGE results for the T=0, 6M, 12M, 18 and 24M time-points are summarized in Table 4, and support of the visual appearance and GP-HPLC results where limited aggregation is observed in the target formulations.

TABLE 4

Non-Reduced SDS-PAGE Results

| Sample # | NaCl (mM) | Conc. (mg/mL) | pH | Mannitol (%) | T = 0 | T = 6M | T = 12M | T = 18M | T = 24M |
|---|---|---|---|---|---|---|---|---|---|
| 1 | 150 | 5 | 5.75 | 0 | 89 | 80 | N/A | N/A | N/A |
| 2 | 150 | 5 | 5.75 | 1 | 88 | 81 | N/A | N/A | N/A |
| 3 | 150 | 5 | 5.75 | 3 | 88 | 81 | N/A | N/A | N/A |
| 4 | 150 | 5 | 5.50 | 0 | 88 | 81 | N/A | N/A | N/A |
| 5 | 150 | 5 | 5.50 | 1 | 88 | 80 | N/A | N/A | N/A |
| 6 | 150 | 5 | 5.50 | 3 | 88 | 82 | N/A | N/A Prec. | N/A Prec. |
| 7 | 150 | 5 | 5.25 | 0 | 86 | 82 | N/A | N/A Prec. | N/A Prec. |
| 8 | 150 | 5 | 5.25 | 1 | 86 | 82 | N/A | N/A | N/A |
| 9 | 150 | 5 | 5.25 | 3 | 86 | 81 | N/A | N/A | N/A |
| 10 | 150 | 5 | 5.00 | 0 | 86 | 81 | N/A | N/A | N/A |
| 11 | 150 | 5 | 5.00 | 1 | 86 | 75 | N/A | N/A | N/A |
| 12 | 150 | 5 | 5.00 | 3 | 86 | 77 | N/A | N/A | N/A |
| 13 | 150 | 10 | 5.75 | 0 | 86 | 78* | N/A Prec. | N/A Prec. | N/A Prec. |
| 14 | 150 | 10 | 5.75 | 1 | 87 | 77 | N/A Prec. | N/A Prec. | N/A Prec. |
| 15 | 150 | 10 | 5.75 | 3 | 87 | 77 | N/A | N/A | N/A |
| 16 | 150 | 10 | 5.50 | 0 | 87 | 81 | N/A Prec. | N/A Prec. | N/A Prec. |
| 17 | 150 | 10 | 5.50 | 1 | 87 | 81 | N/A Prec. | N/A Prec. | N/A Prec. |
| 18 | 150 | 10 | 5.50 | 3 | 86 | 81 | N/A | N/A | N/A |
| 19 | 150 | 10 | 5.25 | 0 | 87 | 80 | N/A Prec. | N/A Prec. | N/A Prec. |
| 20 | 150 | 10 | 5.25 | 1 | 87 | 80 | N/A | N/A | N/A |
| 21 | 150 | 10 | 5.25 | 3 | 87 | 79 | N/A | N/A | N/A |
| 22 | 150 | 10 | 5.00 | 0 | 86 | 78 | N/A | N/A | N/A |

TABLE 4-continued

Non-Reduced SDS-PAGE Results

| Sample # | NaCl (mM) | Conc. (mg/mL) | pH | Mannitol (%) | T = 0 | T = 6M | T = 12M | T = 18M | T = 24M |
|---|---|---|---|---|---|---|---|---|---|
| 23 | 150 | 10 | 5.00 | 1 | 87 | 79 | N/A | N/A | N/A |
| 24 | 150 | 10 | 5.00 | 3 | 86 | 79 | N/A | N/A | N/A |
| 25 | 75 | 5 | 5.75 | 0 | 87 | 81 | N/A Prec. | N/A Prec. | N/A Prec. |
| 26 | 75 | 5 | 5.75 | 1 | 87 | 80 | N/A | N/A Prec. | N/A Prec. |
| 27 | 75 | 5 | 5.75 | 3 | 87 | 80 | N/A | N/A | N/A |
| 28 | 75 | 5 | 5.50 | 0 | 87 | 79 | 84 | 82 | 86 |
| 29 | 75 | 5 | 5.50 | 1 | 85 | 79 | 85 | 85 | 88 |
| 30 | 75 | 5 | 5.50 | 3 | 85 | 80 | N/A | N/A | N/A |
| 31 | 75 | 5 | 5.25 | 0 | 86 | 84 | N/A | N/A Prec. | N/A Prec. |
| 32 | 75 | 5 | 5.25 | 1 | 87 | 84 | 84 | 84 | 87 |
| 33 | 75 | 5 | 5.25 | 3 | 86 | 85 | 85 | 85 | 87 |
| 34 | 75 | 5 | 5.00 | 0 | NA | 83 | N/A | N/A | N/A |
| 35 | 75 | 5 | 5.00 | 1 | 87 | 84 | 83 | 82 | 85 |
| 36 | 75 | 5 | 5.00 | 3 | 85 | 83 | 83 | 84 | 87 |
| 37 | 75 | 10 | 5.75 | 0 | 85 | 84 | N/A Prec. | N/A Prec. | N/A Prec. |
| 38 | 75 | 10 | 5.75 | 1 | 86 | 84 | N/A Prec. | N/A Prec. | N/A Prec. |
| 39 | 75 | 10 | 5.75 | 3 | 85 | 84 | N/A | N/A Prec. | N/A Prec. |
| 40 | 75 | 10 | 5.50 | 0 | 86 | 85 | N/A Prec. | N/A Prec. | N/A Prec. |
| 41 | 75 | 10 | 5.50 | 1 | 86 | 84 | N/A Prec. | N/A Prec. | N/A Prec. |
| 42 | 75 | 10 | 5.50 | 3 | 86 | 84 | N/A | N/A Prec. | N/A Prec. |
| 43 | 75 | 10 | 5.25 | 0 | 87 | 83 | N/A Prec. | N/A Prec. | N/A Prec. |
| 44 | 75 | 10 | 5.25 | 1 | 88 | 83 | 82 | 83 | 87 |
| 45 | 75 | 10 | 5.25 | 3 | 89 | 83 | 83 | 82 | 88 |
| 46 | 75 | 10 | 5.00 | 0 | 88 | 84 | N/A Prec. | N/A Prec. | N/A Prec. |
| 47 | 75 | 10 | 5.00 | 1 | 88 | 83 | 82 | 79 | 84 |
| 48 | 75 | 10 | 5.00 | 3 | 88 | 84 | 83 | 80 | 85 |

IEF Analysis of Stability

Isoelectric Focusing (IEF) was performed at T=0 (10 mg/mL formulations only), and 12M, 18M and 24M for the targeted formulations of 29, 30, 32, 33, 35, and 36. The IEF results showed all samples were comparable to the reference material. Differences in IEF banding pattern were not observed for samples tested throughout this study. No indications of oxidation or deamidation were observed. The IEF results for the T=0, 6M, 12M, 18M and 24M time-points are summarized in Table 5.

TABLE 5

Summary of IEF Results

| Sample # | NaCl (mM) | Conc. (mg/mL) | pH | Mannitol (%) | T = 0 | T = 12M | T = 18M | T = 24M |
|---|---|---|---|---|---|---|---|---|
| 1 | 150 | 5 | 5.75 | 0 | N/A | N/A | N/A | N/A |
| 2 | 150 | 5 | 5.75 | 1 | N/A | N/A | N/A | N/A |
| 3 | 150 | 5 | 5.75 | 3 | N/A | N/A | N/A | N/A |
| 4 | 150 | 5 | 5.50 | 0 | N/A | N/A | N/A | N/A |
| 5 | 150 | 5 | 5.50 | 1 | N/A | N/A | N/A | N/A |
| 6 | 150 | 5 | 5.50 | 3 | N/A | N/A | N/A Prec. | N/A Prec. |
| 7 | 150 | 5 | 5.25 | 0 | N/A | N/A | N/A Prec. | N/A Prec. |
| 8 | 150 | 5 | 5.25 | 1 | N/A | N/A | N/A | N/A |
| 9 | 150 | 5 | 5.25 | 3 | N/A | N/A | N/A | N/A |
| 10 | 150 | 5 | 5.00 | 0 | N/A | N/A | N/A | N/A |
| 11 | 150 | 5 | 5.00 | 1 | N/A | N/A | N/A | N/A |
| 12 | 150 | 5 | 5.00 | 3 | N/A | N/A | N/A | N/A |
| 13 | 150 | 10 | 5.75 | 0 | Compares to Ref. | N/A Prec. | N/A Prec. | N/A Prec. |
| 14 | 150 | 10 | 5.75 | 1 | Compares to Ref. | N/A Prec. | N/A Prec. | N/A Prec. |
| 15 | 150 | 10 | 5.75 | 3 | Compares to Ref. | N/A | N/A | N/A |
| 16 | 150 | 10 | 5.50 | 0 | Compares to Ref. | N/A Prec. | N/A Prec. | N/A Prec. |
| 17 | 150 | 10 | 5.50 | 1 | Compares to Ref. | N/A Prec. | N/A Prec. | N/A Prec. |
| 18 | 150 | 10 | 5.50 | 3 | Compares to Ref. | N/A | N/A | N/A |
| 19 | 150 | 10 | 5.25 | 0 | Compares to Ref. | N/A Prec. | N/A Prec. | N/A Prec. |
| 20 | 150 | 10 | 5.25 | 1 | Compares to Ref. | N/A | N/A | N/A |
| 21 | 150 | 10 | 5.25 | 3 | Compares to Ref. | N/A | N/A | N/A |
| 22 | 150 | 10 | 5.00 | 0 | Compares to Ref. | N/A | N/A | N/A |

TABLE 5-continued

Summary of IEF Results

| Sample # | NaCl (mM) | Conc. (mg/mL) | pH | Mannitol (%) | T = 0 | T = 12M | T = 18M | T = 24M |
|---|---|---|---|---|---|---|---|---|
| 23 | 150 | 10 | 5.00 | 1 | Compares to Ref. | N/A | N/A | N/A |
| 24 | 150 | 10 | 5.00 | 3 | Compares to Ref. | N/A | N/A | N/A |
| 25 | 75 | 5 | 5.75 | 0 | N/A | N/A Prec. | N/A Prec. | N/A Prec. |
| 26 | 75 | 5 | 5.75 | 1 | N/A | N/A | N/A Prec. | N/A Prec. |
| 27 | 75 | 5 | 5.75 | 3 | N/A | N/A | N/A | N/A |
| 28 | 75 | 5 | 5.50 | 0 | N/A | Compares to Ref. | Compares to Ref. | Compares to Ref. |
| 29 | 75 | 5 | 5.50 | 1 | N/A | Compares to Ref. | Compares to Ref. | Compares to Ref. |
| 30 | 75 | 5 | 5.50 | 3 | N/A | N/A | N/A | N/A |
| 31 | 75 | 5 | 5.25 | 0 | N/A | N/A | N/A Prec. | N/A Prec. |
| 32 | 75 | 5 | 5.25 | 1 | N/A | Compares to Ref. | Compares to Ref. | Compares to Ref. |
| 33 | 75 | 5 | 5.25 | 3 | N/A | Compares to Ref. | Compares to Ref. | Compares to Ref. |
| 34 | 75 | 5 | 5.00 | 0 | N/A | N/A | N/A | N/A |
| 35 | 75 | 5 | 5.00 | 1 | N/A | Compares to Ref. | Compares to Ref. | Compares to Ref. |
| 36 | 75 | 5 | 5.00 | 3 | N/A | Compares to Ref. | Compares to Ref. | Compares to Ref. |
| 37 | 75 | 10 | 5.75 | 0 | Compares to Ref. | N/A Prec. | N/A Prec. | N/A Prec. |
| 38 | 75 | 10 | 5.75 | 1 | Compares to Ref. | N/A Prec. | N/A Prec. | N/A Prec. |
| 39 | 75 | 10 | 5.75 | 3 | Compares to Ref. | N/A | N/A Prec. | N/A Prec. |
| 40 | 75 | 10 | 5.50 | 0 | Compares to Ref. | N/A Prec. | N/A Prec. | N/A Prec. |
| 41 | 75 | 10 | 5.50 | 1 | Compares to Ref. | N/A Prec. | N/A Prec. | N/A Prec. |
| 42 | 75 | 10 | 5.50 | 3 | Compares to Ref. | N/A | N/A Prec. | N/A Prec. |
| 43 | 75 | 10 | 5.25 | 0 | Compares to Ref. | N/A Prec. | N/A Prec. | N/A Prec. |
| 44 | 75 | 10 | 5.25 | 1 | Compares to Ref. | Compares to Ref. | Compares to Ref. | Compares to Ref. |
| 45 | 75 | 10 | 5.25 | 3 | Compares to Ref. | Compares to Ref. | Compares to Ref. | Compares to Ref. |
| 46 | 75 | 10 | 5.00 | 0 | Compares to Ref. | N/A Prec. | N/A Prec. | N/A Prec. |
| 47 | 75 | 10 | 5.00 | 1 | Compares to Ref. | Compares to Ref. | Compares to Ref. | Compares to Ref. |
| 48 | 75 | 10 | 5.00 | 3 | Compares to Ref. | Compares to Ref. | Compares to Ref. | Compares to Ref. |

Discussion

The results of this study indicate that samalizumab formulated at a concentration of 5-10 mg/mL in citrate buffer (pH ranges of 5.0 to 6.0), 75-150 mM NaCl, 1% to 3% mannitol and 0.02% Polysorbate 80, maintains solubility for 24 months at 2-8° C. For example, formulations 29, 30, 32, 33, 35 and 36 demonstrated excellent stability by visual appearance and in the GP-HPLC, SDS-PAGE and IEF assays. In addition, the osmolality of these formulations ranged from 350 to 525 mOSm/kg, which is a significant improvement over the previous histidine buffered formulation.

These data indicate that, surprisingly, citrate buffer and polyol concentrations (e.g., mannitol) were formulation parameters for maintaining the solubility and stability of samalizumab at 2-8° C. Many of the formulations identified in this study satisfy all clinical expectations for samalizumab, including pH>5.0, Osmolality≤500 mOsmo/kg, and samalizumab concentrations of greater than 5.0 mg/mL.

Example 2

The compatibility of 5 mg/mL samalizumab in a formulation consisting of 50 mM sodium citrate, 75 mM sodium chloride, 2% (w/v) mannitol, 0.02% (w/v) Polysorbate-80, pH 5.2 with typically used materials for clinical IV administration was assessed. Additionally, the stability of this formulation diluted with 0.9% (w/v) saline over the planned duration of administration by intravenous (IV) infusion was evaluated. To provide support for the largest variety of infusion containers and administration sets likely to be encountered during clinical usage, several representative infusion containers and tubing sets constructed from commonly used materials were studied. The need for in-line filtration of this samalizumab formulation admixture prior to patient administration was determined through use of infusion sets supplied with an in-line 0.22 μm filter. This study was not intended to restrict the use of IV delivery systems to those vendor products utilized in the course of this study, but to demonstrate compatibility with containers and tubing sets of various materials of construction.

Materials and Methods

A total of four IV component systems were examined, which used 250 mL IV bags with a fill volume of 125 mL. System 1 consisted of a Baxter Continu-Flo solution set attached to a Baxter Viaflex bag. Both the solution set and the IV bag contained PVC with DEHP (diethylhexyl phthalate or Bis(2-ethylhexyl) phthalate, IUPAC name). System 2 consisted of a Baxter solution set attached to a Baxter Viaflo bag. The Viaflo bag contained polyolefin without DEHP. Likewise, the solution set did not contain DEHP. System 3 consisted of a B Braun solution set attached to a Baxter Intravia bag which was purchased empty. The Intravia bag contained polyolefin with PVC ports without DEHP. The B Braun IV solution set did not contain PVC or DEHP. System 4 consisted of only a 250 mL Baxter Exactamix which was purchased empty. The Exactamix bag contained ethylene vinyl acetate (EVA).

To evaluate the stability of the samalizumab formulation with representative IV bag materials in the absence of saline diluent in order to provide an upper limit for neat administration, System 1 and System 2 containers containing saline were emptied. System 3 and System 4 were purchased empty. To each bag, 125 mL of the 5 mg/mL samalizumab formulation was added. Each of the systems were also examined using 125 mL of formulation buffer in the absence of samalizumab.

A one-to-one dilution of the samalizumab formulation to saline diluent was also studied in the four systems. For those bags already containing saline diluent, 187.5 mL of saline was removed from each bag and 62.5 mL of the samalizumab formulation was added back into the bag to yield a total volume of 125 mL of a one-to-one dilution of the samalizumab formulation to saline. A control of formulation buffer without samalizumab was also examined using the same approach. For System 3 and System 4, a 0.9% (w/v) saline solution in water was prepared to allow for a one-to-one dilution of the samalizumab formulation to saline having a final volume of 125 mL and subsequently added to each bag. Formulation buffer was treated in a similar manner and added to empty bags as a control.

One set of samples was stored at 2-8° C. and another set was stored at ambient temperature for up to 24 hours. At T=0, 2, 4, 6, and 24 hours, 10 mL aliquots were sampled through the attached IV set for Systems 1 to 3. System 4 was sampled through the injection port using a 10 mL disposable syringe fitted with a 27 gauge needle. Sampling was carried out according to Table 6.

TABLE 6

| Time points and pull volumes | | | | | |
|---|---|---|---|---|---|
| Temperature | T = 0 | T = 2 hrs | T = 4 hrs | T = 6 hrs | T = 24 hrs |
| 2-8° C. | 10 mL | 10 mL | 10 mL | 10 mL | 85 mL |
| Ambient temperature | 10 mL | 10 mL | 10 mL | 10 mL | 85 mL |

Samples were kept at 2-8° C. until analyzed according to the analytical methods listed in Table 7.

TABLE 7

| Analytical methods | | |
|---|---|---|
| Test | Assay Type | Objective and Rationale |
| Appearance | General Characteristic | A change in appearance may indicate product degradation. |
| pH | General Characteristic | A failure in pH results could indicate a change in buffer capacity of the solution. |
| Protein Concentration (UV per SoloVPE) | Protein Concentration | Altered protein concentration results could indicate changes in product solubility or stability. |
| Turbidity (UV-vis) | General Characteristic | Increases in turbidity could indicate changes in product solubility or stability. |
| SE HPLC | Purity | To ensure that the sample remains intact, and meets the purity requirements. |
| Small volume HIAC | General Characteristic | To quantify changes in the number of subvisible particles in solution. An increase in subvisible particles may indicate physical changes in the profile of the product which may impact safety. |
| MFI | General Characteristic | To quantify changes in the number of subvisible particles in solution. An increase in subvisible particles may indicate physical changes in the profile of the product which may impact safety. |
| Dynamic Light Scattering (DLS) | Stability | To estimate the extent of aggregation/degradation. |
| CE-SDS | Purity | An alteration in the CE-SDS pattern may indicate product degradation, such as cleavage of the polypeptide chain(s) or aggregation of the product. |
| Imagining Capillary Electrophoresis (iCE) | Identity | A failing result may indicate protein degradation with the formation of uncharacteristic isoforms. |

Results

All samples were found to be clear, colorless and practically free from particles. All samples were between pH 5.3 and pH 5.5 with no obvious trend in pH observed. Protein concentration did not change upon sample storage as observed for all samples. The turbidity of the samples was measured using a 96 well plate and a UV-vis plate reader monitoring the absorbance at 650 nm, and no significant trends were observed. The percent main peak area of the samples determined using size exclusion UPLC were >99.0% with no trends observed.

All samples were analyzed by small volume high accuracy (HIAC) particle counting system, including formulation blanks which were prepared using formulation buffer and mixed in the same manner as the drug product. The formulation blanks contained≤25 cumulative counts per mL at ≥10 µm and ≤5 cumulative counts per mL at ≥25 µm. Once analyzed, the values for the corresponding formulation blank were subtracted from the values obtained for the sample containing samalizumab. All samples passed USP guideline criteria for particle counts at ≥10 µm with the exception of System 2 diluted 1 to 1 with saline after 24 hours at 2-8° C. This sample contained 30 cumulative counts per mL. The container volume of 250 mL results in a total dose of particles of 7500 for this condition. All samples contained≤5 cumulative counts per mL at ≥25 µm. While this value is relatively low, any sample containing 3 or more particles would not meet the USP guideline criteria for particle counts at ≥25 µm. It is recommended here to include an inline 0.2 µm filter during the administration of this samalizumab formulation.

All samples were analyzed by Mean Fluorescence Intensity (MFI), including formulation blanks. The cumulative counts per mL at ≥10 µm for each of the systems evaluated. System 2 showed a dramatic increase in particle counts after storage at 2-8° C. for 24 hours. This was observed for both the diluted sample and the neat samples. System 4 diluted samples stored at 2-8° C. showed a small gradual increase. Evaluation of the cumulative counts per mL at ≥25 µm for each of the systems indicated that System 2 containing neat samalizumab and stored at 2-8° C. showed a significant increase in cumulative counts after 6 hours. System 2 containing diluted samalizumab and stored at 2-8° C. showed an increase in cumulative counts at the 24 hour time point. System 3 containing diluted samalizumab stored at 2-8° C. also showed a large number of particles at the 6 hour time point but failed to show the same level of particle formation at the 24 hour time point. This observation was repeated for system 3 stored at 23-27° C. for 6 hours, but not seen at the 24 hour time point.

Dynamic light scattering analysis of the neat and diluted samalizumab samples showed that the mean percent polydispersity for all samples was <20% with the majority of samples having a percent polydispersity of <10%. All samples evaluated predominantly showed a peak that is consistent with the anticipated size of a monomer.

The percent heavy chain plus the percent light chain for both the 2-8° C. and the 23-27° C. samples had values above 95 percent as analyzed by CE-SDS reduced LOC. The percent main peak for both the 2-8° C. and the 23-27° C. samples had values above 98 percent as analyzed by non-reduced CE-SDS LOC.

The percent main peak by imaging capillary electrophoresis (iCE) for all samples showed no obvious trends.

Conclusion

Analytical testing of the 5 mg/mL citrate buffered samalizumab formulation, including particle analysis, showed only minor changes up to 24 hours of storage at 2-8° C. as well as storage at 23-27° C. for up to 24 hours. MFI showed changes at 2-8° C. for System 2 containing neat samalizumab after 6 hours of storage, but this increase was not observed using the small volume HIAC. Accordingly, based on the overall results, no restrictions are placed on the IV administration of neat or saline diluted 5 mg/mL samalizumab for up to 24 hours of storage at 2-8° C. or 23-27° C.

Example 3

Additional studies to identify stable anti-CD200 antibody formulations containing high antibody concentrations were conducted.

A nine (9) month formulation stability study was conducted to identify improved, high concentration anti-CD200 antibody formulations containing samalizumab. Initial preformulation experiments screened pH ranges from 4.0 to 6.0 in sorbitol and NaCl to determine thermal and chemical stability of the proposed initial formulations. Differential Scanning calorimetry (DSC) and Differential Scanning Fluorimetry (DSF) testing as a function of temperature showed the optimal pH range to be within pH 5-6, and acetate buffer was selected for this range. Additionally, sodium phosphate buffers were rejected for challenges with freeze/thaw cycling. Isothermal chemical denaturation studies (via guanidine HCl addition according to standard techniques) were also used, and confirmed the selection of acetate, because phosphate showed lower $\Delta G1$.

Formulation of samples containing sodium acetate buffer, a stabilizer/tonicifier (i.e., a neutral amino acid with a non charged side chain such as L-glycine), and a surfactant (i.e., polysorbate 80), at a pH of about 5.5 was performed according to standard techniques. For example, prior to initial concentration via tangential flow filtration (TFF), the anti-CD200 antibody samples were spiked with stock amino acid solution (e.g., glycine solution (1M in sterile water) to provide the desired concentration of amino acid. The solution was then concentrated to 30 g/L using TFF. The buffer was then exchanged for 10 mM Na acetate and 290 mM glycine at pH 5.5, concentrated to approximately 65 g/L, and then 10% polysorbate 80 (w/v) aqueous solution was added to provide the desired concentration. The pH was tested to verify pH prior to dilution. Samples were diluted to approximately 50 mg/ml, sterile filtered, and stored in polystyrene bottles and/or process bags at 2-8° C.

Liquid formulations for subcutaneous administration with 50 mM anti-CD200 antibody (samalizumab), 10 mM Na acetate, 290 mM L-glycine, and 0.05% (w/v) polysorbate 80 at pH 5.5 were found to be stable (clear and colorless) at 2-8° C. for at least 6 months. Additional testing will show that the stability at 2-8° C. was maintained for at least 9 months, at least 12 months, and at least 24 months.

Tests for appearance, pH, osmolality, protein concentration, SE UPLC, CD-SDS or LoC, iCE, peptide mapping, particulates by MFI HIAC and SV HIAC, Dynamic Light Scattering, and anti-CD200 concentration, will be performed at −80° C., −20° C., 2-8° C. and 23-27° C. The study will continue through the 24 month time point for −80° C., −20° C., and 2-8° C., and will continue through the 12 month time point at 23-27° C.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

SEQUENCE LISTING SUMMARY

| DESIGNATION | SEQUENCE | |
|---|---|---|
| Precursor human CD200 isoform A | MERLVIRMPFSHLSTYSLVWVMAAVVLCTAQVQVTQDERE QLYTPASLKCSLQNAQEALIVTWQKKKAVSPENMVTFSENH GVVIQPAYKDKINITQLGLQNSTITFWNITLEDEGCYMCLF NTFGFGKISGTACLTVYVQPIVSLHYKFSEDHLNITCSATA RPAPMVFWKVPRSGIENSTVTLSHPNGTTSVTSILHIKDPK NQVGKEVICQVLHLGTVTDFKQTVNKGYWFSVPLLLSIVSL VILLVLISILLYWKRHRNQDREP | SEQ ID NO: 1 |
| Human CD200 isoform B | MERLTLTRTIGGPLLTATLLGKTTINDYQVIRMPFSHLSTY SLVWVMAAVVLCTAQVQVTQDEREQLYTPASLKCSLQNAQ EALIVTWQKKKAVSPENMVTFSENHGVVIQPAYKDKINITQ LGLQNSTITFWNITLEDEGCYMCLFNTFGFGKISGTACLTV YVQPIVSLHYKFSEDHLNITCSATARPAPMVFWKVPRSGIE NSTVTLSHPNGTTSVTSILHIKDPKNQVGKEVICQVLHLGT VTDFKQTVNKGYWFSVPLLLSIVSLVILLVLISILLYWKRH RNQDREP | SEQ ID NO: 2 |
| Full-length, mature human CD200 | VIRMPFSHLSTYSLVWVMAAVVLCTAQVQVTQDEREQLYT TASLKCSLQNAQEALIVTWQKKKAVSPENMVTFSENHGVVI QPAYKDKINITQLGLQNSTITFWNITLEDEGCYMCLFNTFG FGKISGTACLTVYVQPIVSLHYKFSEDHLNITCSATARPAP MVFWKVPRSGIENSTVTLSHPNGTTSVTSILHIKDPKNQVG KEVICQVLHLGTVTDFKQTVNKGYWFSVPLLLSIVSLVILL VLISILLYWKRHRNQDRGELSQGVQKMT | SEQ ID NO: 3 |
| Samalizumab Light Chain CDR1 | KASQDINSYLS | SEQ ID NO: 4 |
| Samalizumab Light Chain CDR2 | RANRLVD | SEQ ID NO: 5 |
| Samalizumab Light Chain CDR3 | LQYDEFPYT | SEQ ID NO: 6 |
| Samalizumab Heavy Chain CDR1 | CYSFTDYIIL | SEQ ID NO: 7 |
| Samalizumab Heavy Chain CDR2 | HIDPYYCSSNYNLKFKC | SEQ ID NO: 8 |
| Samalizumab Heavy Chain CDR3 | SKRDYFDY | SEQ ID NO: 9 |
| Samalizumab Variable Heavy Chain | QVQLQQSCSELKKPCASVKISCKASCYSFTDYIILWVRQNPGKG LEWIGHIDPYYCSSNYNLKFKGRVTITADQSTTTAYMELSSLRS EDTAVYYCGRSKRDYFDYWGQGTTLTVSS | SEQ ID NO: 10 |
| Samalizumab Variable Light Chain | DIQMTQSPSSLSASICDRVTITCKASQDINSYLSWFQQKPGKA PKLLIYRANRLVDGVPSRFSGSGSGTDYTLTISSLQPEDFAVY YCLQYDEFPYTFGGGTKLEIKR | SEQ ID NO: 11 |
| TPP-119 Variable Heavy Chain | QVQLVQSGAEVKKPCASVKVSCKASGYSFTDYIILWVRQAPGQR LEWMCHIDPYYGSSNYNLKFKCRVTITRDTSASTAYMELSSLRS EDTAVYYCARSKRDYFDYWGQGTLVTVSS | SEQ ID NO: 12 |
| TPP-119 Variable Light Chain | QMTQSPSSLSASVGDRVTITCKASQDINSYLSWFQQKPGKAPKS LIYRANRLVDGVPSRFSGSGSGTDFTLTISSLQPEDFATYYCLQ YDEFPYTFGQGTKLEIK | SEQ ID NO: 13 |
| TPP-1141 Variable Heavy Chain | QVQLVQSGAEVKKPGASVKVSCKASGYSFTDYIILWVRQAPGQR LEWICHIDPYYCSSNYNLKFKGRVTITRDTSASTAYMELSSLRS EDTAVYYCARSKRDYFDYWGQGTLVTVSSASTKGPSVFPLAPCS RSTSESTAALGCLVKDYFPEPVTVS | SEQ ID NO: 14 |
| TPP-1141 Variable Light Chain | DIQMTQSPSSLSASVGDRVTITCKASQDINSYLSWFQQKPGKAP KSLIYRANRLVDGVPSRFSGSGSGTDFTLTISSLQPEDFATYYC LQYDEFPYTFGQGTKLEIK | SEQ ID NO: 15 |
| TPP-1142 Variable Heavy Chain | QVQLVQSGAEVKKPGASVKVSCKASGYSFTDYIILWVRQAPGQR LEWMGHIDPYYCSSNYNLKFKGRVTITRDTSASTAYMELSSLRS EDTAVYYCGRSKRDYFDYWGQGTLVTVSSASTKGPSVFPLAPCS RSTSESTAALGCLVKDYFPEPVTVS | SEQ ID NO: 16 |

SEQUENCE LISTING SUMMARY

| DESIGNATION | SEQUENCE | |
|---|---|---|
| TPP-1142 Variable Light Chain | DIQMTQSPSSLSASVGDRVTITCKASQDINSYLSWFQQKPGKAP KSLIYRANRLVDGVPSRFSGSGSGTDFTLTISSLQPEDFATYYC LQYDEFPYTFGQGTKLEIK | SEQ ID NO: 17 |
| TPP-1143 Variable Heavy Chain | QVQLVQSGAEVKKPGASVKVSCKASGYSFTDYIILWVRQAPGQR LEWMGHIDPYYGSSNYNLKFKGRVTITRDTSASTAYMELSSLRS EDTAVYYCGRSKRDYFDYWGQGTLVTVSSASTKGPSVFPLAPCS RSTSESTAALGCLVKDYFPEPVTVS | SEQ ID NO: 18 |
| TPP-1143 Variable Light Chain | DIQMTQSPSSLSASVGDRVTITCKASQDINSYLSWFQQKPGKAP KSLIYRANRLVDGVPSRFSGSGSGTDFTLTISSLQPEDFGTYYC LQYDEFPYTFGQGTKLEIK | SEQ ID NO: 19 |
| Samalizumab Heavy Chain | QVQLQQSGSELKKPGASVKISCKASGYSFTDYIILWVRQNPGKG LEWIGHIDPYYGSSNYNLKFKGRVTITADQSTTTAYMELSSLRS EDTAVYYCGRSKRDYFDYWGQGTTLTVSSASTKGPSVFPLAPCS RSTSESTAALGCLVKDYFPEPVTVSWNSGALTSGVHTFPAVLQS SGLYSLSSVVTVPSSNFGTQTYTCNVDHKPSNTKVDKTVERKCC VECPPCPAPPVAGPSVFLFPPKPKDTLMISRTPEVTCVVVDVSQ EDPEVQFNWYVDGVEVHNAKTKPREEQFNSTYRVVSVLTVLHQD WLNGKEYKCKVSNKGLPSSIEKTISKAKCQPREPQVYTLPPSQE EMTKNQVSLTCLVKGFYPSDIAVEWESNGQPENNYKTTPPVLDS DGSFFLYSRLTVDKSRWQEGNVFSCSVMHEALHNHYTQKSLS LSLGK | SEQ ID NO: 20 |
| Samalizumab Light Chain | DIQMTQSPSSLSASIGDRVTITCKASQDINSYLSWFQQKPGKA PKLLIYRANRLVDGVPSRFSGSGSGTDYTLTISSLQPEDFAVY YCLQYDEFPYTFGGGTKLEIKRTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSF NRGEC | SEQ ID NO: 21 |
| TPP-1141 Heavy Chain | QVQLVQSGAEVKKPGASVKVSCKASGYSFTDYIILWVRQAPGQR LEWIGHIDPYYGSSNYNLKFKGRVTITRDTSASTAYMELSSLRS EDTAVYYCARSKRDYFDYWGQGTLVTVSSASTKGPSVFPLAPCS RSTSESTAALGCLVKDYFPEPVTVSWNSGALTSGVHTFPAVLQS SGLYSLSSVVTVPSSNFGTQTYTCNVDHKPSNTKVDKTVERKCC VECPPCPAPPVAGPSVFLFPPKPKDTLMISRTPEVTCVVVDVSQ EDPEVQFNWYVDGVEVHNAKTKPREEQFNSTYRVVSVLTVLHQD WLNGKEYKCKVSNKGLPSSIEKTISKAKGQPREPQVYTLPPSQE EMTKNQVSLTCLVKCFYPSDIAVEWESNGQPENNYKTTPPVLDS DGSFFLYSRLTVDKSRWQEGNVFSCSVMHEALHNHYTQKSLSLS LGK | SEQ ID NO: 22 |
| TPP-1141 Light Chain | DIQMTQSPSSLSASVGDRVTITCKASQDINSYLSWFQQKPGKAP KSLIYRANRLVDGVPSRFSGSGSGTDFTLTISSLQPEDFATYYC LQYDEFPYTFGQGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQCLSSPVTKSFNRGEC | SEQ ID NO: 23 |
| TPP-1142 Heavy Chain | QVQLVQSCAEVKKPGASVKVSCKASGYSFTDYIILWVRQAPGQR LEWMGHIDPYYCSSNYNLKFKGRVTITRDTSASTAYMELSSLRS EDTAVYYCGRSKRDYFDYWGQGTLVTVSSASTKGPSVFPLAPCS RSTSESTAALGCLVKDYFPEPVTVSWNSGALTSCVHTFPAVLQS SGLYSLSSVVTVPSSNFGTQTYTCNVDHKPSNTKVDKTVERKCC VECPPCPAPPVAGPSVFLFPPKPKDTLMISRTPEVTCVVVDVSQ EDPEVQFNWYVDGVEVHNAKTKPREEQFNSTYRVVSVLTVLHQD WLNGKEYKCKVSNKGLPSSIEKTISKAKGQPREPQVYTLPPSQE EMTKNQVSLTCLVKGFYPSDIAVEWESNGQPENNYKTTPPVLDS DGSFFLYSRLTVDKSRWQEGNVFSCSVMHEALHNHYTQKSLSLS LGK | SEQ ID NO: 24 |
| TPP-1142 Light Chain | DIQMTQSPSSLSASVGDRVTITCKASQDINSYLSWFQQKPGKAP KSLIYRANRLVDGVPSRFSGSGSGTDFTLTISSLQPEDFATYYC LQYDEFPYTFGQCTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC | SEQ ID NO: 25 |
| TPP-1143 Heavy Chain | QVQLVQSGAEVKKPGASVKVSCKASGYSFTDYIILWVRQAPGQR LEWMGHIDPYYCSSNYNLKFKGRVTITRDTSASTAYMELSSLRS EDTAVYYCGRSKRDYFDYWGQGTLVTVSSASTKGPSVFPLAPCS RSTSESTAALGCLVKDYFPEPVTVSWNSGALTSCVHTFPAVLQS SCLYSLSSVVTVPSSNFGTQTYTCNVDHKPSNTKVDKTVERKCC VECPPCPAPPVAGPSVFLFPPKPKDTLMISRTPEVTCVVVDVSQ | SEQ ID NO: 26 |

SEQUENCE LISTING SUMMARY

| DESIGNATION | SEQUENCE | |
|---|---|---|
| | EDPEVQFNWYVDGVEVHNAKTKPREEQFNSTYRVVSVLTVLHQD WLNGKEYKCKVSNKGLPSSIEKTISKAKGQPREPQVYTLPPSQE EMTKNQVSLTCLVKGFYPSDIAVEWESNGQPENNYKTTPPVLDS DGSFFLYSRLTVDKSRWQEGNVFSCSVMHEALHNHYTQKSLSLS LGK | |
| TPP-1143 Light Chain | DIQMTQSPSSLSASVGDRVTITCKASQDINSYLSWFQQKPGKAP KSLIYRANRLVDGVPSRFSGSGSGTDFTLTISSLQPEDFGTYYC LQYDEFPYTFGQGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQCLSSPVTKSFNRGEC | SEQ ID NO: 27 |
| IgG2/G4 hybrid constant region | ASTKGPSVFPLAPCSRSTSESTAALGCLVKDYFPEPVTVSW NSGALTSGVHTFPAVLQSSGLYSLSSVVTVPSSNFGTQTYT CNVDHKPSNTKVDKTVERKCCVECPPCPAPPVAGPSVFLFP PKPKDTLMISRTPEVTCVVVDVSQEDPEVQFNWYVDGVEVH NAKTKPREEQFNSTYRVVSVLTVLHQDWLNGKEYKCKVSNK GLPSSIEKTISKAKGQPREPQVYTLPPSQEEMTKNQVSLTC LVKGFYPSDIAVEWESNGQPENNYKTTPPVLDSDGSFFLYS RLTVDKSRWQEGNVFSCSVMHEALHNHYTQKSLSLSLGK | SEQ ID NO: 28 |

What is claimed is:

1. A liquid pharmaceutical formulation comprising:
   (a) an anti-CD200 antibody or antigen binding fragment thereof at a concentration of between about 5 to 10 mg/mL, wherein the anti-CD200 antibody or antigen binding fragment comprises a light chain variable region comprising the sequence set forth in SEQ ID NO:11 and a heavy chain variable region comprising the sequence set forth in SEQ ID NO:10;
   (b) about 1 to 3% mannitol;
   (c) about 0.02% polysorbate
   (d) about 50 mM citrate buffer at a pH of about 5.0 to about 6, and
   (e) about 75 to 150 mM NaCl;
   wherein the formulation has an osmolality of less than 525 mOsm/kg and is stable at 2-8° C. for a period of at least 9 months.

2. An article of manufacture comprising the liquid pharmaceutical formulation of claim 1 in a container.

3. A kit comprising the liquid pharmaceutical formulation of claim 1, and instructions for therapeutic use.

4. The liquid pharmaceutical formulation of claim 1, wherein the pH is about 5.0 to about 5.5.

5. The liquid pharmaceutical formulation of claim 1, wherein the anti-CD200 antibody is samalizumab.

6. The liquid pharmaceutical formulation of claim 1, wherein the formulation is suitable for intravenous administration.

7. The liquid pharmaceutical formulation of claim 1, wherein the formulation is suitable for subcutaneous administration.

8. The liquid pharmaceutical formulation of claim 1, wherein the formulation is sterile.

9. The liquid pharmaceutical formulation of claim 1, wherein at least 95% of the anti-CD200 antibody molecules are monomers after storage at 2-8° C. for 9 months.

10. The liquid pharmaceutical formulation of claim 1, comprising one or more preservatives.

11. The liquid pharmaceutical formulation of claim 1, wherein the formulation is substantially pyrogen-free.

12. The liquid pharmaceutical formulation of claim 1, wherein the formulation is provided in unit dosage form.

13. The liquid formulation of claim 1, wherein the formulation comprises:
   a. about 5 mg/ml samalizumab;
   b. about 1% mannitol;
   c. about 0.02% polysorbate;
   d. about 50 mM citrate buffer at a pH of about 5.5; and
   e. about 75 mM NaCl.

14. The liquid formulation of claim 1, wherein the formulation comprises:
   a. about 5 mg/ml samalizumab;
   b. about 3% mannitol;
   c. about 0.02% polysorbate;
   d. about 50 mM citrate buffer at a pH of about 5.5; and
   e. about 75 mM NaCl.

15. The liquid formulation of claim 1, wherein the formulation comprises:
   a. about 5 mg/ml samalizumab;
   b. about 1% mannitol;
   c. about 0.02% polysorbate;
   d. about 50 mM citrate buffer at a pH of about 5.25; and
   e. about 75 mM NaCl.

16. The liquid formulation of claim 1, wherein the formulation comprises:
   a. about 5 mg/ml samalizumab;
   b. about 3% mannitol;
   c. about 0.02% polysorbate;
   d. about 50 mM citrate buffer at a pH of about 5.25; and
   e. about 75 mM NaCl.

17. The liquid formulation of claim 1, wherein the formulation comprises:
   a. about 5 mg/ml samalizumab;
   b. about 1% mannitol;
   c. about 0.02% polysorbate;
   d. about 50 mM citrate buffer at a pH of about 5.0; and
   e. about 75 mM NaCl.

18. The liquid formulation of claim 1, wherein the formulation comprises:
   a. about 5 mg/ml samalizumab;
   b. about 3% mannitol;
   c. about 0.02% polysorbate;
   d. about 50 mM citrate buffer at a pH of about 5.0; and
   e. about 75 mM NaCl.

19. The liquid formulation of claim 1, wherein the formulation comprises:
   a. about 10 mg/ml samalizumab;
   b. about 1% mannitol;
   c. about 0.02% polysorbate;
   d. about 50 mM citrate buffer at a pH of about 5.5; and
   e. about 75 mM NaCl.

20. The liquid formulation of claim 1, wherein the formulation comprises:
   a. about 10 mg/ml samalizumab;
   b. about 3% mannitol;
   c. about 0.02% polysorbate;
   d. about 50 mM citrate buffer at a pH of about 5.5; and
   e. about 75 mM NaCl.

21. The liquid formulation of claim 1, wherein the formulation comprises:
   a. about 10 mg/ml samalizumab;
   b. about 1% mannitol;
   c. about 0.02% polysorbate;
   d. about 50 mM citrate buffer at a pH of about 5.25; and
   e. about 75 mM NaCl.

22. The liquid formulation of claim 1, wherein the formulation comprises:
   a. about 10 mg/ml samalizumab;
   b. about 3% mannitol;
   c. about 0.02% polysorbate;
   d. about 50 mM citrate buffer at a pH of about 5.25; and
   e. about 75 mM NaCl.

23. The liquid formulation of claim 1, wherein the formulation comprises:
  a. about 10 mg/ml samalizumab;
  b. about 1% mannitol;
  c. about 0.02% polysorbate;
  d. about 50 mM citrate buffer at a pH of about 5.0; and
  e. about 75 mM NaCl.

24. The liquid formulation of claim 1, wherein the formulation comprises:
  a. about 10 mg/ml samalizumab;
  b. about 3% mannitol;
  c. about 0.02% polysorbate;
  d. about 50 mM citrate buffer at a pH of about 5.0; and
  e. about 75 mM NaCl.

* * * * *

SEQUENCE LISTING

<160> NUMBER OF SEQ ID NOS: 28

<210> SEQ ID NO 1
<211> LENGTH: 269
<212> TYPE: PRT
<213> ORGANISM: Homo sapiens

<400> SEQUENCE: 1

```
Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
        115                 120                 125

Gly Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205
```

```
Gly Lys Glu Val Ile Cys Gln Val Leu His Leu Gly Thr Val Thr Asp
    210             215                 220
Phe Lys Gln Thr Val Asn Lys Gly Tyr Trp Phe Ser Val Pro Leu Leu
225             230                 235                 240
Leu Ser Ile Val Ser Leu Val Ile Leu Val Leu Ile Ser Ile Leu
            245                 250                 255
Leu Tyr Trp Lys Arg His Arg Asn Gln Asp Arg Glu Pro
            260                 265

<210> SEQ ID NO 2
<211> LENGTH: 294
<212> TYPE: PRT
<213> ORGANISM: Homo sapiens

<400> SEQUENCE: 2

Met Glu Arg Leu Thr Leu Thr Arg Thr Ile Gly Gly Pro Leu Leu Thr
1               5                   10                  15
Ala Thr Leu Leu Gly Lys Thr Thr Ile Asn Asp Tyr Gln Val Ile Arg
            20                  25                  30
Met Pro Phe Ser His Leu Ser Thr Tyr Ser Leu Val Trp Val Met Ala
        35                  40                  45
Ala Val Val Leu Cys Thr Ala Gln Val Gln Val Val Thr Gln Asp Glu
    50                  55                  60
Arg Glu Gln Leu Tyr Thr Pro Ala Ser Leu Lys Cys Ser Leu Gln Asn
65                  70                  75                  80
Ala Gln Glu Ala Leu Ile Val Thr Trp Gln Lys Lys Lys Ala Val Ser
                85                  90                  95
Pro Glu Asn Met Val Thr Phe Ser Glu Asn His Gly Val Val Ile Gln
            100                 105                 110
Pro Ala Tyr Lys Asp Lys Ile Asn Ile Thr Gln Leu Gly Leu Gln Asn
        115                 120                 125
Ser Thr Ile Thr Phe Trp Asn Ile Thr Leu Glu Asp Glu Gly Cys Tyr
    130                 135                 140
Met Cys Leu Phe Asn Thr Phe Gly Phe Gly Lys Ile Ser Gly Thr Ala
145                 150                 155                 160
Cys Leu Thr Val Tyr Val Gln Pro Ile Val Ser Leu His Tyr Lys Phe
                165                 170                 175
Ser Glu Asp His Leu Asn Ile Thr Cys Ser Ala Thr Ala Arg Pro Ala
            180                 185                 190
Pro Met Val Phe Trp Lys Val Pro Arg Ser Gly Ile Glu Asn Ser Thr
        195                 200                 205
Val Thr Leu Ser His Pro Asn Gly Thr Thr Ser Val Thr Ser Ile Leu
    210                 215                 220
His Ile Lys Asp Pro Lys Asn Gln Val Gly Lys Glu Val Ile Cys Gln
225                 230                 235                 240
Val Leu His Leu Gly Thr Val Thr Asp Phe Lys Gln Thr Val Asn Lys
                245                 250                 255
Gly Tyr Trp Phe Ser Val Pro Leu Leu Leu Ser Ile Val Ser Leu Val
            260                 265                 270
Ile Leu Leu Val Leu Ile Ser Ile Leu Leu Tyr Trp Lys Arg His Arg
        275                 280                 285
Asn Gln Asp Arg Glu Pro
    290

<210> SEQ ID NO 3
```

```
<211> LENGTH: 274
<212> TYPE: PRT
<213> ORGANISM: Homo sapiens

<400> SEQUENCE: 3

Val Ile Arg Met Pro Phe Ser His Leu Ser Thr Tyr Ser Leu Val Trp
1               5                   10                  15

Val Met Ala Ala Val Val Leu Cys Thr Ala Gln Val Gln Val Val Thr
            20                  25                  30

Gln Asp Glu Arg Glu Gln Leu Tyr Thr Thr Ala Ser Leu Lys Cys Ser
        35                  40                  45

Leu Gln Asn Ala Gln Glu Ala Leu Ile Val Thr Trp Gln Lys Lys Lys
50                  55                  60

Ala Val Ser Pro Glu Asn Met Val Thr Phe Ser Glu Asn His Gly Val
65                  70                  75                  80

Val Ile Gln Pro Ala Tyr Lys Asp Lys Ile Asn Ile Thr Gln Leu Gly
                85                  90                  95

Leu Gln Asn Ser Thr Ile Thr Phe Trp Asn Ile Thr Leu Glu Asp Glu
            100                 105                 110

Gly Cys Tyr Met Cys Leu Phe Asn Thr Phe Gly Phe Gly Lys Ile Ser
        115                 120                 125

Gly Thr Ala Cys Leu Thr Val Tyr Val Gln Pro Ile Val Ser Leu His
    130                 135                 140

Tyr Lys Phe Ser Glu Asp His Leu Asn Ile Thr Cys Ser Ala Thr Ala
145                 150                 155                 160

Arg Pro Ala Pro Met Val Phe Trp Lys Val Pro Arg Ser Gly Ile Glu
                165                 170                 175

Asn Ser Thr Val Thr Leu Ser His Pro Asn Gly Thr Thr Ser Val Thr
            180                 185                 190

Ser Ile Leu His Ile Lys Asp Pro Lys Asn Gln Val Gly Lys Glu Val
        195                 200                 205

Ile Cys Gln Val Leu His Leu Gly Thr Val Thr Asp Phe Lys Gln Thr
    210                 215                 220

Val Asn Lys Gly Tyr Trp Phe Ser Val Pro Leu Leu Leu Ser Ile Val
225                 230                 235                 240

Ser Leu Val Ile Leu Leu Val Leu Ile Ser Ile Leu Leu Tyr Trp Lys
                245                 250                 255

Arg His Arg Asn Gln Asp Arg Gly Glu Leu Ser Gln Gly Val Gln Lys
            260                 265                 270

Met Thr

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Lys Ala Ser Gln Asp Ile Asn Ser Tyr Leu Ser
1               5                   10

<210> SEQ ID NO 5
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 5

Arg Ala Asn Arg Leu Val Asp
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Leu Gln Tyr Asp Glu Phe Pro Tyr Thr
1               5

<210> SEQ ID NO 7
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Tyr Ser Phe Thr Asp Tyr Ile Ile Leu
1               5                   10

<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

His Ile Asp Pro Tyr Tyr Gly Ser Ser Asn Tyr Asn Leu Lys Phe Lys
1               5                   10                  15

Gly

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ser Lys Arg Asp Tyr Phe Asp Tyr
1               5

<210> SEQ ID NO 10
<211> LENGTH: 117
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 10

Gln Val Gln Leu Gln Gln Ser Gly Ser Glu Leu Lys Lys Pro Gly Ala
1               5                   10                  15

Ser Val Lys Ile Ser Cys Lys Ala Ser Gly Tyr Ser Phe Thr Asp Tyr
            20                  25                  30

Ile Ile Leu Trp Val Arg Gln Asn Pro Gly Lys Gly Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Ala Asp Gln Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Thr
            100                 105                 110

Leu Thr Val Ser Ser
        115

<210> SEQ ID NO 11
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Gln Met Thr Gln Ser Pro Ser Ser Leu Ser Ala Ser Ile Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Tyr Cys Leu Gln Tyr Asp Glu Phe Pro Tyr
                85                  90                  95

Thr Phe Gly Gly Gly Thr Lys Leu Glu Ile Lys Arg
            100                 105

<210> SEQ ID NO 12
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
            35                  40                  45

Gly His Ile Asp Pro Tyr Tyr Gly Ser Ser Asn Tyr Asn Leu Lys Phe
        50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
            115

<210> SEQ ID NO 13
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Met Thr Gln Ser Pro Ser Ser Leu Ser Ala Ser Val Gly Asp Arg
 1               5                   10                  15

Val Thr Ile Thr Cys Lys Ala Ser Gln Asp Ile Asn Ser Tyr Leu Ser
                20                  25                  30

Trp Phe Gln Gln Lys Pro Gly Lys Ala Pro Lys Ser Leu Ile Tyr Arg
            35                  40                  45

Ala Asn Arg Leu Val Asp Gly Val Pro Ser Arg Phe Ser Gly Ser Gly
        50                  55                  60

Ser Gly Thr Asp Phe Thr Leu Thr Ile Ser Ser Leu Gln Pro Glu Asp
 65                  70                  75                  80

Phe Ala Thr Tyr Tyr Cys Leu Gln Tyr Asp Glu Phe Pro Tyr Thr Phe
                85                  90                  95

Gly Gln Gly Thr Lys Leu Glu Ile Lys
            100                 105

<210> SEQ ID NO 14
<211> LENGTH: 157
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Ser Phe Thr Asp Tyr
                20                  25                  30

Ile Ile Leu Trp Val Arg Gln Ala Pro Gly Gln Arg Leu Glu Trp Ile
            35                  40                  45

Gly His Ile Asp Pro Tyr Tyr Gly Ser Ser Asn Tyr Asn Leu Lys Phe
        50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser
145                 150                 155

<210> SEQ ID NO 15
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105

<210> SEQ ID NO 16
<211> LENGTH: 157
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Leu

```
              100                 105                 110
Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser
145                 150                 155
```

<210> SEQ ID NO 17
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 18
<211> LENGTH: 157
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125
```

```
Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser
145                 150                 155
```

<210> SEQ ID NO 19
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 20
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

```
Gln Val Gln Leu Gln Gln Ser Gly Ser Glu Leu Lys Lys Pro Gly Ala
1               5                   10                  15

Ser Val Lys Ile Ser Cys Lys Ala Ser Gly Tyr Ser Phe Thr Asp Tyr
            20                  25                  30

Ile Ile Leu Trp Val Arg Gln Asn Pro Gly Lys Gly Leu Glu Trp Ile
        35                  40                  45

Gly His Ile Asp Pro Tyr Tyr Gly Ser Ser Asn Tyr Asn Leu Lys Phe
50                  55                  60

Lys Gly Arg Val Thr Ile Thr Ala Asp Gln Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
            435                 440
```

<210> SEQ ID NO 21
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Asp Ile Gln Met Thr Gln Ser Pro Ser Ser Leu Ser Ala Ser Ile Gly
1               5                   10                  15

Asp Arg Val Thr Ile Thr Cys Lys Ala Ser Gln Asp Ile Asn Ser Tyr
                20                  25                  30

Leu Ser Trp Phe Gln Gln Lys Pro Gly Lys Ala Pro Lys Leu Leu Ile
            35                  40                  45

Tyr Arg Ala Asn Arg Leu Val Asp Gly Val Pro Ser Arg Phe Ser Gly
```

Ser Gly Ser Gly Thr Asp Tyr Thr Leu Thr Ile Ser Ser Leu Gln Pro
65                  70                  75                  80

Glu Asp Phe Ala Val Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
        210                 215                 220

Pro Cys Pro Ala Pro Val Ala Gly Pro Ser Val Phe Leu Phe Pro
225             230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305             310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385             390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 23
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
            35                  40                  45

Tyr Arg Ala Asn Arg Leu Val Asp Gly Val Pro Ser Arg Phe Ser Gly
        50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Leu Gln Tyr Asp Glu Phe Pro Tyr
            85                  90                  95

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
```

```
                225                 230                 235                 240

Pro Lys Pro Lys Asp Thr Leu Met Ile Ser Arg Thr Pro Glu Val Thr
                        245                 250                 255

Cys Val Val Asp Val Ser Gln Glu Asp Pro Glu Val Gln Phe Asn
                        260                 265                 270

Trp Tyr Val Asp Gly Val Glu Val His Asn Ala Lys Thr Lys Pro Arg
                        275                 280                 285

Glu Glu Gln Phe Asn Ser Thr Tyr Arg Val Val Ser Val Leu Thr Val
                290                 295                 300

Leu His Gln Asp Trp Leu Asn Gly Lys Glu Tyr Lys Cys Lys Val Ser
        305                 310                 315                 320

Asn Lys Gly Leu Pro Ser Ser Ile Glu Lys Thr Ile Ser Lys Ala Lys
                        325                 330                 335

Gly Gln Pro Arg Glu Pro Gln Val Tyr Thr Leu Pro Pro Ser Gln Glu
                        340                 345                 350

Glu Met Thr Lys Asn Gln Val Ser Leu Thr Cys Leu Val Lys Gly Phe
                        355                 360                 365

Tyr Pro Ser Asp Ile Ala Val Glu Trp Glu Ser Asn Gly Gln Pro Glu
                        370                 375                 380

Asn Asn Tyr Lys Thr Thr Pro Pro Val Leu Asp Ser Asp Gly Ser Phe
        385                 390                 395                 400

Phe Leu Tyr Ser Arg Leu Thr Val Asp Lys Ser Arg Trp Gln Glu Gly
                        405                 410                 415

Asn Val Phe Ser Cys Ser Val Met His Glu Ala Leu His Asn His Tyr
                        420                 425                 430

Thr Gln Lys Ser Leu Ser Leu Ser Leu Gly Lys
                        435                 440

<210> SEQ ID NO 25
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Gln Met Thr Gln Ser Pro Ser Ser Leu Ser Ala Ser Val Gly
        1               5                   10                  15

Asp Arg Val Thr Ile Thr Cys Lys Ala Ser Gln Asp Ile Asn Ser Tyr
                        20                  25                  30

Leu Ser Trp Phe Gln Gln Lys Pro Gly Lys Ala Pro Lys Ser Leu Ile
                        35                  40                  45

Tyr Arg Ala Asn Arg Leu Val Asp Gly Val Pro Ser Arg Phe Ser Gly
                50                  55                  60

Ser Gly Ser Gly Thr Asp Phe Thr Leu Thr Ile Ser Ser Leu Gln Pro
        65                  70                  75                  80

Glu Asp Phe Ala Thr Tyr Tyr Cys Leu Gln Tyr Asp Glu Phe Pro Tyr
                        85                  90                  95

Thr Phe Gly Gln Gly Thr Lys Leu Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Ile Ile Leu Trp Val Arg Gln Ala Pro Gly Gln Arg Leu Glu Trp Met
            35                  40                  45

Gly His Ile Asp Pro Tyr Tyr Gly Ser Ser Asn Tyr Asn Leu Lys Phe
        50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
        210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

```
Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 27
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180                 185                 190
Ala Cys Glu Val Thr His Gln Gly Leu Ser Ser Pro Val Thr Lys Ser
            195                 200                 205

Phe Asn Arg Gly Glu Cys
            210

<210> SEQ ID NO 28
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300
```

```
Ser Val Met His Glu Ala Leu His Asn His Tyr Thr Gln Lys Ser Leu
305                 310                 315                 320
Ser Leu Ser Leu Gly Lys
                325
```